United States Patent
Scoble et al.

(10) Patent No.: US 12,422,369 B2
(45) Date of Patent: Sep. 23, 2025

(54) IMMUNOSENSOR

(71) Applicant: PPB Technology Pty Ltd, Oxley (AU)

(72) Inventors: Judith Scoble, Acton (AU); Charlotte Williams, Acton (AU); Stewart Nuttall, Acton (AU); Regina Surjadi, Acton (AU); Helen Dacres, Acton (AU); Stephen Trowell, Oxley (AU)

(73) Assignee: PPB TECHNOLOGY PTY LTD, Oxley (AU)

( * ) Notice: Subject to any disclaimer, the term of this patent is extended or adjusted under 35 U.S.C. 154(b) by 833 days.

(21) Appl. No.: 17/594,837

(22) PCT Filed: Apr. 30, 2020

(86) PCT No.: PCT/AU2020/050430
§ 371 (c)(1),
(2) Date: Nov. 1, 2021

(87) PCT Pub. No.: WO2020/220086
PCT Pub. Date: Nov. 5, 2020

(65) Prior Publication Data
US 2022/0268706 A1 Aug. 25, 2022

(30) Foreign Application Priority Data

May 1, 2019 (AU) ................................ 2019901483
May 8, 2019 (AU) ................................ 2019901566

(51) Int. Cl.
*G01N 21/76* (2006.01)
*C07K 16/18* (2006.01)
(Continued)

(52) U.S. Cl.
CPC ............. *G01N 21/76* (2013.01); *C07K 16/18* (2013.01); *G01N 15/14* (2013.01); *G01N 21/64* (2013.01);
(Continued)

(58) Field of Classification Search
CPC .... G01N 33/542; G01N 33/533; G01N 15/14; G01N 15/1459; G01N 21/76;
(Continued)

(56) References Cited

U.S. PATENT DOCUMENTS 8,524,457 B2 9/2013 Patterson
2010/0151591 A1 6/2010 Butlin et al.
(Continued)

FOREIGN PATENT DOCUMENTS

CN 104714014 9/2016
CN 104380085 12/2018
(Continued)

OTHER PUBLICATIONS

Wang et al., Introducing novel amorphous carbon nanoparticles as energy acceptors into a chemiluminescence resonance energy transfer immunoassay system, 2013, Royal Society of Chemistry, 138, 6753-6758. (Year: 2013).*

(Continued)

*Primary Examiner* — Kathryn Elizabeth Limbaugh
(74) *Attorney, Agent, or Firm* — Norton Rose Fulbright US LLP

(57) ABSTRACT

The present invention relates to methods for detecting analytes in a sample. The methods may also be used to determine the amount of analyte in the sample. The present invention also relates to antibody or antibody-like molecules and labelled antigens for use in these methods.

Figure 1:
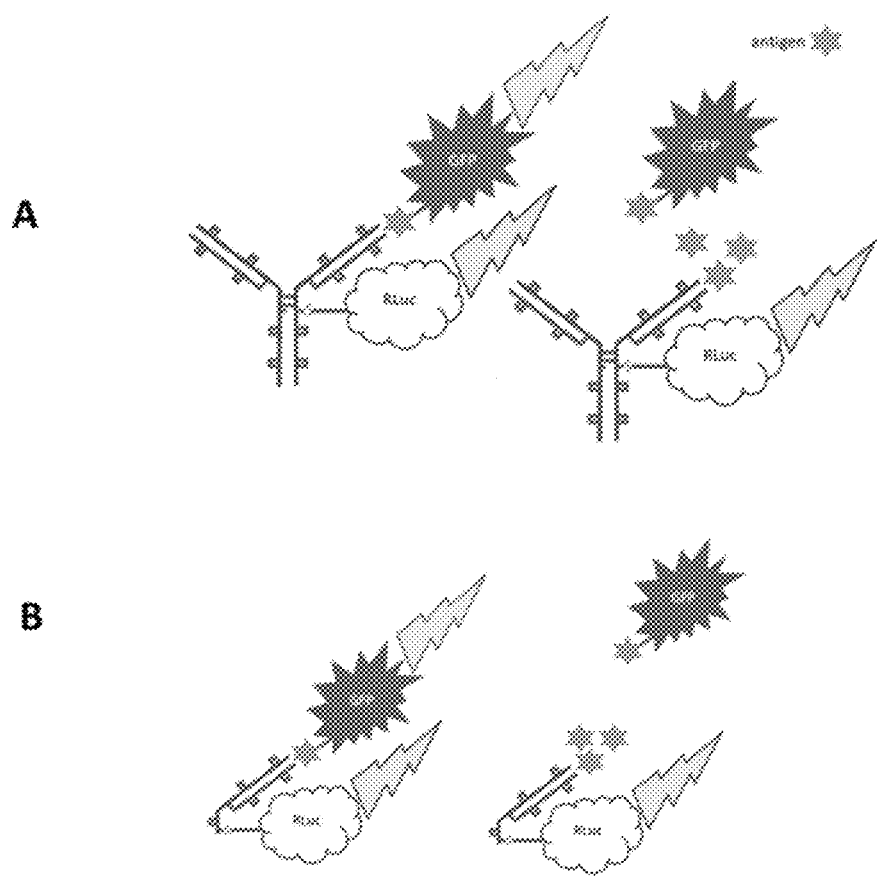

19 Claims, 6 Drawing Sheets
Specification includes a Sequence Listing.

(51) Int. Cl.
*G01N 15/14* (2024.01)
*G01N 21/64* (2006.01)
(52) U.S. Cl.
CPC ...... *C07K 2317/22* (2013.01); *C07K 2317/54* (2013.01); *C07K 2317/55* (2013.01); *C07K 2317/569* (2013.01)
(58) Field of Classification Search
CPC ........ G01N 21/64; C07K 16/18; C07K 16/44; C07K 2317/22; C07K 2317/54; C07K 2317/55; C07K 2317/569; B01L 3/502715; C12Q 1/66
See application file for complete search history.

(56) References Cited

U.S. PATENT DOCUMENTS

| | | | |
|---|---|---|---|
| 2011/0071045 | A1 | 3/2011 | Patterson |
| 2015/0094219 | A1* | 4/2015 | Trowell ............... C12Q 1/66 422/69 |
| 2016/0291014 | A1 | 10/2016 | Hao |
| 2017/0370917 | A1* | 12/2017 | Mackernan .......... C12N 9/1077 |
| 2018/0100865 | A1* | 4/2018 | Steyaert ................. A61P 31/04 |

FOREIGN PATENT DOCUMENTS

| | | |
|---|---|---|
| EP | 1382965 | 1/2004 |
| EP | 3022316 | 11/2017 |
| EP | 3111218 | 8/2018 |
| JP | 2001-124770 | 5/2001 |
| WO | WO 2013/155553 | 10/2013 |
| WO | WO 2015/067302 | 5/2015 |
| WO | WO 2017/040962 | 3/2017 |

OTHER PUBLICATIONS

Dacres, H. et al. 'Effect of enhanced Renilla luciferase and fluorescent protein variants on the Förster distance of Bioluminescence resonance energy transfer (BRET)', Biochemical and Biophysical Research Communications, (2012), vol. 425, pp. 625-629.

De, A. et al. 'Engineering Aspects of Bioluminescence Resonance Energy Transfer Systems' 'Engineering in Translational Medicine' W. Cai (ed.) (2014), Chapter 10, pp. 257-300.

Gao, H. et al. 'Amorphous carbon nanoparticle used as novel resonance energy transfer acceptor for chemiluminescent immunoassay of transferrin', Analytica Chimica Acta, (2014), vol. 819, pp. 102-107.

Hepojoki, S. et al. 'Competitive Homogenous Immunoassay for Rapid Serodiagnosis of Hantavirus Disease', Journal of Clinical Microbiology, (2015), vol. 53, No. 7 pp. 2292-2297.

International Search Report and Written Opinion for PCT/AU2020/050430 issued May 21, 2020.

Le, N. et al. 'Sub-nanomolar detection of thrombin activity on a microfluidic chip', Biomicrofluidics, (2014), vol. 8, No. 064110, pp. 1-11.

Takkinen, K. and Zvirbliene, A. 'Recent advances in homogenous immunoassays based on resonance energy transfer', Current Opinion in Biotechnology, (2019), vol. 55, pp. 16-22.

Wu, N. et al. 'Comparison of Static and Microfluidic Protease Assays using modified Bioluminescence Resonance Energy Transfer Chemistry' PLoS One, (2014), vol. 9, issue 2 e88399.

Xue, L. et al. 'Bioluminescent Antibodies for Point-of-Care Diagnostics' Angewandte Chemie International Edition, (2017), vol. 56, pp. 7112-7116.

Yu, X. et al. 'General Bioluminescence Resonance Energy Transfer Homogenous Immunoassay for Small Molecules Based on Quantum Dots', Analytical Chemistry, (2016), vol. 88, pp. 3512-3520.

Anonymous: "Chemiluminescence—Wikipedia", Apr. 30, 2019, XP09304892, Retrieved from the Internet: URL:https://web.archiveorg/web/20190430081140/https://en.wikipedia.org/wiki/Chemiluminescence [retrieved on May 23, 2023].

Arai et al., Demonstration of a Homogeneous Noncompetitive Immunoassay Based on Bioluminescence Resonance Energy Transfer, *Analytical Biochemistry*, 289 (1), 77-81, 2001.

Arts et al., "Semisynthetic Bioluminescent Sensor Proteins for Direct Detection of Antibodies and Small Molecules in Solution", *ACS Sensor*, 2(11): 1730-1736, 2017.

Bhalla N, et al., "Introduction to biosensors", *Essays Biochem*, Jun. 30, 2016; 60(1):1-8. doi: 10.1042/EBC20150001. PMID: 27365030; PMCID: PMC4986445.

Boutureira, O. et al., "Advances in Chemical Protein Modification." Chemical Reviews, 115(5): 2174-2195, 2015.

Hong, L. PT, et al., "Cancer-targeting Antibody-Drug Conjugates: Site-Specific Conjugation of Doxorubicin to Anti-EGFR 528 Fab' through a Polyethylene Glycol Linker." *Australian Journal of Chemistry*, 64(6): 779-789, 2011.

Kirley, T.L., et al., "Selective disulfide reduction for labeling and enhancement of Fab antibody fragments", *Biochemical and Biophysical Research Communications*, 480(4),:752-757, 2016.

Ohiro, Y. et al., "A Homogeneous and Noncompetitive Immunoassay Based on the Enhanced Fluorescence Resonance Energy Transfer by Leucine Zipper Interaction", *Anal. Chem.*, 74, 5786-5792, 2002.

Spicer, C.D. et al., "Selective chemical protein modification." *Nature communications*, 5(1): 4740, 2014.

Tabares-da Rosa, S. et al. "Competitive Selection from Single Domain Antibody Libraries Allows Isolation of High-Affinity Antihapten Antibodies That Are Not Favored in the llama Immune Response", *Analytical Chemistry*, vol. 83(8): 7213-20, 2011. doi:10.1021/ac201824z.

Wang, Z. et al., "Introducing novel amorphous carbon nanoparticles as energy acceptors into a chemiluminescence resonance energy transfer immunoassay system", *The Analyst*, 138(22): 6753-6758, 2013.

Yamakawa, Y. et al., "Rapid homogeneous immunoassay of peptides based on bioluminescence resonance energy transfer from firefly luciferase." *Journal of bioscience and bioengineering*, 93(6): 537-542, 2002.

Zhang, Y. et al., "Development of a homogeneous immunoassay based on the AlphaLISA method for the detection of chloramphenicol in milk, honey and eggs", *Journal of the Science of Food and Agriculture*, 92(9):1944-1947, 2012.

\* cited by examiner

IMMUNOSENSOR

CROSS-REFERENCE TO RELATED APPLICATIONS

This application is a national phase application under 35 U.S.C. § 371 of International Application No. PCT/AU2020/050430 filed Apr. 30, 2020, which claims the benefit of priority of Australian Patent Application No. 2019901483 filed May 1, 2019, and Australian Patent Application No. 2019901566 filed May 8, 2019, which are hereby incorporated by reference in their entirety.

FIELD OF THE INVENTION

The present invention relates to methods for detecting analytes in a sample. The methods may also be used to determine the amount of analyte in the sample. The present invention also relates to antibody or antibody-like molecules and labelled antigens for use in these methods.

BACKGROUND OF THE INVENTION

Methods for detecting an analyte are of critical importance in many industries, including the food, environmental and medical industries. For example, early detection of pathological conditions can permit the identification of these conditions at a stage where successful treatment is more likely. In addition, the detection of trace amounts of a food protein can help prevent severe allergic reactions to contaminated food products. There are a number of methods currently available for detecting an analyte in a sample. For example, enzyme linked immunosorbent assays (ELISA), lateral-flow immunoassays and western-blot immunoassays are widely used. All of these assays are carried out using heterogeneous assay formats and require immobilisation of antibodies or antigens on a solid surface. These assays are time laborious and prone to operator error due to the required multiple wash cycles and/or incubation/wash steps.

Biosensors have been developed for detecting an analyte in a sample. The ability of biosensors, and biological assays, to respond rapidly and specifically to a wide range of molecules makes them highly relevant to clinical diagnosis/monitoring, environmental and food safety, defence and biosecurity applications. Biosensors require biological recognition elements for analyte detection and can include peptides, enzymes, receptors, nucleic acids and antibodies (Bhalla et al., 2016). However, the identification of biological recognition elements with the required sensitivity and selectivity for detecting a particular analyte at low concentrations remains a fundamental challenge of biosensor development. Accordingly, there is a need for improved methods of detecting and quantifying the amount of an analyte in a sample, preferably methods that can be performed in real time, applied to multiple analytes and/or without having to send samples offsite for analysis.

SUMMARY OF THE INVENTION

The present inventors have identified immunosensors that can be used to detect an analyte in a sample. The present inventors have also identified a method of detecting the presence of an analyte in a sample using these immunosensors. In some embodiments, these immunosensors and methods can be used measure the concentration of an analyte in a sample.

In one aspect, there is provided a method for detecting an analyte in a sample, the method comprising:
i) contacting the sample with:
an antibody or antibody-like molecule capable of binding to the analyte attached to a first component of a chemiluminescence resonance energy transfer (CRET) pair; and
a labelled antigen comprising an antigen capable of binding to the antibody or the antibody-like molecule attached to a second component of the CRET pair;
wherein, when the labelled antigen is bound to the antibody or the antibody-like molecule, the efficiency of energy transfer between the first component of the CRET pair and the second component of the CRET pair is in the range of 10 to 75%; and
ii) determining if the efficiency of energy transfer between the first component of the CRET pair and the second component of the CRET pair has been altered in the presence of the sample,
wherein a reduction in the efficiency of energy transfer between the first and second components of the CRET pair indicates that the analyte is present in the sample.

In some embodiments, step (i) further comprises contacting the sample with a substrate.

In some embodiments, the first component of the CRET pair is a polypeptide and second component of the CRET pair is a polypeptide.

In some embodiments, the first component of the CRET pair comprises a BRET donor domain and second component of the CRET pair comprises a BRET acceptor domain. In alternative embodiments, the first component of the CRET pair comprises a BRET acceptor domain and second component of the CRET pair comprises a BRET donor domain.

In some embodiments, the antibody or antibody-like molecule is attached to the first component of the CRET pair via a linker. Suitable linkers comprise a polyethylene glycol (PEG) chain, hydrocarbon chain, a polypeptide or a polynucleotide. In some embodiments, the linker comprises $PEG_8$ to $PEG_{60}$. In some embodiments, the linker comprises $PEG_n$-L-$PEG_m$, wherein m and n are independently an integer between 0 and 40 and L is a conjugation element.

In some embodiments, the efficiency of energy transfer from the first component to the second component is in the range of 15 to 65% when the labelled antigen is bound to the antibody or antibody-like molecule.

In some embodiments, the attachment between the antibody or antibody-like molecule and the first component of the CRET pair is site-specific. In some embodiments, the first component of the CRET pair is not attached to an antigen binding site of the antibody or antibody-like molecule.

In some embodiments, the first component of the CRET pair is attached to a side-chain of a residue of the antibody or antibody-like molecule. In some embodiments, the residue is a cysteine. In some embodiments, the residue is a cysteine involved in inter-chain disulphide bonds. In some embodiments, the residue is a cysteine in a hinge region of the antibody or antibody-like molecule or the residue is a cysteine involved in a heavy chain-light chain disulphide bond or a combination of both.

In some embodiments, the first component of the CRET pair is attached to the antibody or antibody-like molecule via a carbohydrate moiety.

In some embodiments, the antibody or antibody-like molecule has two attached first components of the CRET pair which are the same.

In some embodiments, the antibody or antibody-like molecule is an IgG, IgA, IgM, IgE, monoclonal antibody, Fab', rIgG (half antibody), f(ab')$_2$, nanobody, affibody, anticalin, DARPin, monobody, avimer, microbody, chimeric antibody, scFv, scFv multimer, single domain antibody or single domain fusion antibody. In some embodiments, the antibody or antibody-like molecule is an IgG, Fab', rIgG (half antibody) or f(ab')$_2$. In some embodiments, the antibody or antibody-like molecule is an IgG. In some embodiments, the antibody or antibody-like molecule is a monoclonal antibody. In some embodiments, the antibody or antibody-like molecule is a nanobody.

In some embodiments, the analyte is a small organic molecule, drug, drug metabolite, antibiotic, hormone, allergen, naturally occurring toxin, adulterant, microorganism, peptide, protein, naturally occurring antibody, guar, lipid or nucleic acid. In some embodiments, the analyte is an allergen. In some embodiments, the analyte is an antibiotic. In some embodiments, the analyte is an antibacterial. In some embodiments, the analyte is an antifungal. In some embodiments the analyte is a naturally occurring toxin. In some embodiments the analyte is an adulterant. In some embodiments the analyte is a microorganism. In some embodiments the analyte is a small organic molecule.

In some embodiments, the first or second component of the CRET pair is a bioluminescent protein selected from the group consisting of a luciferase, a β-galactosidase, a lactamase, a horseradish peroxidase, an alkaline phosphatase, a β-glucuronidase or a β-glucosidase. In some embodiments, the bioluminescent protein is a luciferase selected from the group consisting of *Renilla* luciferase, a Firefly luciferase, a Coelenterate luciferase, a North American glow worm luciferase, a click beetle luciferase, a railroad worm luciferase, a bacterial luciferase, a *Gaussia* luciferase, Aequorin, an *Arachnocampa* luciferase, an Oplophorus *gracilirostris* luciferase or a biologically active variant or fragment of any one, or chimera of two or more, thereof. In some embodiments, the bioluminescent protein is *Renilla* luciferase or a biologically active variant or fragment thereof. In some embodiments, the bioluminescent protein is RLuc8.

In some embodiments, the first or second component of the CRET pair is capable of modifying a substrate. Suitable substrates include, but are not limited to, luciferin, calcium, coelenterazine, furimazine or a derivative, analogue or stabilised derivative of coelenterazine, luciferin or furimazine.

In some embodiments, the first or second component of the CRET pair is a fluorescent acceptor domain. In some embodiments, the fluorescent acceptor domain is selected from the group consisting of green fluorescent protein (GFP), blue fluorescent variant of GFP (BFP), cyan fluorescent variant of GFP (CFP), yellow fluorescent variant of GFP (YFP), enhanced GFP (EGFP), superfolder GFP, Azami green, mWasabi, TagGFP, Turbo GFP, AcGFP, ZsGreen, T-Sapphire, enhanced CFP (ECFP), CyPET, AmCyan1, Midori-Ishi green, TagCFP, mTFP1 (Teal), enhanced YFP (EYFP), GFPS65T, Emerald, Venus, mOrange, Topaz, mCitrine, YPet, TagYFP, PhiYFP, ZsYellow, mBanana, Kusabira Orange, Kusabira Orange2, mOrange, mOrange2, GFPuv, destabilised EGFP (dEGFP), destabilised ECFP (dECFP), destabilised EYFP (dEYFP), dKeima-Tandem, HcRed, HcRed-Tandem, t-HcRed, AQ143, DsRed, DsRed2, t-dimer2, tdimer2(12), mRFP1, mTangarine, pocilloporin, *Renilla* GFP, *Aequorea victoria* GFP, Monster GFP, paGFP, Kaede protein, tdTomato, mCherry, mRuby, mApple, mStrawberry, AsRed2, JRed, HcRedl, mRaspberry, mPlum, TagRFP, TurBoFP and Phycobiliproteins including R-Phycoerythrin (R-PE), B-Phycoerythrin (B-PE), C-Phycocyanin (CPC) Allophycocyanin (APC) and R-Phycocyanin (RPC) and a biologically active variant or fragment of any one thereof. In some embodiments, the fluorescent acceptor domain is GFP or a biologically active variant or fragment thereof. In some embodiments, the fluorescent acceptor domain is GFP$^2$.

In some embodiments, the first component of the CRET pair is RLuc8 and the second component of the CRET pair is GFP$^2$.

In some embodiments, when the labelled antigen is specifically bound to the antibody or antibody-like molecule, the separation and relative orientation of the donor domain and the acceptor domain is within ±50% of the Förster distance of the BRET pair. In some embodiments, the Förster distance of the BRET pair is between about 4 nm and about 18 nm, or is between about 6 nm and about 12 nm, or is between about 7.5 nm and 10.5 nm.

In some embodiments, step (ii) comprises determining if the efficiency of energy transfer between the first component of the CRET pair and the second component of the CRET pair has been reduced in the presence of the sample.

In some embodiments, step (i) comprises
(a) first contacting the sample with the antibody or antibody-like molecule and then contacting the resulting mixture with the labelled antigen;
(b) first contacting the sample with the labelled antigen and then contacting the resulting mixture with the antibody or antibody-like molecule; or
(c) contacting the sample with the antibody or antibody-like molecule and the labelled antigen at the same time.

In some embodiments, the method does not require a secondary antibody. In some embodiments, the method further comprises determining the concentration of the analyte in the sample.

In another aspect, there is provided a CRET pair comprising:
an antibody or antibody-like molecule capable of binding to an analyte attached to a first component of a CRET pair; and
a labelled antigen comprising an antigen capable of binding to the antibody or antibody-like molecule attached to a second component of a CRET pair;
wherein when the labelled antigen is bound to the antibody or antibody-like molecule the efficiency of energy transfer between the first component of the CRET pair and the second component of the CRET pair is in the range of 10 to 75%.

In yet another aspect, there is provided an antibody or antibody-like molecule attached to a first component of a CRET pair and capable of binding to
i) an analyte; and
ii) a labelled antigen comprising an antigen capable of binding to the antibody or antibody-like molecule attached to a second component of a CRET pair,
wherein when the labelled antigen is bound to the antibody or antibody-like molecule the efficiency of energy transfer between the first component and the second component is in the range of 10 to 75%.

In yet another aspect, there is provided a microfluidic system for detecting an analyte in a sample, the system comprising
i) at least one reservoir suitable for containing an antibody or antibody-like molecule capable of binding to the analyte attached to a first component of a CRET pair,
ii) at least one reservoir suitable for containing a labelled antigen comprising an antigen capable of binding to the antibody or antibody-like molecule attached to a second component of the CRET pair;
iii) a microfluidic device comprising one or more microchannels,
iv) means for mixing the antibody or antibody-like molecule, the labelled antigen, the sample and a substrate of the first or second component of the CRET pair in the device,
v) a reaction chamber for detecting binding of the analyte to the antibody or antibody-like molecule, and
vi) an electro-optical sensing device,
wherein, when the labelled antigen is bound to the antibody or antibody-like molecule, the efficiency of energy transfer between the first component of the CRET pair and the second component of the CRET pair is in the range of 10 to 75%; and
wherein a reduction in the efficiency of energy transfer between the first and second components of the CRET pair indicates the analyte is present in the sample.

In some embodiments, the antibody or antibody-like molecule is not fixed to the device. In some embodiments, the antibody or antibody-like molecule, labelled antigen and substrate enter the device through different microchannels. In some embodiments, the microfluidic device comprises at least two input microchannels, wherein one of the input microchannels is for flowing the antibody or antibody-like molecule into the device.

In some embodiments, the microfluidic system can be used to detect the analyte in real time. In some embodiments, the microfluidic device is designed to enable the detection of two or more analytes.

In some embodiments, the electro-optical sensing device comprises at least two different wavelength channels. In some embodiments, the electro-optical sensing device is capable of simultaneously, or in rapid succession, detecting two different wavelength channels. In some embodiments, the electro-optical sensing device is capable of detecting two different wavelength channels in less than 1 second.

In yet another aspect, there is provided a method of identifying an antibody or antibody-like molecule capable of binding to an analyte, the method comprising
i) obtaining two or more antibodies or antibody-like molecules which have different linkers which link the antibody or antibody-like molecule to a first component of a CRET pair,
ii) contacting the two or more antibodies or antibody-like molecules with a labelled antigen comprising an antigen capable of binding to the antibody or antibody-like molecule attached to a second component of the CRET pair,
iii) measuring the efficiency of energy transfer between the first component of the CRET pair and the second component of the CRET pair, and
iv) selecting at least one antibody or antibody-like molecule which, when bound to the labelled antigen, has an efficiency of energy transfer between the first component of the CRET pair and the second component of the CRET pair which is in the range of 10 to 75%.

In some embodiments, step iv) comprises selecting the antibody or antibody-like molecule which, when bound to the labelled antigen, has the higher efficiency of energy transfer between the first component of the CRET pair and the second component of the CRET pair of the two or more antibodies or antibody-like molecules.

In some embodiments, the efficiency of energy transfer between the first component of the CRET pair and the second component of the CRET pair of the selected antibody or antibody-like molecule, when bound to the labelled antigen, is in the range of 50 to 75%.

In some embodiments, the method further comprises:
v) obtaining two or more labelled antigens, each labelled antigen comprising an antigen capable of binding the selected antibody or antibody-like molecule attached to a second component of a CRET pair via an optional linker; wherein the two or more labelled antigens comprise (i) different linkers, and/or (ii) different length antigen,
vi) contacting the two or more labelled antigens with the selected antibody or antibody-like molecule capable of binding to an analyte attached to a first component of the CRET pair,
vii) measuring the efficiency of energy transfer between the first component of the CRET pair and the second component of the CRET pair, and
viii) selecting at least one labelled antigen which, when bound to the selected antibody or antibody-like molecule, has an efficiency of energy transfer between the first component of the CRET pair and the second component of the CRET pair which is in the range of 10 to 75%.

In yet another aspect, there is provided a method of identifying a labelled antigen, the method comprising
i) obtaining two or more labelled antigens, each labelled antigen comprising an antigen capable of binding an antibody or antibody-like molecule attached to a second component of a CRET pair via an optional linker; wherein the two or more labelled antigens comprise (i) different linkers; and/or (ii) different length antigen,
ii) contacting the two or more labelled antigens with an antibody or antibody-like molecule capable of binding to an analyte attached to a first component of the CRET pair,
iii) measuring the efficiency of energy transfer between the first component of the CRET pair and the second component of the CRET pair, and
iv) selecting at least one labelled antigen which, when bound to the antibody or antibody-like molecule, has an efficiency of energy transfer between the first component of the CRET pair and the second component of the CRET pair which is in the range of 10 to 75%.

In some embodiments, step iv) comprises selecting the labelled antigen which, when bound to the antibody or antibody-like molecule, has the higher efficiency of energy transfer between the first component of the CRET pair and the second component of the CRET pair of the two or more labelled antigens.

In some embodiments, the efficiency of energy transfer between the first component of the CRET pair and the second component of the CRET pair of the selected labelled antigen when bound to the antibody or antibody-like molecule is in the range of 50 to 75%.

In some embodiments, the method further comprises:
v) obtaining two or more antibodies or antibody-like molecules which have different linkers which link the antibody or antibody-like molecule to a first component of a CRET pair,
vi) contacting the two or more antibodies or antibody-like molecules with the selected labelled antigen,
vii) measuring the efficiency of energy transfer between the first component of the CRET pair and the second component of the CRET pair, and
viii) selecting at least one antibody or antibody-like molecule which, when bound to the selected labelled antigen, has an efficiency of energy transfer between the first component of the CRET pair and the second component of the CRET pair which is in the range of 10 to 75%.

In yet another aspect, there is provided a method of identifying a CRET pair, the method comprising
- i) obtaining two or more antibodies or antibody-like molecules which have different linkers which link the antibody or antibody-like molecule to a first component of a CRET pair,
- ii) obtaining two or more labelled antigens, each labelled antigen comprising an antigen capable of binding to the antibody or antibody-like molecule attached to a second component of a CRET pair via an optional linker; wherein the two or more labelled antigens comprise (i) different linkers; and/or (ii) different length antigen,
- iii) contacting the two or more antibodies or antibody-like molecules with the two or more labelled antigens,
- iv) measuring the efficiency of energy transfer between the first component of the CRET pair and the second component of the CRET pair, and
- v) selecting at least one CRET pair, the selected CRET pair comprising one antibody or antibody-like molecule attached to a first component of a CRET pair and a labelled antigen attached to a second component of a CRET pair, wherein, when the selected antibody or antibody-like molecule is bound to the selected labelled antigen, the efficiency of energy transfer between the first component of the CRET pair and the second component of the CRET pair is in the range of 10 to 75%.

In yet another aspect, there is provided a method of classifying a sample, the method comprising i) contacting a sample with
- a) an antibody or antibody-like molecule capable of binding to an analyte attached to a first component of a CRET pair, and
- b) a labelled antigen comprising an antigen capable of binding to the antibody or antibody-like molecule attached to a second component of a CRET pair, wherein, when the labelled antigen is bound to the antibody or antibody-like molecule, the efficiency of energy transfer between the first component and the second component is in the range of 10 to 75%, wherein the efficiency of energy transfer between the first and second components of the CRET pair is altered when one or more analytes binds the antibody or antibody-like molecule; and
- ii) classifying the sample based on the alteration of the efficiency of energy transfer.

In some embodiments, step (ii) comprises one or more or all of:
- A) detecting modification of a substrate by the first or second component of the CRET pair using an electro-optical sensing device,
- B) processing at least one signal from the electro-optical sensing device and correlating the pattern of electro-optical responses with one or more pre-determined characteristics of one or more samples of interest, and
- C) classifying the sample based on the correlation of the pattern of responses.

In some embodiments, there is provided a method of classifying a sample, the method comprising
- i) contacting a sample with
  - a) an antibody or antibody-like molecule capable of binding to an analyte attached to a first component of a CRET pair,
  - b) a labelled antigen comprising an antigen capable of binding to the antibody or antibody-like molecule attached to a second component of a CRET pair,
  - c) a substrate of one of the first or second component of the CRET pair,
  wherein, when the labelled antigen is bound to the antibody or antibody-like molecule, the efficiency of energy transfer between the first component and the second component is in the range of 10 to 75%,
- ii) detecting modification of the substrate by the first or second component of the CRET pair using an electro-optical sensing device,
- iii) processing at least one signal from the electro-optical sensing device and correlating the pattern of electro-optical responses with one or more pre-determined characteristics of one or more samples of interest, and
- iv) classifying the sample based on the correlation of the pattern of responses, wherein the efficiency of energy transfer between the first and second components of the CRET pair is altered when one or more analytes binds the antibody or antibody-like molecule.

In some embodiments, step (i) comprises
- A) flowing through a microfluidic device comprising one or more microchannels,
  - a) the sample,
  - b) the antibody or antibody-like molecule,
  - c) the labelled antigen, and
  - d) a substrate a substrate of the first or second component of the CRET pair; and
- B) mixing the antibody or antibody-like molecule, labelled antigen, sample and substrate in the device.

In some embodiments, the method comprises two or more different antibody-like molecules each of which binds a different analyte or range of analytes and two or more different labelled antigens, and step v) comprises classifying the sample based on the presence, absence or concentration of each of the analytes or range of analytes.

In some embodiments, the method can be used to classify the sample in real time.

In some embodiments, the antibody or antibody-like molecule is not fixed to the device. In some embodiments, the antibody or antibody-like molecule and substrate enter the device through different microchannels.

In yet another aspect, there is provided a microfluidic system for classifying a sample, the system comprising
- i) at least one reservoir suitable for containing an antibody or antibody-like molecule capable of binding to the analyte attached to a first component of a CRET pair,
- ii) at least one reservoir suitable for containing a labelled antigen comprising an antigen capable of binding to the antibody or antibody-like molecule attached to a second component of the CRET pair;
- iii) a microfluidic device comprising one or more microchannels,
- iv) means for mixing the antibody or antibody-like molecule, the labelled antigen, the sample and a substrate of the first or second component of the CRET pair in the device,
- v) a reaction chamber for detecting binding of the analyte to the antibody or antibody-like molecule, and
- vi) an electro-optical sensing device, wherein, when the labelled antigen is bound to the antibody or antibody-like molecule, the efficiency of energy transfer between the first component of the CRET pair and the second component of the CRET pair is in the range of 10 to 75%; and wherein a reduction in the efficiency of energy transfer between the first and second components of the CRET pair indicates the analyte is present in the sample.

In some embodiments, the microfluidic system comprises two or more different antibody or antibody-like molecules each of which binds a different analyte or range of analytes and two or more different labelled antigens. In some embodiments, the antibody or antibody-like molecule is not fixed to the device. In some embodiments, the antibody or antibody-like molecule, labelled antigen and substrate enter the device through different microchannels. In some embodiments, the microfluidic device comprises at least two input microchannels, wherein one of the input microchannels is for flowing the antibody or antibody-like molecule into the device.

In some embodiments, the microfluidic system can be used to classify samples in real time.

In yet another aspect there is provided, a method of detecting an analyte in a sample, the method comprising
i) contacting the sample, in the presence of coelenterazine, with:
  a) an antibody or antibody-like molecule capable of binding to the analyte attached to *Renilla* luciferase or a variant thereof; and
  b) a labelled antigen comprising an antigen capable of binding to the antibody or antibody-like molecule attached to green fluorescent protein 2; and
ii) determining whether bioluminescent resonance energy transfer (BRET) between the bioluminescent protein and the acceptor molecule is modified, wherein a reduction in the efficiency of energy transfer between the bioluminescent protein and the acceptor molecule indicates the analyte is present in the sample.

The inventors of the present subject matter, have found that the CRET based methods described here provide a number of advantages to previously described methods, including increased sensitivity and/or shorter assay times. The methods described herein can also be applied to a wide range of analytes.

Any embodiment herein shall be taken to apply mutatis mutandis to any other embodiment unless specifically stated otherwise.

The present invention is not to be limited in scope by the specific embodiments described herein, which are intended for the purpose of exemplification only. Functionally-equivalent products, compositions and methods are clearly within the scope of the invention, as described herein.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

The invention is hereinafter described by way of the following non-limiting Examples and with reference to the accompanying.

BRIEF DESCRIPTION OF THE ACCOMPANYING DRAWINGS

FIG. 1—Illustrative immunosensor for detecting an analyte as defined herein. (A) In the illustrated embodiment, the antibody is attached to a bioluminescent protein and the antigen is attached to a fluorescent protein. (B) In the illustrated embodiment, the Fab' is attached to a bioluminescent protein and the antigen is attached to a fluorescent protein. In both embodiments, binding of the analyte (in these embodiments, unlabelled antigen) to the antibody reduces the efficiency of energy transfer between the bioluminescent protein and the fluorescent protein in the presence of a substrate for the bioluminescent protein.

Figure 2:
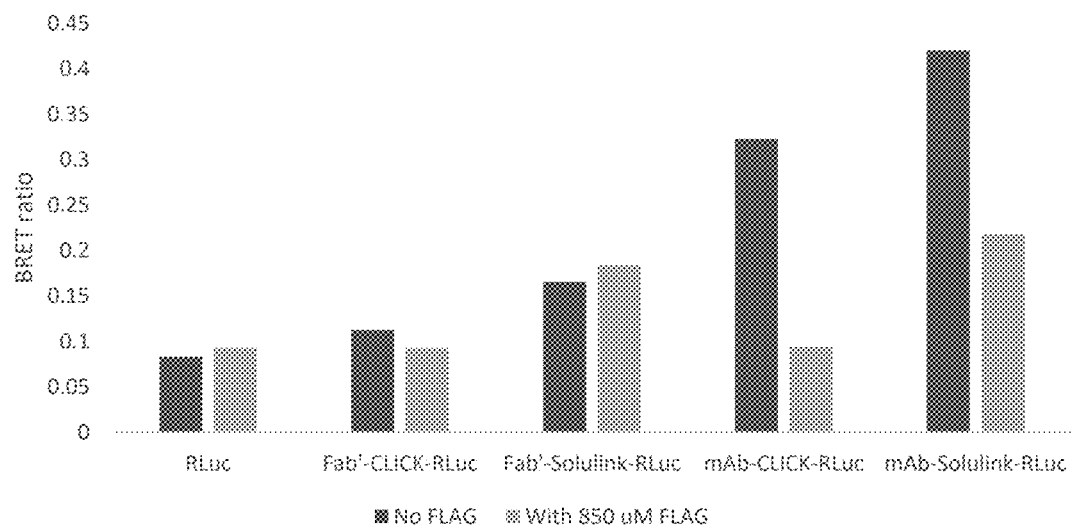

FIG. 2—Effect of FLAG peptide on BRET ratio of exemplified immunosensors. BRET ratio determined for unconjugated RLuc8, and RLuc8 conjugates incubated with FLAG-GFP$^2$ (61 nM) alone (dark grey bar) or presence of 0.85 mM free FLAG peptide (light grey bar). The concentration of RLuc8 in the assay was 5 nM, that of Fab'-CLICK-RLuc8 was estimated to be 33 nM, Fab'-Solulink-RLuc8 46 nM, antibody-CLICK-RLuc8 66 nM and antibody-Solulink-RLuc8 15 nM.

Figure 3:
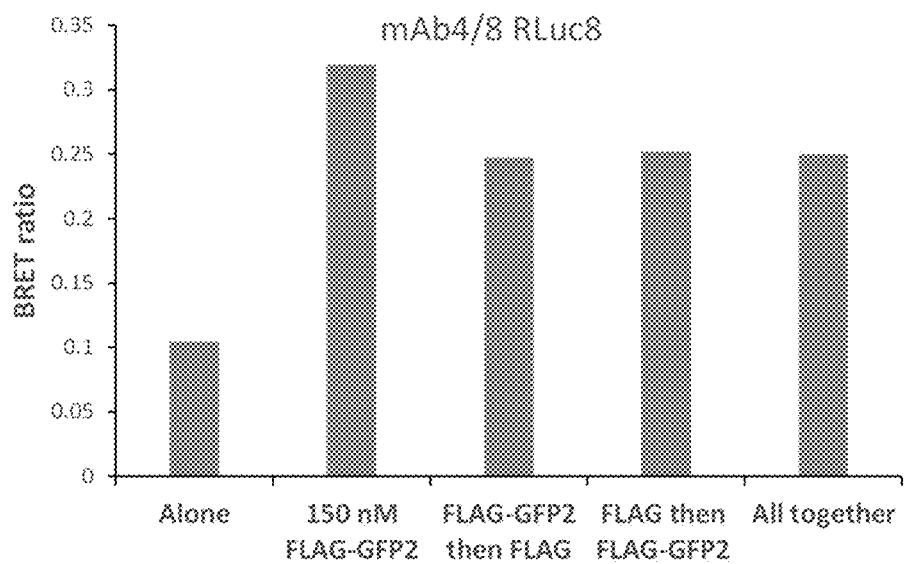

FIG. 3—The effect of the order of addition of the FLAG peptide on the response to FLAG peptide addition. The FLAG peptide was added to a composition comprising the antibody-CLICK-RLuc8 conjugate before, after or at the same time as FLAG-GFP$^2$—and the BRET ratio recorded. The concentration of antibody-CLICK-RLuc8 (mAB4/8 RLuc8) was 5 nM, FLAG-GFP$^2$ 150 nM, and FLAG peptide 100 nM.

FIG. 4—(A) The BRET ratios obtained for Click-PEG-linked 50 nM antibody:RLuc8 conjugates alone (white bar) or in the presence of 100 nM FLAG-GFP$^2$ (light grey bar), 200 nM FLAG-GFP$^2$ (dark grey bar) or 200 nM FLAG-GFP$^2$ and 1 μM FLAG (black bar). The PEG linkers used to prepare the conjugates are indicated in their names, such that e.g., mAb-4/8-Luc refers to the conjugate of antibody-PEG4-DBCO and azido-PEG8-RLuc8. (B) BRET ratio of 50 nM Fab':RLuc8 conjugates alone (light grey bar) or in the presence of 200 nM FLAG-GFP$^2$ (medium grey bar) or 200 nM FLAG-GFP$^2$ and 1 μM FLAG peptide (dark grey bar).

Figure 5:
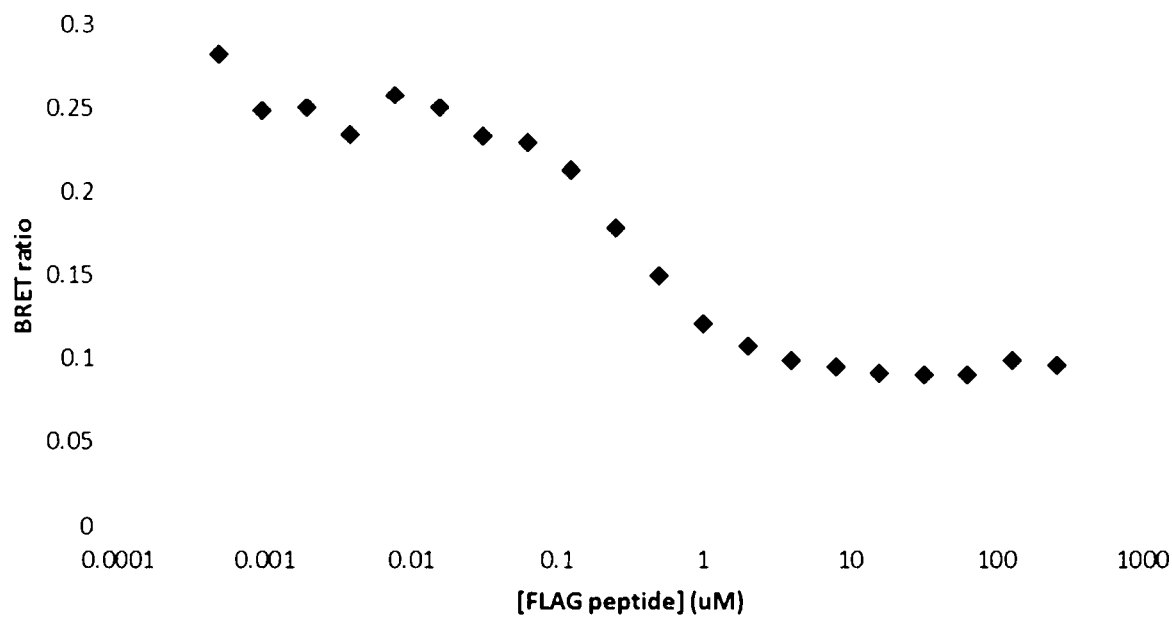

FIG. 5—BRET ratios determined for the antibody-12/36-RLuc8 conjugate (50 nM) with FLAG-GFP$^2$ (200 nM) and the free FLAG peptide, plotted against the concentration of FLAG peptide (0.000488-256 μM). BRET ratios were recorded with the Fluorostar Optima.

Figure 6:
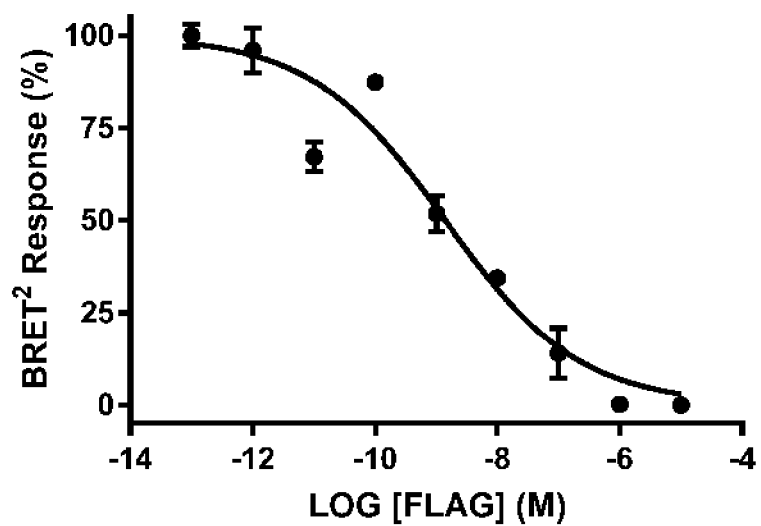

FIG. 6—Calibration of FLAG peptide (mean±SD, n=3) with 10 nM FLAG-GFP$^2$ and 5 nM mAb-24/36-RLuc8 with an incubation of 5 minutes. BRET ratios were recorded with the Clariostar.

Figure 7:
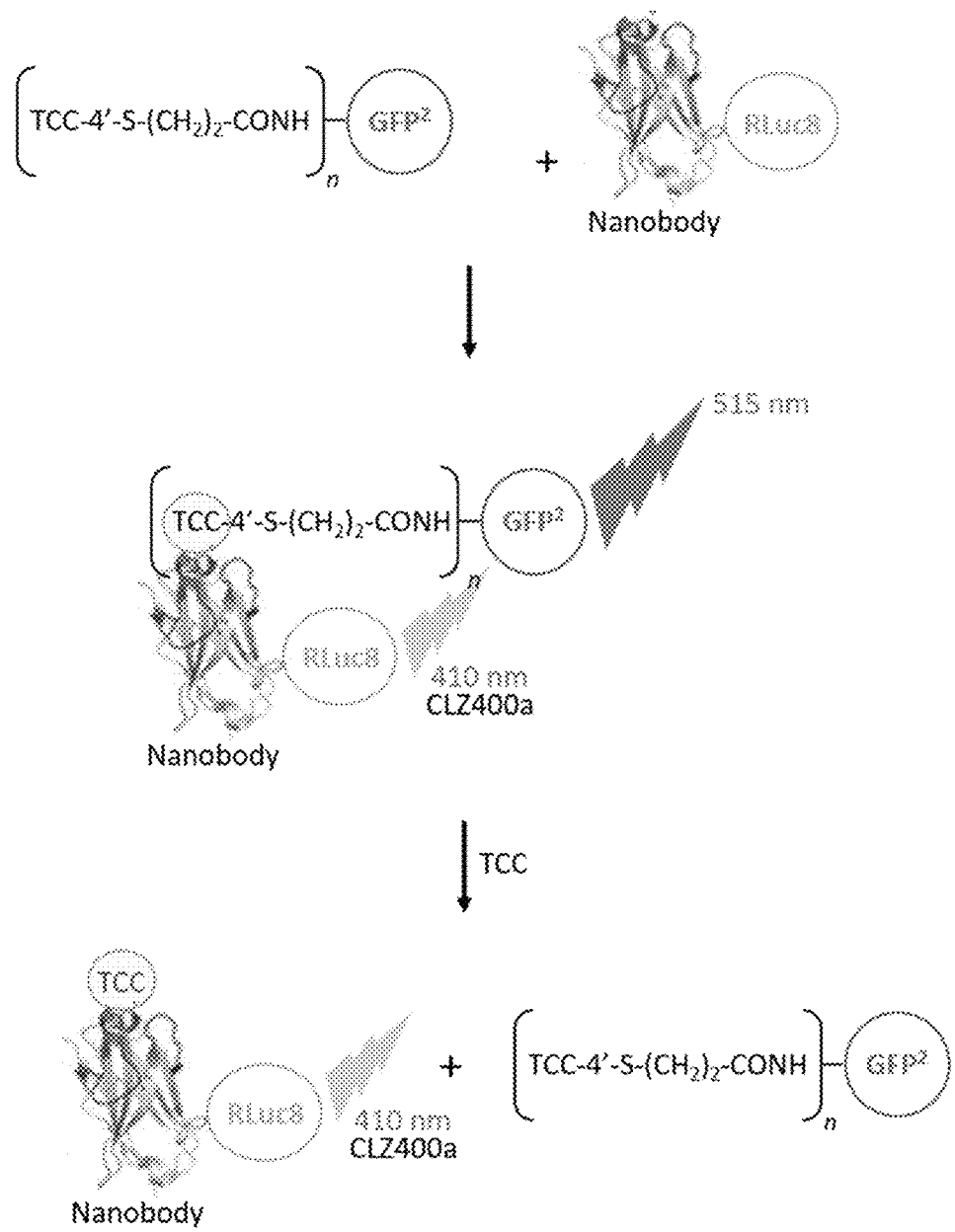

FIG. 7—Schematic of competitive assay for detecting small molecule binding to an immunosensor. In the illustrated embodiment, the nanobody is conjugated to the bioluminescent protein, RLuc8 and the antigen, a TCC analogue, is conjugated to GFP$^2$. The addition of unconjugated analyte (the unlabelled antigen TCC) reduces the efficiency of energy transfer between the bioluminescent protein and the fluorescent protein in the presence of a substrate for the bioluminescent protein and a decrease in the BRET$^2$ ratio is observed.

Figure 8:
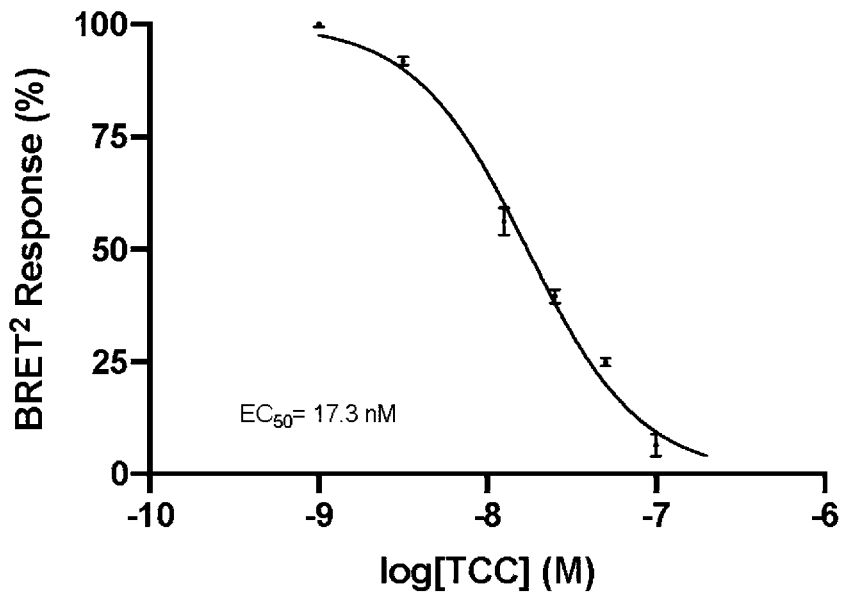

FIG. 8—TCC concentration dependence of the nanobody sensor T9NB1-RLuc8/TCC-4'-S—(CH$_2$)$_2$—CO-GFP$^2$ response in 2% DMSO/PBS (mean±SD, n=3) expressed as the percentage of maximal BRET$^2$ ratio upon addition of 10 μM coelenterazine 400a (1 μL in EtOH) to 10 nM of T9NB1-RLuc8/TCC-4'-S—(CH$_2$)$_2$—CO-GFP$^2$ nanobody sensor after 5 minutes incubation at 22° C. EC$_{50=17}$ nM.

Figure 9:
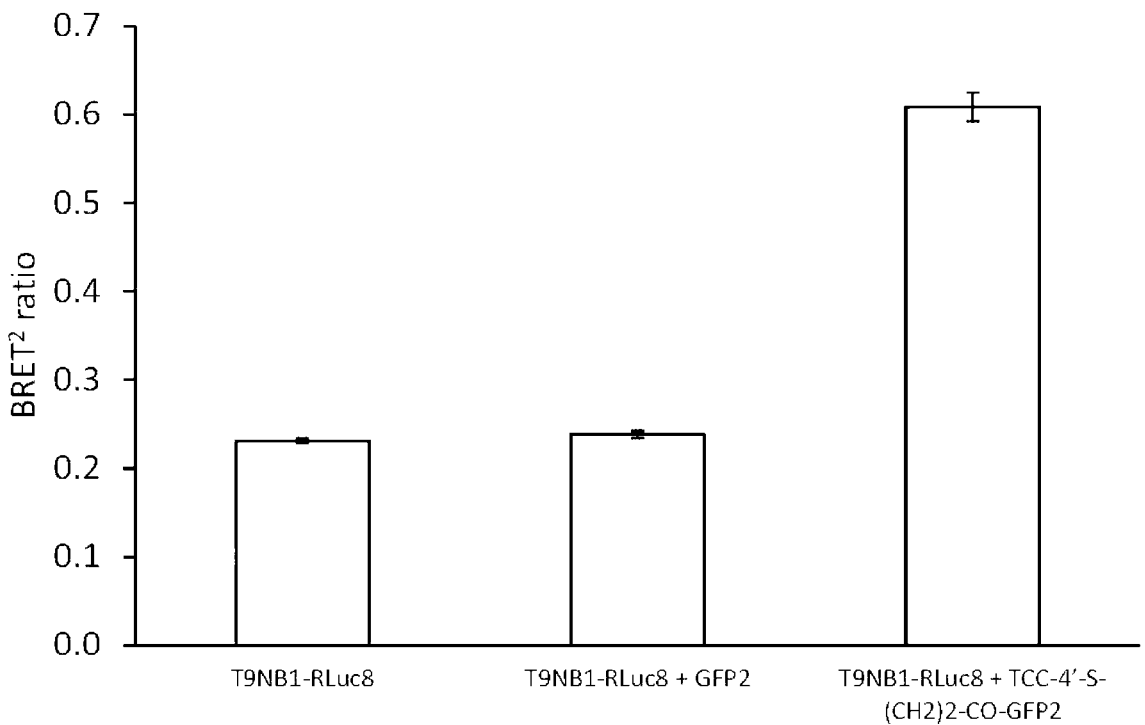

FIG. 9—BRET$^2$ ratios (means±SD, n=3) of 10 nM of purified T9NB1-RLuc8 nanobody fusion, purified T9NB1-RLuc8 nanobody fusion and GFP$^2$ and purified T9NB1-RLuc8 nanobody fusion and TCC-4'-S—(CH$_2$)$_2$—CO-GFP$^2$ fusion in 2% DMSO/PBS. Luminescence intensities were recorded following the addition of 10 μM coelenterazine 400a substrate, after 5 minutes incubation at 22° C.

KEY TO THE SEQUENCE LISTING

SEQ ID NO's 1 to 3—linker sequences.
SEQ ID NO: 4—FLAG-GFP$^2$.
SEQ ID NO: 5—N-His-RLuc8.
SEQ ID NO: 6—FLAG-RLuc8.
SEQ ID NO: 7—FLAG peptide.
SEQ ID NO: 8—N-His-T9NB1-RLuc8.

DETAILED DESCRIPTION OF THE INVENTION

General Techniques and Definitions

Unless specifically defined otherwise, all technical and scientific terms used herein shall be taken to have the same meaning as commonly understood by one of ordinary skill in the art (e.g., in CRET based sensor technology—particularly BRET based sensor technology, molecular biology, protein chemistry, bioconjugaton techniques, biochemistry and the like).

Unless otherwise indicated, the recombinant protein, cell culture, bioconjugation, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al., (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al., (editors) Current Protocols in Immunology, John Wiley & Sons (including all updates until present), Greg T. Hermanson, Bioconjugate Techniques. Elsevier Inc. (2013).

The term "and/or", e.g., "X and/or Y" shall be understood to mean either "X and Y" or "X or Y" and shall be taken to provide explicit support for both meanings or for either meaning.

Unless the context suggests otherwise, the mention of a term in singular such as sensor and substrate clearly means the plural as well. For instance, logically many individual molecules will be flowed through the device or contained within a well rather than a single molecule.

As used herein, the term about, unless stated to the contrary, refers to +/−10%, more preferably +/−5%, even more preferably +/−1%, of the designated value.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Unless indicated or the context indicates otherwise, % concentration is weight/volume (% w/v).

As used herein, the term "attached" is defined broadly and is intended to include, without being limited to, covalent and noncovalent interactions. A covalent interaction is a chemical linkage between two atoms or radicals formed by the sharing of a pair of electrons (i.e., a single bond), two pairs of electrons (i.e., a double bond) or three pairs of electrons (i.e., a triple bond). Covalent interactions are also known in the art as electron pair interactions or electron pair bonds. Examples of covalent attachments include disulphide bonds, amide bonds, thioether bonds and the like. Noncovalent interactions are much weaker than covalent interactions, but play a major role in determining the three-dimensional structure of macromolecular structures. Noncovalent interactions include, but are not limited to, van der Waals interactions, hydrogen bonds, weak chemical bonds (i.e., via short-range noncovalent forces), hydrophobic interactions, ionic bonds and the like. A review of noncovalent interactions can be found in Alberts et al., in Molecular Biology of the Cell, 3rd edition, Garland Publishing, 1994. Examples of a non-covalent attachment includes the Avidin/streptavidin-biotin complex, antibody/antigen complex, DNA duplex, RNA/DNA duplex, nucleic acid-protein complexes and the like. In some embodiments, "attached" is preferably covalently attached.

As used herein, the terms "bind," "binding," "interact," "interacting," "associated with" are intended to include, but are not limited to, non-covalent interactions.

As used herein, the term "contacting" refers to bringing two or more chemical molecules to close proximity so that a reaction and/or interaction between the two or more chemical molecules can occur. In some embodiments, the term "contacting" refers to bringing two or more chemical molecules to close proximity so that two or more chemical molecules can form a complex.

Antibody or Antibody-Like Molecule

As used herein, antibody is defined broadly and includes antibodies and antigen binding fragments thereof. The term "antibodies" as used herein refers to all isotypes of immunoglobulins, including IgG, IgM, IgA, IgD, and IgE. As used herein, "isotype" refers to the antibody class (e.g. IgM or IgG1) that is encoded by heavy chain constant region genes. The term "immunoglobulin" includes the subtypes of these immunoglobulins, such as such as IgG1, IgG2, IgG3, IgG4, IgM, IgA1, IgA2, IgAsec, etc. Of these immunoglobulins, IgG are preferred. The antibodies may be of any species of origin, including (for example) mouse, rat, rabbit, horse, or human, or may be chimeric antibodies (e.g., M. Walker et al., 1989). Suitable antibodies include a natural antibody from any organism, an engineered antibody or an antibody generated recombinantly for experimental, therapeutic or other purposes. The term "antibody" as used herein includes antibody fragments which retain the capability of binding to a target antigen, for example, Fab, Fab', F(ab')$_2$, Fv, scFv fragments, other antigen-binding subsequences of antibodies and can include those produced by the modification of whole antibodies or those synthesized de novo using recombinant DNA technologies, and the corresponding fragments obtained from antibodies other than IgG. These antibody fragments are obtained using conventional procedures, such as proteolytic fragmentation procedures, as described in J. Goding, Monoclonal Antibodies: Principles and Practice, pp 98-118 (N.Y. Academic Press 1983), as well as by other techniques known to those with skill in the art. The fragments are screened for utility in the same manner as are intact antibodies.

Suitable antibodies or antigen binding fragments include, but are not limited to, IgG, IgA, IgM, IgE, monoclonal antibody, Fab', rIgG (half antibody), f(ab')$_2$, nanobody, chimeric antibody, scFv, scFv multimer, single domain antibody or single domain fusion antibody. In some embodiments, the antibody or antibody-like molecule is a monoclonal antibody or an antigen binding fragments thereof. The term "monoclonal antibody," as used herein, refers to a preparation of antibody molecules of single molecular composition. A monoclonal antibody displays a single binding specificity and affinity for a particular epitope.

As used herein, "specific binding" (as well as the terms "specifically bound" and "specifically bind") refers to antibody or antibody-like molecule binding to a predetermined antigen with a preference that enables the antibody to be used to distinguish the antigen from others to an extent that permits the assays described herein. Typically, the antibody binds with an affinity that is at least two-fold greater than its affinity for binding to antigens other than the predetermined antigen. In some embodiments, the antibody or antibody-like molecule is forms a complex with the antigen having a dissociation constant (KD) of 100 μM or less, 10 μM or less, 1 μM or less, 500 mM or less, 100 nM or less, 10 nM or less, 1 nM or less, 500 μM or less or 100 μM or less. Unless indicated otherwise, the dissociation constant is measured at neutral pH and room temperature using a technique known to the person skilled in the art, for example SPR, quartz crustal microbalance or ITC.

The antibodies or antibody-like molecules useful in the present disclosure can be produced by a variety of techniques known in the art. Monoclonal antibody production may be effected by techniques known in the art.

In other embodiments, the antibodies can be recombinant antibodies. The term "recombinant antibody", as used herein, is intended to include antibodies that are prepared, expressed, created or isolated by recombinant means, such as antibodies isolated from an animal (e.g., a mouse) that is transgenic for another species' immunoglobulin genes, antibodies expressed using a recombinant expression vector transfected into a host cell, antibodies isolated from a recombinant, combinatorial antibody library, or antibodies prepared, expressed, created or isolated by any other means that involves splicing of immunoglobulin gene sequences to other DNA sequences.

In some embodiments, the antibodies may be chimeric antibodies produced in accordance with known techniques. For example, chimeric monoclonal antibodies may be complementarily determining region-grafted antibodies (or "CDR-grafted antibodies") produced in accordance with known techniques. Monoclonal Fab fragments may be produced in *Escherichia coli* by recombinant techniques known to those skilled in the art (Huse et al., 1989).

As used herein, an "antibody-like" molecule refers to a molecule, which like an antibody, can specifically bind an antigen but is not structurally related to an antibody. As used herein, an antibody-like molecule is not an antibody or a fragment thereof. Suitable antibody-like molecules include, but are not limited to, affibody, anticalin, DARPin, monobody, avimer, microbody.

In some embodiments, the antibody or antibody-like molecule is an IgG, IgA, IgM, IgE, monoclonal antibody, Fab', rIgG (half antibody), f(ab')$_2$, nanobody, affibody, anticalin, DARPin, monobody, avimer, microbody, chimeric antibody, scFv, scFv multimer, single domain antibody or single domain fusion antibody. In some embodiments, the antibody or antibody-like molecule is an IgG, Fab', rIgG (half antibody) or f(ab')$_2$. As used herein, f(ab')$_2$ is also referred to as Fab'$_2$ and variations thereof. In some preferred embodiments, the antibody or antibody-like molecule is an IgG or an antigen binding fragment thereof. In some preferred embodiments, the antibody or antibody-like molecule is a monoclonal antibody or an antigen binding fragment thereof. In some embodiments, the antibody or antibody-like molecule is a nanobody. A nanobody may also be referred to as a single-domain antibody (sdAb) or a VHH and contains one variable domain of a heavy-chain antibody (VHH), or of a common IgG.

Using antibodies in embodiments of the present disclosure provides a number of advantages. Firstly, all antibodies share a common three dimensional structure which is thought to reduce the need to optimise the geometry for each individual immunosensor. Secondly, antibodies have high specificity and affinity for their corresponding antigens and thirdly antibodies can be produced against virtually any antigen.

In some embodiments, antibodies and antibody-like molecules useful herein include engineered antibodies and antibody-like molecules. As used herein, an "engineered antibody or antibody-like molecule" refers to antibody or antibody-like molecule where one or more amino acids of the parent antibody or antibody-like molecule are substituted with a different amino acid. Such substitutions can be made by techniques known to the person skilled in the art, for example site directed mutagenesis. The different amino acid may be a naturally occurring amino acid (for example, a cysteine, lysine, glutamic acid, serine or tyrosine) or an unnaturally occurring amino acid. Unnaturally occurring amino acids can allow orthogonal chemical reactivity. In some embodiments, the unnaturally occurring amino acid carries an orthogonal functional group (such as azide or an alkyne) which can be used to site-specifically attach a first component of the CRET pair by post-translational modification. Examples of unnaturally occurring amino acids include, but are not limited to, 4-acetylphenylalanine, benzoylphenylalanine, acetyllysine, 4-azido-L-phenylalanine, azidohomoalanine, homopropargylglycine, strained cyclooctyne-lysine (SCO-Lys), trans-cyclooct-2-ene-lysine (TCO-Lys), 4-(6-methyl-s-tetrazin-3-yl)aminophenylalanine. Other suitable examples include any commercially available unnatural amino acid, such as those available from Jena Biosecience, Sigma Aldrich, Iris Biotech, Thermo Fisher and Base Click. The unnaturally occurring amino acid may be site-specifically incorporated into the antibody or antibody-like molecule by techniques known to the person skilled in the art, for example, amber codon suppression systems (Lang and Chin, 2014; Liu and Schultz, 2010). The unnatural amino acid can be useful for site-specific attachment of the first component of the CRET pair at the site of the unnatural amino acid through, for example, a click chemistry. In one example, the antibody or antibody-like molecule is a cysteine engineered antibody or antibody-like molecule, where one or more amino acids of a parent antibody are replaced with a free cysteine amino acid as disclosed in WO2006/034488. A cysteine engineered antibody comprises one or more free cysteine amino acids, preferably having a thiol reactivity value in the range of 0.6 to 1.0. A free cysteine amino acid is a cysteine residue which has been engineered into the parent antibody and is not part of a disulfide bridge. Cysteine engineered antibodies are useful for site-specific attachment of the first component of the CRET pair at the site of the engineered cysteine through, for example, a maleimide or haloacetyl. Engineered antibodies or antibody-like molecules preferably retain the antigen binding capability of their wild type, parent antibody counterparts. Thus, engineered antibodies or antigen-like molecules are capable of binding, preferably specifically, to antigens.

As used herein, the term "capable of binding" means that the antibody or antibody-like molecule is forms a complex with the antigen having a dissociation constant (KD) of 100 µM or less, 10 µM or less, 1 µM or less, 500 mM or less, 100 nM or less, 10 nM or less, 1 nM or less, 500 µM or less or 100 µM or less.

The antibody or antibody-like molecule useful in the present disclosure is capable of binding to an antigen and an analyte. As used herein, both the "antigen" and "analyte" are capable of binding to the same antibody or antibody-like molecule, preferably at the same binding site. Binding of the antigen and analyte to the antibody or antibody-like molecule is competitive, such that the antigen and analyte bind to the same or overlapping sites on the antibody or antibody-like molecule and only one of the antigen or analyte can bind at a time. In some embodiments, the antigen and analyte are identical other than the label. In other embodiments, the antigen is an antibody binding fragment of the analyte. In alternative embodiments, the analyte is an antibody binding fragment of the antigen.

In some embodiments, an antibody or antibody-like molecule useful in the present disclosure is an antibody or antibody-like molecule directed an antigen from a pathogen that triggers seroconversion.

In one example, the antibody or antibody-like molecule is a fusion protein comprising an antibody or antibody-like molecule and a first component of a CRET pair. For example, the antibody or antibody-like molecule is a fusion protein comprising an nanobody and a first component of a CRET pair (i.e. the nanobody and a first component of a CRET pair form part of the same polypeptide).

In alternative embodiments, the antibody or antibody-like molecule is not a fusion protein comprising an antibody or antibody-like molecule and a first component of a CRET pair. In one example, the antibody or antibody-like molecule is covalently attached to the first component of a CRET pair via a linker. Suitable linkers and attachment chemistry are as described herein. In another example, the antibody or antibody-like molecule is non-covalently attached to the first component of a CRET pair.

In some embodiments, there is provided an antibody or antibody-like molecule attached to a first component of a CRET pair and capable of binding to
i) an analyte; and
ii) a labelled antigen comprising an antigen capable of binding to the antibody or antibody-like molecule attached to a second component of a CRET pair, wherein when the labelled antigen is bound to the antibody or antibody-like molecule the efficiency of energy transfer between the first component and the second component is in the range of 10 to 75%. The antibody or antibody-like molecule, first component of a CRET pair, an analyte; and labelled antigen are as defined herein.

In some embodiments, there is provided a method of identifying an antibody or antibody-like molecule capable of binding to an analyte, the method comprising
i) obtaining two or more antibodies or antibody-like molecules which have different linkers which link the antibody or antibody-like molecule to a first component of a CRET pair,
ii) contacting the two or more antibodies or antibody-like molecules with a labelled antigen comprising an antigen capable of binding to the antibody or antibody-like molecule attached to a second component of the CRET pair,
iii) measuring the efficiency of energy transfer between the first component of the CRET pair and the second component of the CRET pair, and
iv) selecting at least one antibody or antibody-like molecule which, when bound to the labelled antigen, has an efficiency of energy transfer between the first component of the CRET pair and the second component of the CRET pair which is in the range of 10 to 75%. Preferably, step iv) comprises selecting the antibody or antibody-like molecule which, when bound to the labelled antigen, has the higher efficiency of energy transfer between the first component of the CRET pair and the second component of the CRET pair of the two or more antibodies or antibody-like molecules. In preferred examples, the efficiency of energy transfer between the first component of the CRET pair and the second component of the CRET pair of the selected antibody or antibody-like molecule, when bound to the labelled antigen, is in the range of 50 to 75%.

As used herein, the term "different linkers" comprises linkers of different length or linkers of different composition (for example, PEG based linkers versus peptide based linkers) or a combination thereof.

Labeled Antigen

The antibody or antibody-like molecule defined herein is capable of binding to a labelled antigen. As used herein, the term "antigen" refers to a molecule or portion of a molecule that can bind to a recognition site on an antibody or antibody-like molecule. As used herein, the term "labelled antigen" refers to an antigen attached to a second component of a CRET pair. The attachment can be a covalent attachment or a non-covalent attachment. The labelled antigen retains the ability to bind to a recognition site on an antibody or antibody-like molecule.

An antigen can be any compound or molecule of interest for which a diagnostic test is performed, such as a biopolymer or a small molecular bioactive material. An antigen can be, for example, a cell, a protein, peptide, carbohydrate, polysaccharide, glycoprotein, hormone, receptor, antibody, virus, substrate, metabolite, transition state analog, cofactor, inhibitor, drug, dye, nutrient, growth factor, nucleic acid or lipid, without limitation. In some embodiments, the antigen is selected from the group consisting of a small organic molecule, drug, drug metabolite, antibiotic, hormone, allergen, peptide, protein, naturally occurring antibody, sugar, lipid or nucleic acid. In some embodiments, the antigen is selected from the group consisting of a small organic molecule, drug, drug metabolite, antibiotic, hormone, allergen, peptide, protein, sugar, lipid or nucleic acid. In one example, the antigen is a peptide or protein. In another example, the antigen is an antibiotic, drug or drug metabolite. In another example, the antigen is an antibacterial. In another example, the antigen is an antifungal. In another example, the antigen is a synthetic antigen similar to or identical to an antigen from a pathogen that triggers seroconversion. In some embodiments, the antigen is a small organic molecule. As would be understood by the person skilled in the art, an antigen can fall under more than one category.

Preferably, the antigen is covalently attached to the second component of the CRET pair. In one example, the labelled antigen is a fusion protein comprising an antigen and a second component of a CRET pair, that is, both the antigen and the second component of a CRET pair form part of the same polypeptide. In some embodiments, the labelled antigen is a fusion protein comprising an antigen and a BRET acceptor domain. In some embodiments, the labelled antigen is a fusion protein comprising an antigen and a fluorescent acceptor domain. In one embodiment, the labelled antigen is a fusion protein comprising an antigen and GFP, preferably GFP$^2$. In some embodiments, the labelled antigen is a fusion protein comprising an antigen and a BRET donor domain. In some embodiments, the labelled antigen is a fusion protein comprising an antigen and a bioluminescent protein. In one example, the labelled antigen is a fusion protein comprising an antigen and RLuc8.

In another example, the labelled antigen is an antigen covalently attached to a second component of a CRET pair via a linker. Any suitable linker may be used. Non-limiting examples of linkers and attachment chemistry are as described herein.

In some embodiments, the labelled antigen is a small organic molecule covalently attached to a second component of a CRET pair via a linker. In some embodiments, the labelled antigen is a small organic molecule covalently attached to a second component of a BRET pair via a linker. In some embodiments, the labelled antigen is a small organic molecule attached to a fluorescent acceptor domain via a linker. In some embodiments, the labelled antigen is a small organic molecule covalently attached to a fluorescent protein, via a linker. In some embodiments, the labelled antigen is a small organic molecule covalently attached to GFP, for example GFP$^2$, via a linker. In some embodiments, the labelled antigen is a small organic molecule covalently attached to a BRET donor domain via a linker. In some embodiments, the labelled antigen is a small organic molecule covalently attached to a bioluminescent protein via a linker. In one example, the labelled antigen is a small organic molecule attached to RLuc8 via a linker. In alternative embodiments, the labelled antigen is a peptide or polypeptide covalently attached to a second component of a CRET pair via a linker. In some embodiments, the labelled antigen is a peptide or polypeptide covalently attached to a second component of a BRET pair via a linker. In some embodiments, the labelled antigen is a peptide or polypeptide attached to a fluorescent acceptor domain via a linker. In some embodiments, the labelled antigen is a peptide or polypeptide covalently attached to a fluorescent protein, via a linker. In some embodiments, the labelled antigen is a peptide or polypeptide covalently attached to GFP, for example GFP$^2$, via a linker. In some embodiments, the labelled antigen is a peptide or polypeptide covalently attached to a BRET donor domain via a linker. In some embodiments, the labelled antigen is a peptide or polypeptide covalently attached to a bioluminescent protein via a linker. In one example, the labelled antigen is a peptide or polypeptide covalently attached to RLuc8 via a linker.

In some embodiments, there is provided a method of identifying a labelled antigen, the method comprising
i) obtaining two or more labelled antigens, each labelled antigen comprising an antigen capable of binding an antibody or antibody-like molecule attached to a second component of a CRET pair via an optional linker; wherein the two or more labelled antigens comprise (i) different linkers; and/or (ii) different length antigen,
ii) contacting the two or more labelled antigens with an antibody or antibody-like molecule capable of binding to an analyte attached to a first component of the CRET pair,
iii) measuring the efficiency of energy transfer between the first component of the CRET pair and the second component of the CRET pair, and
iv) selecting at least one labelled antigen which, when bound the antibody or antibody-like molecule, has an efficiency of energy transfer between the first component of the CRET pair and the second component of the CRET pair which is in the range of 10 to 75%. Preferably, step iv) comprises selecting the antibody or antibody-like molecule which, when bound to the labelled antigen, has the higher efficiency of energy transfer between the first component of the CRET pair and the second component of the CRET pair of the two or more antibodies or antibody-like molecules. In preferred examples, the efficiency of energy transfer between the first component of the CRET pair and the second component of the CRET pair of the selected labelled antigen when bound to the antibody or antibody-like molecule is in the range of 50 to 75%.

As used herein, the phrase "different length antigen" refers to antigens of different molecular weight, size, number of amino acids. For example, the different length antigens may be polypeptides of different length containing the antibody or antibody-like molecule binding epitope.

As used herein, the phrase "different linkers" comprises linkers of different length or linkers of different composition (for example, PEG based linkers verses peptide based linkers) or a combination thereof.

Linker

As used herein, "linker" refers to a moiety that links one chemical species (for example, an antibody, antibody-like molecule or antigen) to another chemical species (for example, a first component or a second component of a CRET pair). A linker can be any biocompatible molecule that contains one or more reactive functional groups or groups that can be functionalised for attachment to one or more chemical species. In some embodiments, linkers join a reactive functional group or a first component of a CRET pair to an antibody or antibody-link molecule. In some embodiments, linkers join a reactive functional group or a second component of a CRET pair to an antigen. A linker can be any useful structure including, but not limited to, 0-order linkers (i.e., a bond), acyl, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. Further exemplary linkers include substituted or unsubstituted branched or linear C—C substituted or unsubstituted alkyl and substituted or unsubstituted heteroalkyl. Other linkers include nucleic acids, peptides and saccharides.

As used herein, "reactive functional group" has the meaning generally recognized in the art of synthetic chemistry, particularly bioconjugate chemistry. Exemplary reactive functional groups included, without limitation, olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptains, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids, thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Methods to prepare each of these functional groups are well-known in the art and their application to or modification for a particular purpose is within the ability of one of skill in the art (see, for example, Sandler and Karo, eds. ORGANIC FUNCTIONAL GROUP PREPARATIONS, Academic Press, San Diego, 1989).

Any suitable linker which achieves the above function may be utilized. Examples of suitable linkers include those comprising hydrocarbon chains (e.g. unbranched alkylene moieties), peptide chains, PEG-type or other polyether-type groups, and other polymeric groups (such as polyhydroxy-acids). In one example, the linker consists of a chain of atoms linking the two chemical species, the chain consisting of from 50 to 500, from 100 to 500, from 150 to 500, from 200 to 500, from 250 to 500, from 300 to 500, from 350 to 500, from 400 to 500 atoms. In one example, the linker consists of a chain of atoms linking the two chemical species, the chain consisting of from 2 to 500, 2 to 450, 2 to 400, 2 to 350, 2 to 300, 2 to 250, 2 to 200, 2 to 150, 2 to 100, 2 to 50, from 2 to 40, from 2 to 30, from 2 to 20, from 2 to 10 atoms.

In some embodiments, linkers include, but are not limited to, polypeptides, polynucleotides, polyalkylene glycol, polyalkylene glycol where at least one oxygen of the polyalkylene glycol chain is substituted with nitrogen, polyamine (Herve et al., 2008), peptide nucleic acid (PNA) (Egholm et al., 2005), locked nucleic acid (LNA) (Singh et al., 1998), triazoles, piperazines, oximes, thiazolidines, aromatic ring systems, alkanes, alkenes, alkynes, cyclic alkanes, cyclic alkenes, amides, thioamides, ethers, and hydrazones. In some embodiments, the linking element comprises or is selected from the group consisting of alkyl chain, glycol, polyglycol, ether, polyether, polyamide, polyester, amino acid, peptide, polypeptide or polynucleotide. In some embodiments, the linking element is a peptide or polypeptide. In some embodiments, the linking element is polyethylene glycol or polypropylene glycol.

In an example, the linker comprises hydrocarbons (e.g. the central spacer group may be an alkylene group), branched or unbranched, and said hydrocarbons being of chain length in the range of from $C_2$-$C_{250}$, $C_{20}$-$C_{250}$, $C_{40}$-$C_{250}$, $C_{60}$-$C_{250}$, $C_{80}$-$C_{250}$, $C_{100}$-$C_{250}$, $C_{120}$-$C_{250}$, $C_{140}$-$C_{250}$, $C_{160}$-$C_{250}$, $C_{180}$-$C_{250}$, $C_{200}$-$C_{250}$, $C_{220}$-$C_{250}$, or, at least $C_2$, at least $C_{20}$, at least $C_{40}$, at least $C_{50}$, at least $C_{60}$, at least $C_7O$, at least $C_{80}$, at least $C_{90}$, at least $C_{100}$. In an example, the linker comprises a branched or unbranched $C_{180}$-$C_{250}$, $C_{200}$-$C_{240}$, or $C_{210}$-$C_{230}$ hydrocarbon group. In an example, the linker comprises a branched or unbranched $C_{150}$-$C_{250}$, or $C_{180}$-$C_{220}$ hydrocarbon group. In some examples, the linker comprises a branched or unbranched $C_{180}$-$C_{220}$ hydrocarbon group. In some examples, the linker comprises a $C_1$, $C_2$, $C_3$, $C_4$, $C_5$, $C_6$, $C_7$, $C_8$, $C_9$, $C_{10}$, CU, $C_{14}$, $C_{16}$, $C_{18}$, or $C_{20}$ alkylene group, i.e. the linker comprises $(CH_2)_n$ where n is an integer between 1 and 20. In one example, the linker comprises a $C_2$ alkylene group (i.e. —$CH_2$—$CH_2$—).

In some embodiments, the linker can comprise polyalkylene glycol. Suitable polyalkylene glycols include polyethylene glycol (PEG), polypropylene glycol or methoxy-polyethylene glycol (mPEG) and derivatives thereof, such as for example O,O'-bis(2-aminopropyl)-polyethylene glycol 500 and 2,2'-(ethylene dioxide)diethyl amine. PEG is a polymer of ethylene glycol and, depending on substitutions, can have the chemical formula $C_{2n+2}H_{4n+6}O_{n+2}$. As referred to herein, a PEG group is a group base on the subunit —($CH_2CH_2O$)—, i.e. the term PEGn refers to a group of formula —($CH_2CH_2O$)$_n$—. In some embodiments, the linker may comprise PEGn, wherein n is the number of PEG units. For example, the linker comprises PEG having up to about 72 ethylene glycol moieties, up to about 60 ethylene glycol moieties, up to about 48 ethylene glycol moieties, up to about 36 ethylene glycol moieties, up to about 32 ethylene glycol moieties, up to about 28 ethylene glycol moieties, up to about 20 ethylene glycol moieties, up to about 12 ethylene glycol moieties, or up to about 8 ethylene glycol moieties. For example, the linker comprises PEG having 8 or more ethylene glycol moieties, 12 or more ethylene glycol moieties, 20 or more ethylene glycol moieties, 28 or more ethylene glycol moieties, 32 or more ethylene glycol moieties, 36 or more ethylene glycol moieties, 40 or more ethylene glycol moieties, 48 or more ethylene glycol moieties, 60 or more ethylene glycol moieties, or 70 or more ethylene glycol moieties. For example, the linker may comprise PEGn having a chain length of PEG2-PEG100, PEG10-PEG90, PEG20-PEG80, PEG30-PEG70, PEG40-PEG60, PEG45-PEG55, or, at least PEG2, at least PEG5, at least PEG10, at least PEG15, at least PEG20, at least PEG25, at least PEG30, at least PEG35, at least PEG40, at least PEG45, at least PEG50. Other useful polyalkylene glycols are polypropylene glycols, polybutylene glycols, PEG-glycidyl ethers, and PEG-oxycarbonylimidazole.

As would be understood by the person skilled in the art, the ethylene glycol moieties forming the linker do not have to form continuous stretch, that is, the PEG chain may be interrupted by one or more conjugation elements which link the PEG chains. For example, in some embodiments the linker comprises $PEG_n$-L-$PEG_m$, wherein m and n are independently an integer between 0 and 100 and L is a conjugation element. In some embodiments, n and m are independently selected from 4, 8, 12, 16, 20, 24, 28, 32, 36 or 40. As used herein, the term "conjugation element" refers to any chemical species formed by the reaction of two reactive functional groups. In some embodiments, the conjugation element is formed by the reaction of DBCO with an azide For example, in some embodiments the conjugation element is formed from the reaction of an azide containing molecule and a DBCO containing molecule.

In another example, the linker is a polyurethane, polyhydroxy acid, polycarbonate, polyimide, polyamide, polyester, polysulfone comprising 1-100, 1-90, 1-80, 1-70, 1-60, 10-60, 20-60, 30-60, 40-60, or, at least 4, at least 8, at least 12, at least 16, at least 20, at least 24, at least 28, at least 32, at least 36, at least 40, at least 44, at least 48, at least 52, at least 56, at least 60, or less than 60, less than 56, less than 52, less than 48, less than 44, less than 40, less than 36, less than 32, less than 28, less than 24, less than 20, less than 16, less than 12, less than 8, less than 4 monomer units.

In alternative embodiments, the linker comprises an oligonucleotide. The oligonucleotide can comprise both nucleoside bases or modified nucleoside bases or both. The linking element can have up to about 100 nucleoside bases and/or modified nucleoside bases. In one embodiment, the linking element can have up to about 100, up to about 90, up to about 80, up to about 70, up to about 60, up to about 50, up to about 40, up to about 30, up to about 20, up to about 10, up to about 5, or up to about 2 nucleoside bases and/or modified nucleoside bases. In some embodiments, the nucleic acid linker can have a length of 1-100, 20-80, 40-60, 45-55, or, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least. 35, at least 40, at least 45, at least 50, at least 55, at least 60, at least 65, at least 70, at least 75, at least 80, at least 85, at least 90, at least 95, at least 100 nucleoside bases and/or modified nucleoside bases.

In other embodiments, the linker comprises an amino acid or a chain of amino acids or peptides. For example, the linker may comprise a sequence of in the range of from 1-100, 20-80, 40-60, 45-55, or, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 35, at least 40, at least 45, at least 50, at least 55, at least 60, at least 65, at least 70, at least 75, at least 80, at least 85, at least 90, at least 95, at least 100 amino acid residues. In an example, the linker can comprise dipeptides, tripeptides, tetrapeptides, pentapeptides and so on. The amino acids can be naturally or unnaturally occurring amino acids or a combination thereof. The peptide or polypeptide can comprise modified amino acids.

In other examples, the linker can comprise amino acids selected from L-amino acids, D-amino acids or β-amino acids. In an example, the linker can comprise (3-peptides. In an example, the constituents of the amino acid linker are L amino acids. For example, the linker can comprise a Cys, a Thr, a Glu, a Gly, a Ser or a Lys amino acid residue. In an example, the linker comprises a Gly and a Ser. For example, the linker can comprise GlySerSer or GlySerSer repeats (GlySerSer)$_n$, For example, the linker can comprise (GlySerSer)$_n$ where n=1, n=2, n=3, n=4, n=5, n=6, n=7, n=8, n=9, n=10, n=11, n=12, n=13, n=14, n=15, n=16, n=17, n=18, n=19, n=20, n=21, n=22, n=23, n=24, n=25, n=26, n=27, n=28, n=29, n=30. In another example, the linker can comprise (GlySerSer)$_n$-X-(GlySerSer)$_m$, where n and m are independently 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 30 and X is a conjugation element, a Cys, a Thr, a Glu or a Lys.

In another example, the linker can comprise (GlySerSer)$_n$-XY-(GlySerSer)$_m$, where n and m are independently 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 and X is a conjugation element, a Cys, a Thr, a Glu or a Lys and Y is any amino acid. In another example, the linker can comprise (GlySerSer)$_n$-X (Y)$_a$-(GlySerSer)$_m$, where n and m are independently 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 and X is a conjugation element, a Cys, a Thr, a Glu or a Lys, Y is any amino acid or combination of amino acids and a is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40.

In an example, the linker can comprise GlySer or GlySer repeats ((GlySer)$_n$). For example, the linker can comprise (GlySer)$_n$ where n is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40. In another example, the linker can comprise (GlySer)$_n$-X$_a$-(GlySer)$_m$, where n and m are independently 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, X is a conjugation element, a Cys, a Thr, a Glu or a Lys, Y is any amino acid or combination of amino acids and a is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40.

In some embodiments, the linker comprises a high affinity Gln substrate for microbial transglutaminase (Oteng-Pabi et al., 2014). For example, the linking element comprises a peptide having the sequence selected from the group consisting of WALQRPH (SEQ ID NO: 1) and WELQRPY (SEQ ID NO: 2). In some embodiments, the linking element comprises a sortase recognition sequence (Theile et al., 2013). For example, the linking element comprises a peptide having the sequence LPXT, where X is any amino acid (SEQ ID NO: 3). As the person skilled in the art would understand, sortase mediated reactions can be used to label the N-terminus of the first or second component of the CRET pair. In some embodiments, the linker further comprises a spacer sequence. In some embodiments, the spacer sequence comprises one or more glycine, serine and/or threonine residues, for example, as defined above.

In an example, the linker can comprise molecules selected from the group consisting of thioxo-amino acids, hydroxy acids, mercapto acids, dicarbonic acids, diamines, dithioxocarbonic acids, acids and amines. In another example, the linker or tether comprises derivatised amino acid sequences or peptide nucleic acids (PNAs).

In an example, the linker is a combination of the above referenced components.

In an example, the antibody or antibody-like molecule is attached to the first component of the CRET pair via a peptide linker such that the antibody or antibody-like molecule and the first component of the CRET pair form a single polypeptide. In an example, the antigen is attached to the second component of the CRET pair via a peptide linker such that the antigen and the second component of the CRET pair form a single polypeptide.

Numerous methods for preparing the above referenced "linkers" and attaching them to a polypeptide, such as an antibody, antibody-like molecule, antigen, first or second component of a CRET pair, are known in the art and are suitable for use in the present disclosure. In an example, the antibody or antibody-like molecule is attached to the linker via a reactive functional group and the first component of the CRET pair is attached to the linker via a reactive functional group. In an example, the antigen is attached to the linker via a reactive functional group and the second component of the CRET pair is attached to the linker via a reactive functional group.

In some embodiments, the linker comprises one or more reactive functional groups. The reactive functional group can react with a chemical group in the antibody, antibody-like molecule, antigen, first component of the CRET pair or second component of the CRET pair by any means of chemical reaction to form the molecules described herein. The site of attachment to the antibody, antibody-like molecule, antigen, first component of the CRET pair or second component of the CRET pair includes primary amines (—NH$_2$), carboxyls (—COOH or CO), sulfhydryls (—SH), carbonyls (CHO) and carbohydrates. Any suitable reactive functional group may be used. In some embodiments, the reactive functional group is selected from the group consisting of a sulfhydryl reactive moiety, an amine reactive moiety and a carbonyl reactive moiety. In some embodiments, the reactive functional group is a group which reacts with a sulfhydryl reactive moiety, an amine reactive moiety and/or a carbonyl reactive moiety. For example, the reactive moiety may include of a free cysteine residue, free lysine residue or a carbonyl group.

For example, in some embodiments, the linker is provided with a sulfhydryl reactive moiety which is reactive with a free cysteine (e.g., a naturally occurring cysteine or a cysteine introduced by mutation) the antibody, antibody-like molecule, antigen, first component of the BRET pair or second component of the BRET pair to form a covalent linkage therebetween. In other embodiments, the linking element is provided with an amine reactive moiety which is reactive with a lysine residue (e.g., a naturally occurring lysine or a lysine introduced by mutation) in the antibody, antibody-like molecule, antigen, first component of the BRET pair or second component of the BRET pair to form a covalent linkage therebetween. In other embodiments, the linking element is provided with a carbonyl reactive moiety which is reactive with a carbonyl group in the antibody, antibody-like molecule, antigen, first component of the BRET pair or second component of the BRET pair to form a covalent linkage therebetween. In still another embodiment, the linking element is provided with a free cysteine or a free lysine which is reactive with a sulfhydryl reactive moiety in the antibody, antibody-like molecule, antigen, first component of the BRET pair or second component of the BRET pair to form a covalent linkage therebetween. In yet another embodiment, the linking element is provided with a free lysine which is reactive with an amine reactive moiety in the antibody, antibody-like molecule, antigen, first component of the BRET pair or second component of the BRET pair to form a covalent linkage therebetween. In another embodiment, the linking element is provided with a carbonyl group which is reactive with a carbonyl reactive moiety in the antibody, antibody-like molecule, antigen, first component of the BRET pair or second component of the BRET pair to form a covalent linkage therebetween.

Sulfhydryl reactive moieties include thiol, triflate, tresylate, aziridine, oxirane, S-pyridyl, haloacetyl (bromo- or iodo-), maleimidobenzoyl sulfosuccinimide ester, vinyl sulfone, pyridyldisulfide, thiosulfonate isocyanate and epoxide groups or maleimide moieties. Preferred sulfhydryl reactive moieties include maleimide, acrylamide, phenylcarbonylacrylamide and iodoacetamide. Amine reactive moieties include active esters (including, but not limited to, succinimidyl esters, sulfosuccinimidyl esters, tetrafluorophenyl esters, and sulfodichlorophenol esters), isothiocyanates, dichlorotriazines, aryl halides, acyl azides and sulfonyl chlorides. Of these amine reactive moieties, active esters are preferred reagents as they produce stable carboxamide bonds (see, for example, Banks and Paquette, 1995). Carbonyl reactive moieties include primary amines such as hydrazides and alkoxyamines. Carbonyl containing moieties include aldehydes (RCHO) and ketones (RCOR'). In some examples, the aldehyde is created by periodate-oxidation of a sugar group in the linking element. Examples of suitable reactive functional groups capable of reacting with an aldehyde group include amines, hydrazides and alkoxyamines.

Other examples of reactive functional groups include diazirines, aryl azides and isocyanates.

In one example, when the linker comprises PEG it may also comprise one or more reactive functional groups selected from the group consisting of maleimide (Mal), N-hydroxysuccinimide, dibenzocyclooctyne (DBCO) and azide which can be used to attach the PEG linker to the antibody, antibody-like molecule, antigen, first component of the CRET pair, second component of the CRET pair or additional linker. In one example, the linker comprises azido-(PEG)n-NHS ester, DBCO-(PEG)n-Mal, mal-(PEG)n-NHS or Mal-(PEG)n-Mal, where n is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40.

In one example, when the linker comprises a peptide it may also comprise a cysteine residue and/or a lysine residue.

In one example, the linker is functionalised and attached to a first or second component of a CRET pair using a carbodiimide compound (e.g. EDC). In one example, the linker is functionalised and attached to a first or second component of a CRET pair using a carbodiimide compound (e.g. EDC) in the presence of an N-hydroxysuccinimide compound (e.g. sulfo-NHS).

In another example, the linker can be functionalised and attached using various "click chemistry" strategies such as those disclosed in Kolb et al. (2001), WO 2003/101972 and Malkoch et al. (2005).

In another example, the linker can be functionalised and attached using Solulink bioconjugation chemistry (also referred to as Hydralink) (Dirksen et al., 2006). Briefly, Solulink bioconjugation chemistry is based on the reaction of an aromatic hydrazine with an aromatic aldehyde, to form a stable bis-arylhydrazone conjugate ion element as shown below:

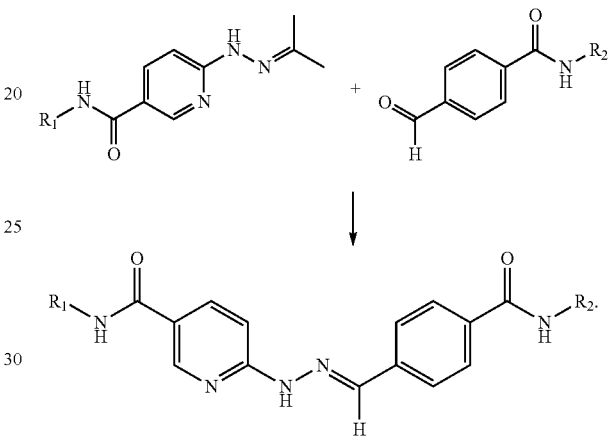

In another example, the linker comprises an aldehyde-aromatic hydrazine linker formed from the reaction of 4-formylbenzamide and 6-hydrazinonicotinamide.

In a further example, "linkers" can be attached via a transglutaminase reaction as discussed above. In a further example, "linkers" can be attached via a sortase reaction as discussed above.

In some examples, the antibody or antibody-like molecule is covalently attached to the first component of the CRET pair via a linker. In some embodiments, the linker (or part thereof) is an integral part of the antibody or antibody-like molecule (for example, a naturally occurring cysteine in the antibody or antibody-like molecule such that the antibody or antibody-like molecule and first component of the CRET pair are directly bound via the side-chain of the naturally occurring cysteine). In some embodiments, the linker (or part thereof) is an integral part of the first component of the CRET pair (for example, the side-chain of the naturally occurring cysteine, histidine, serine, tyrosine or lysine or enzyme recognition sequences, preferable a lysine or cysteine). In some embodiments the linker is a separate chemical entity which attaches the antibody or antibody-like molecule to the first component of the CRET pair.

In some embodiments, the molecules described herein (for example, the antibody or antibody-like molecule attached to the first component of the CRET pair or the antigen attached to the second component of the CRET pair) may comprise one or more linkers. For example, 1, 2, 3, 4, 5, 6, 7, 8, 9, 10 or 11 linkers. For example, an antibody or antibody-like molecule may have a first, a second, a third, a fourth or fifth linker for attaching the first component of the CRET pair. donor or acceptor domain. Preferably, the molecules described herein comprise one linker. In some embodiments, the number of linkers is dependent on the number of cysteine residues present in the hinge region of the antibody or fragment hereof.

In an example, the length of the linker attaching the first component of the CRET pair to the antibody or antibody-like molecule allows the first component of the CRET pair attached to the antibody or antibody-like molecule to be a suitable distance from the second component of the CRET pair when the antigen is bound to the antibody. A person skilled in the art would appreciate that the length of the linker can impact CRET (for example, BRET) between the first and second component of the CRET pair. Accordingly, the preferred length of the linker can vary depending on the selection of the first and second component of the CRET pair. The preferred length of the linker can be determined using methods defined herein and techniques known to the person skilled in the art.

In some examples, the antigen is covalently attached to the second component of the CRET pair via a linker. In some embodiments, the linker (or part thereof) is an integral part of the antigen (for example, a naturally occurring cysteine, lysine or sugar moiety). In some embodiments, the linker (or part thereof) is an integral part of the second component of the CRET pair (for example, the side-chain of the naturally occurring cysteine or lysine). In some embodiments the linker is a separate chemical moiety which attaches the antigen to the second component of the CRET pair.

In an example, the antibody, antibody-like molecule, antigen, first component of the CRET pair or second component of the CRET pair are functionalised for attachment to the linker. In other words, these molecules can be reacted with a chemical moiety which facilitates attachment of the antibody, antibody-like molecule, antigen, first component of the CRET pair or second component of the CRET pair to the linker. Methods of attaching a protein to a linker are well known in the art. See for example, Spicer & Davis (2014) and Boutureira & Bernardes (2015).

Site of Attachment

As would be understood by the person skilled in the art, the site of attachment for the antibody or antibody-like molecule to the first component of the CRET pair and the antigen to the second component of the CRET pair should not significantly interfere with the binding of the antigen to the antibody or antibody-like molecule. In some embodiments, the attachment of the first and/or second component of the CRET pair reduces binding of the antigen to the antibody or antibody-like molecule by less than 50%, less than 60%, less than 70%, less than 75%, less than 80%, less than 85%, less than 90% less than 95%, less than 98% or less than 99% when compared to binding of the antigen to the antibody or antibody-like molecule when not attached to the first and/or second component of the CRET pair. In other words, the labelled antigen is capable of binding to the antibody or antibody-like molecule attached to the first component of the CRET pair. In some embodiments, a complex consisting of the antibody or antibody-like molecule attached to the first component of the CRET pair forms and the labelled antigen has a dissociation constant (KD) of 100 µM or less, 10 µM or less, 1 µM or less, 500 mM or less, 100 nM or less, 10 nM or less, 1 nM or less, 500 µM or less or 100 µM or less. The attachment should also not significantly interfere with the activity of the first and/or second components of the CRET pair. In some embodiments, the attachment reduces the activity of the first and/or second component of the CRET pair by less than 50%, less than 60%, less than 70%, less than 75%, less than 80%, less than 85%, less than 90% less than 95%, less than 98% or less than 99% when compared to the activity of the first and/or second component of the CRET pair when not attached to the antigen, antibody or antibody-like molecule.

In some embodiments, the first component of the CRET pair is not attached to an antigen binding site of the antibody or antibody-like molecule. In some embodiments, the attachment between the antibody or antibody-like molecule and the first component of the CRET pair is site-specific. In some embodiments, the first component of the CRET pair is attached to a side-chain of a residue of the antibody or antibody-like molecule. The residue can be a cysteine, lysine, glutamic acid or aspartic acid. Preferably, the residue is a cysteine. In some embodiments, the cysteine is a naturally occurring cysteine, for example one present in the native sequence. In alternative embodiments, the cysteine is an engineered cysteine that is not present in the sequence of the native antibody or antibody-like molecule. In some embodiments, the cysteine is one that was involved in inter-chain disulphide bonds. Prior to attachment, the inter-chain disulphide bond is reduced by treatment with a reducing agent, for example, TCEP (tris(2-carboxyethyl)phosphine), DTT (dithiothreitol), MEA (2-mercaptoethlyamine, cysteamine) or 2-mercaptoethanol. Preferably, the reducing agent is a mild reducing agent, such as MEA or TCEP (see, for example, Kirley et al., 2016). The reaction conditions can be varied (for example, concentration of reducing agent, pH, temperature, reducing agent, time) to optimise the yield of the partially reduced antibody. In some embodiments, the partially reduced antibody or antibody-like molecule is subjected to mild oxidation, for example to promote reformation of disulphide bonds between cysteine residues located in close proximity. For example, in some embodiments, the partially reduced antibody is treated with dehydroascorbic acid (DHAA). In some embodiments, the residue is a cysteine in a hinge region of the antibody or antibody-like molecule or the residue is a cysteine involved in a heavy chain-light chain disulphide bond or a combination of both. In some embodiments, the antibody or antibody-like molecule is an antibody having a hinge region and the point of attachment is a cysteine in the hinge region of the antibody.

In some embodiments, the first component of the CRET pair is attached to N- or C-terminus of the antibody or antibody-like molecule. In an example, the attachment is via a peptide bond.

Antibodies or antibody-like molecules can be post translationally modified (for example, glycosylation). In some embodiments, the first component of the CRET pair is attached to the antibody or antibody-like molecule via the post-translational modification. For example, the first component of the CRET pair can be attached to the antibody or antibody-like molecule via a carbohydrate moiety refers to. As used herein, the term "carbohydrate moiety" includes saccharide, polysaccharide, oligosaccharide, and sugar the definitions of which are well known in the art of carbohydrate chemistry. Methods of attaching a polypeptide to a carbohydrate moiety of an antibody or antibody-like molecule are known to the person skilled in the art. Methods for attaching a polypeptide to a carbohydrate moiety of an antibody are described, for example, in U.S. Pat. No. 6,218, 160.

In some embodiments, the second component of the CRET pair is site-specifically attached to the antigen. In some embodiments, the second component of the CRET pair is attached to a side-chain of a residue of the antigen. The residue can be a cysteine, lysine, glutamic acid or aspartic acid. Preferably, the residue is a cysteine or a lysine. In some embodiments, the residue is a naturally occurring residue, for example one present in the native sequence of the polypeptide. In alternative embodiments, the residue is an engineered residue that is not present in the native sequence of the polypeptide. In some embodiments, the second component of the CRET pair is attached to N- or C-terminus of the antigen. In an example, the attachment is via a peptide bond. For example, the second component of the CRET pair and the antigen for a single polypeptide.

In some embodiments, the antigen is attached to a side-chain of a residue of the second component of the CRET pair. The residue can be a cysteine, lysine, glutamic acid or aspartic acid. Preferably, the residue is a cysteine or a lysine. In one example, the residue is a lysine. In some embodiments, the residue is a naturally occurring residue, for example one present in the native sequence of the polypeptide. In alternative embodiments, the residue is an engineered residue that is not present in the native sequence of the polypeptide.

Chemiluminescent Resonance Energy Transfer

Binding of an analyte to the antibody or antibody-like molecule of the present disclosure results in a reduction in the efficiency of energy transfer between the first and second components of the CRET pair. The reduction in the efficiency of energy transfer indicates that the analyte is present in the sample (see FIG. 1).

Chemiluminescence is the result of chemical reactions between an organic dye and an oxidizing agent in the presence of a catalyst. Chemiluminescence emission occurs as the energy from the excited states of organic dyes, which are chemically induced, decays to ground state. The duration and the intensity of the chemiluminescence emission are mostly dependent on the extent of the chemical reagents present in the reaction solution. The term "chemiluminescence" is used herein to encompass bioluminescence, which relies upon the activity of an enzyme. As used herein, chemiluminescent resonance energy transfer (CRET) is a proximity assay based on the non-radioactive transfer of energy between a chemiluminescent donor and an acceptor molecule. As used herein, bioluminescent resonance energy transfer (BRET) is a proximity assay based on the non-radioactive transfer of energy between a bioluminescent protein donor and an acceptor molecule.

A. Donor Domain

One of the first component or the second component of the CRET pair comprise a donor domain. In some embodiments, the first component of the CRET is a donor domain. In alternative embodiments, the second component of the CRET is a donor domain.

As used herein, the term "donor domain" means a molecule that emits light, for example a molecule which, when irradiated with light of a certain wavelength, emits light or a molecule which causes the emission of light as the result of a chemical reaction. The donor domain is capable of serving as a donor domain in a chemiluminescent resonance energy transfer pair (for example, in a BRET pair) and, depending on context, is also referred to herein as a "chemiluminescent resonance energy transfer donor domain" or "CRET donor domain". In preferred embodiments, the CRET pair is a BRET pair and the donor domain is referred to as a "bioluminescent resonance energy transfer donor domain" or "BRET donor domain".

Suitable donor domains include chemiluminescent domains which are capable of serving as a donor domain in a BRET pair. For example, the donor domain can be a chemiluminescent donor domain. In preferred embodiments, the chemiluminescent donor domain is a bioluminescent protein. As used herein, the term "bioluminescent protein" refers to any protein capable of acting on a suitable substrate to generate luminescence. It is understood in the art that a bioluminescent protein is an enzyme which converts a substrate into an activated product which then releases energy as it relaxes. The activated product (generated by the activity of the bioluminescent protein on the substrate) is the source of the bioluminescent protein-generated luminescence that is transferred to the acceptor molecule.

Any suitable bioluminescent protein can be used in the sensors of the present disclosure. There are a number of different bioluminescent proteins that can be employed in this invention (see, for example, Table 1). Light-emitting systems have been known and isolated from many luminescent organisms including bacteria, protozoa, coelenterates, molluscs, fish, millipedes, flies, fungi, worms, crustaceans, and beetles, particularly click beetles of genus *Pyrophorus* and the fireflies of the genera *Photinus, Photuris*, and *Luciola*. Additional organisms displaying bioluminescence are listed in WO 00/024878, WO 99/049019 and Viviani (2002).

TABLE 1

Exemplary bioluminescent proteins.

| Species | Name | Organism | MW kDa × $10^{-3}$ | Emission (nm) | Example of Substrate |
|---|---|---|---|---|---|
| Insect | FFluc | *Photinus pyralis* (North American Firefly) | ~61 | 560 | D-(−)-2-(6′-hydroxybenzothiazolyl)-$D^2$-thiazoline-4-carboxylic acid, HBTTCA ($C_{11}H_8N_2O_3S_2$) (luciferin) |
| Insect | FF'luc | *Luciola cruciata* (Japanese Firefly) | | 560-590 (many mutants) | Luciferin |
| Insect | | Phengodid beetles (railroad worms) | | | |
| Insect | | *Arachnocampa* spp. | | | Luciferin |
| Insect | | *Orphelia fultoni* (North American glow worm) | | | |
| Insect | Clluc | *Pyrophorus plagiophthalamus* (click beetle) | | 546, 560, 578 and 593 | Luciferin |

TABLE 1-continued

Exemplary bioluminescent proteins.

| Species | Name | Organism | MW kDa × $10^{-3}$ | Emission (nm) | Example of Substrate |
|---|---|---|---|---|---|
| Jellyfish | Aequorin | Aequorea | 44.9 | 460-470 | Coelenterazine |
| Sea pansy | RLuc | Renilla reniformis | 36 | 480 | Coelenterazine |
| Sea pansy (modified) | RLuc8 | Renilla reniformis (modified) | 36 | 487 (peak) | Coelenterazine/ Deep Blue C |
| Sea pansy (modified) | RLuc2 | Renilla reniformis (modified) M185V/Q235A) | 36 | 480 | Coelenterazine |
| Sea pansy (modified) | RLuc8.6-535 | Renilla reniformis (modified) | 36 | 535 | Coelenterazine |
| Sea pansy | RmLuc | Renilla mullerei | 36.1 | ~480 | Coelenterazine |
| Sea pansy | | Renilla kollikeri | | | |
| Crustacea (shrimp) | Vluc | Vargula hilgendorfii | ~62 | ~460 | Coelenterazine |
| Crustaeca | CLuc | Cypridina (sea firefly) | 75 | 465 | Coelenterazine/ Cypridina luciferin |
| Dinofagellate (marine alga) | | Gonyaulax polyedra | 130 | ~475 | Tetrapyrrole |
| Mollusc | | Latia (fresh water limpet) | 170 | 500 | Enol formate, terpene, aldehyde |
| Hydroid | | Obelia biscuspidata | ~20 | ~470 | Coelenterazine |
| Shrimp | | Oplophorus gracilorostris | 31 | 462 | Coelenterazine |
| Shrimp | | Oplophorus gracilorostris (NanoLuc) | 19 | ~460 | Furimazine |
| Others | Ptluc | Ptilosarcus | | ~490 | Coelenterazine |
| | Gluc | Gaussia | ~20 | ~475 | Coelenterazine |
| | Plluc | Pleuromamma | 22.6 | ~475 | Coelenterazine |

One very well-known example is the class of proteins known as luciferases which catalyse an energy-yielding chemical reaction in which a specific biochemical substance, a luciferin (a naturally occurring fluorophore), is oxidized by an enzyme having a luciferase activity (Hastings, 1996). A great diversity of organisms, both prokaryotic and eukaryotic, including species of bacteria, algae, fungi, insects, fish and other marine forms can emit light energy in this manner and each has specific luciferase activities and luciferins which are chemically distinct from those of other organisms. Luciferin/luciferase systems are very diverse in form, chemistry and function. Bioluminescent proteins with luciferase activity are thus available from a variety of sources or by a variety of means. Examples of bioluminescent proteins with luciferase activity may be found in U.S. Pat. Nos. 5,229,285, 5,219,737, 5,843,746, 5,196,524, and 5,670,356. Two of the most widely used luciferases are: (i) Renilla luciferase (from R. reniformis), a 35 kDa protein, which uses coelenterazine as a substrate and emits light at 480 nm (Lorenz et al., 1991); and (ii) Firefly luciferase (from Photinus pyralis), a 61 kDa protein, which uses luciferin as a substrate and emits light at 560 nm (de Wet et al., 1987).

Gaussia luciferase (from Gaussia princeps) has been used in biochemical assays (Verhaegen et al., 2002). Gaussia luciferase is a 20 kDa protein that oxidises coelenterazine in a rapid reaction resulting in a bright light emission at 470 nm.

Luciferases useful for the present invention have also been characterized from Anachnocampa sp (WO 2007/019634). These enzymes are about 59 kDa in size and are ATP-dependent luciferases that catalyse luminescence reactions with emission spectra within the blue portion of the spectrum.

Biologically active variants or fragments of naturally occurring bioluminescent protein can readily be produced by those skilled in the art. Three examples of such variants useful for the invention are RLuc2 (Loening et al., 2006), RLuc8 (Loening et al., 2006) and RLuc8.6-535 (Loening et al., 2007) which are each variants of Renilla luciferase. In a further preferred embodiment, the sequence of the donor domain is chosen to have greater thermal stability than molecules incorporating native Renilla luciferase. RLuc2 or RLuc8 are convenient examples of suitable choices, which consequently exhibit ≥5× or ≥10× higher luminance than sensors incorporating the native Renilla luciferase sequence. Such enhanced luminance has significant benefits as it permits more economical use of reagents for any given time resolution.

Alternative, non-luciferase, bioluminescent proteins that can be employed in this invention are any enzymes which can act on suitable substrates to generate a luminescent signal. Specific examples of such enzymes are β-galactosidase, lactamase, horseradish peroxidase, alkaline phosphatase, β-glucuronidase and β-glucosidase. Synthetic luminescent substrates for these enzymes are well known in the art and are commercially available from companies, such as Tropix Inc. (Bedford, MA, USA).

An example of a peroxidase useful for the present invention is described by Hushpulian et al., (2007).

In some embodiments, the bioluminescent protein is a luciferase, a β-galactosidase, a lactamase, a horseradish peroxidase, an alkaline phosphatase, a β-glucuronidase or a β-glucosidase. In some embodiments, the bioluminescent protein is luciferase. Suitable luciferase include, but are not limited to a Renilla luciferase, a Firefly luciferase (e.g. PpyRE8, PpyRE10), a Coelenterate luciferase, a North American glow worm luciferase, a click beetle luciferase, a railroad worm luciferase, a bacterial luciferase, a *Gaussia* luciferase, Aequorin, an *Arachnocampa* luciferase, an Oplophorus *gracilirostris* luciferase or a biologically active variant or fragment of any one, or chimera of two or more, thereof. In one example, the preferred luciferase is RLuc8 or a variant thereof.

As used herein, a "biologically active fragment" is a portion of a polypeptide as described herein which maintains a defined activity of the full-length polypeptide. As used herein, a "biologically active variant" is a molecule which differs from a naturally occurring and/or defined molecule by one or more amino acids but maintains a defined activity, such as defined above for biologically active fragments. Biologically active variants are typically least 50%, more preferably at least 80%, more preferably at least 90%, more preferably at least 95%, more preferably at least 97%, and even more preferably at least 99% identical to the naturally occurring and/or defined molecule.

In one embodiment, a bioluminescent protein with a small molecular weight is used to prevent an inhibition of the interaction due to steric hindrance. The bioluminescent protein preferably consists of a single polypeptide chain. Also the bioluminescent proteins preferably do not form oligomers or aggregates. The bioluminescent proteins *Renilla* luciferase, *Gaussia* luciferase and Firefly luciferase meet all or most of these criteria.

In some embodiments, the chemiluminescent donor domain is capable of modifying a substrate. As used herein, the term "substrate" refers to any molecule that can be used in conjunction with a chemiluminescent donor to generate or absorb luminescence. The choice of the substrate can impact on the wavelength and the intensity of the light generated by the chemiluminescent donor. In some embodiments, the bioluminescent protein has a substrate selected from luciferin, calcium, coelenterazine, furimazine or a derivative, analogue or stabilised derivative of coelenterazine, luciferin or furimazine.

Coelenterazine is a widely known substrate which occurs in cnidarians, copepods, chaetognaths, ctenophores, decapod shrimps, mysid shrimps, radiolarians and some fish taxa (Greer and Szalay, 2002). For *Renilla* luciferase for example, coelenterazine analogues/derivatives are available that result in light emission between 418 and 547 nm (Inouye et al., 1997, Loening et al., 2007). A coelenterazine analogue/derivative (400A, DeepBlueC) has been described emitting light at 400 nm with *Renilla* luciferase (WO 01/46691). Other examples of coelenterazine analogues/derivatives are EnduRen, Prolume purple, Prolume purple II, Prolume purple III, ViviRen and Furimazine. Other examples of coelenterazine analogues/derivatives include, but are not limited to, compounds disclosed in PCT/US2013057660 and US20140302539.

As used herein, the term "luciferin" is defined broadly and refers to a class of light-emitting biological pigments found in organisms capable of bioluminescence as well as synthetic analogues or functionally equivalent chemicals, which are oxidised in the presence of the enzyme luciferase to produce oxyluciferin and energy in the form of light. D-luciferin, or 2-(6-hydroxybenzothiazol-2-yl)-2-thiazoline-4-carboxylic acid, was first isolated from the firefly Photinus pyralis. Since then, various chemically distinct forms of luciferin have been discovered and studied from various different organisms, mainly from the ocean, for example fish and squid, however, many have been identified in land dwelling organisms, for example, worms, beetles and various other insects (Day et al., 2004; Viviani, 2002). As used herein, luciferin also includes derivatives or analogues of luciferin.

In addition to entirely synthetic luciferin, such as cyclic alkylaminoluciferin (CycLuc1), there are at least five general types of biologically evolved luciferin, which are each chemically different and catalysed by chemically and structurally different luciferases that employ a wide range of different cofactors. First, is firefly luciferin, the substrate of firefly luciferase, which requires ATP for catalysis (EC 1.13.12.7). Second, is bacterial luciferin, also found in some squid and fish, that consists of a long chain aldehyde and a reduced riboflavin phosphate. Bacterial luciferase is FMNH-dependent. Third, is dinoflagellate luciferin, a tetrapyrrolic chlorophyll derivative found in dinoflagellates (marine plankton), the organisms responsible for night-time ocean phosphorescence. Dinoflagellate luciferase catalyses the oxidation of dinoflagellate luciferin and consists of three identical and catalytically active domains. Fourth, is the imidazolopyrazine vargulin, which is found in certain ostracods and deep-sea fish, for example, Porichthys. Last, is coelenterazine (an imidazolpyrazine), the light-emitter of the protein Aequorin, found in radiolarians, ctenophores, cnidarians, squid, copepods, chaetognaths, fish and shrimp.

In some embodiments, the bioluminescent protein requires a co-factor. Examples of co-factors include, but are not necessarily limited to, ATP, magnesium, oxygen, $FMNH_2$, calcium, or a combination of any two or more thereof.

B. Acceptor Domain

One of the first component or the second component of the CRET pair comprise an acceptor domain. In some embodiments, the first component of the CRET is an acceptor domain. In alternative embodiments, the second component of the CRET is an acceptor domain.

The acceptor domain is capable of serving as an acceptor domain in a chemiluminescense resonance energy transfer pair (for example, in a BRET pair) and, depending on context, is also referred to herein as a "chemiluminescent resonance energy transfer acceptor domain" or "CRET acceptor domain". In preferred embodiments, the CRET pair is a BRET pair and the acceptor domain is referred to as a "bioluminescent resonance energy transfer donor domain" or "BRET donor domain". As used herein, an "acceptor domain" is any molecule that is capable of accepting energy emitted as a result of the activity of the donor domain. The acceptor domain can be a protein or non-protein acceptor domain.

In some embodiments, the acceptor domain (also referred to herein as "acceptor molecule") is a fluorescent acceptor domain. As used herein, the term "fluorescent acceptor domain" (also referred herein to as "fluorescent acceptor molecule") refers to any compound which can accept energy emitted as a result of the activity of a donor domain, and re-emit it as light energy. The fluorescent acceptor domain can be a protein or non-protein fluorescent acceptor domain.

There are a number of different acceptor domains that can be employed in this invention. In some embodiments, the acceptor domain is selected from the group consisting of protein, small organic molecule, rare earth element chelate and quantum dot. Preferred acceptor domains are proteins. In some embodiments, the acceptor domain is not a small organic molecule, rare earth element chelate or quantum dot. In some embodiments, the acceptor domain is not a small organic molecule. In some embodiments, the acceptor domain is not a rare earth element chelate. In some embodiments, the acceptor domain is not a quantum dot.

In some embodiments, the fluorescent acceptor domain is a fluorescent protein. One very well-known example is the group of fluorophores that includes the green fluorescent protein from the jellyfish *Aequorea victoria* and numerous other variants (GFPs) arising from the application of molecular biology, for example mutagenesis and chimeric protein technologies (Tsien, 1998). GFPs are classified based on the distinctive component of their chromophores, each class having distinct excitation and emission wavelengths: class 1, wild-type mixture of neutral phenol and anionic phenolate: class 2, phenolate anion: class 3, neutral phenol: class 4, phenolate anion with stacked s-electron system: class 5, indole: class 6, imidazole: and class 7, phenyl.

A naturally occurring acceptor molecule which has been mutated (variants) can also be useful for the present invention. One example of an engineered system which is suitable for BRET is a *Renilla* luciferase and enhanced yellow mutant of GFP (EYFP) pairing which do not directly interact to a significant degree with one another alone in the absence of a mediating protein(s) (in this case, the G protein coupled receptor) (Xu et al., 1999).

Examples include, but are not limited to, green fluorescent protein (GFP), blue fluorescent variant of GFP (BFP), cyan fluorescent variant of GFP (CFP), yellow fluorescent variant of GFP (YFP), enhanced GFP (EGFP), superfolder GFP, Azami green, mWasabi, TagGFP, Turbo GFP, AcGFP, ZsGreen, T-Sapphire, enhanced CFP (ECFP), CyPET, AmCyan1, Midori-Ishi green, TagCFP, mTFP1 (Teal), enhanced YFP (EYFP), GFPS65T, Emerald, Venus, mOrange, Topaz, mCitrine, YPet, TagYFP, PhiYFP, ZsYellow, mBanana, Kusabira Orange, Kusabira Orange2, mOrange, mOrange2, GFPuv, destabilised EGFP (dEGFP), destabilised ECFP (dECFP), destabilised EYFP (dEYFP), dKeima-Tandem, HcRed, HcRed-Tandem, t-HcRed, AQ143, DsRed, DsRed2, t-dimer2, tdimer2(12), mRFP1, mTangarine, pocilloporin, *Renilla* GFP, *Aequorea victoria* GFP, Monster GFP, paGFP, Kaede protein, tdTomato, mCherry, mRuby, mApple, mStrawberry, AsRed2, JRed, HcRedl, mRaspberry, mPlum, TagRFP, TurBoFP and Phycobiliproteins including R-Phycoerythrin (R-PE), B-Phycoerythrin (B-PE), C-Phycocyanin (CPC), Allophycocyanin (APC) and R-Phycocyanin (RPC) and a biologically active variant or fragment of any one thereof. In some embodiments, the preferred fluorescent acceptor domain is GFP. In some embodiments, the preferred fluorescent acceptor domain is $GFP^2$.

In alternative embodiments, the acceptor domain is a non-protein acceptor domain. In some embodiments, the non-protein acceptor domain can be a fluorescent acceptor domain or a quencher. As used herein, the term "quencher" refers to any compound which can accept energy emitted as a result of the activity of the donor domain, without re-emitting it as light energy. A non-fluorescent acceptor can be a quencher.

Any suitable non-protein fluorescent acceptor domain can be used. In some embodiments, the acceptor domain is selected from the group consisting of Alexa Fluor dye, Bodipy dye, Cy dye, fluorescein, dansyl, umbelliferone, Marina Blue, Cascade Blue, Cascade Yellow, Pacific Blue, Oregon Green, Tetramethylrhodamine, Rhodamine, coumarin, boron-dipyrromethene (BODIPY), resorufin, Texas Red, rare earth element chelates, or any combination or derivatives thereof. Examples of derivatives include, but are not limited to, amine reactive derivatives, aldehyde/ketone reactive derivatives, cytosine reactive or sulfhydryl reactive derivatives.

In some embodiments, the acceptor domain is fluorescein or a derivative thereof. Suitable derivatives include, but are not limited to, amine-reactive fluorescein derivatives, fluorescein isothiocyanate (FITC), NHS-fluorescein, NHS-LC-fluorescein, sulfhydryl-reactive fluorescein derivatives, 5-(and 6)-iodoacetamido-fluorescein, fluorescein-5-maleimide, fluorescein-6-maleimide, SAMSA-fluorescein, aldehyde/ketone and cytosine reactive fluorescein derivatives, fluorescein-5-thiosemicarbazide and 5-(((2-(carbohydrazine)methyl)thio) acetyl)-aminofluorescein. In some embodiments, R2 is a fluorescein-5-maleimide derivative. In some embodiments, the acceptor domain is rhodamine or a derivative thereof. Suitable derivatives include, but are not limited to, amine-reactive rhodamine derivatives, tetramethylrhodamine-5-(and 6)-isothiocyanate, NHS-rhodamine, Lissamine™ rhodamine B sulfonyl chloride, Lissamine™ rhodamine B sulfonyl hydrazine, sulphydryl-reactive rhodamine derivatives, tetramethylrhodamine-5-(and 6)-iodoacetamide, aldehyde/ketone and cytosine reactive rhodamine derivatives, Texas red hydrazine and texas red sulfonyl chloride. In some embodiments, R2 is coumarin or a derivative thereof. Suitable derivatives include, but are not limited to, amine-reactive coumarin derivatives, AMCA, AMCA-NHS, AMCA-sulfo-NHS, sulphydryl-reactive coumarin derivatives, AMCA-HPDP, DCIA, aldehyde and ketone reactive coumarin derivatives and AMCA-hydrazide. In some embodiments, the acceptor domain is boron-dipyrromethene (BODIPY) or a derivative thereof. Suitable derivatives include, but are not limited to, amine-reactive boron-dipyrromethene dyes, BODIPY FL C3-SE, BODIPY 530/550 C3, BODIPY 530/550 C3-SE, BODIPY 530/550 C3-hydrazide, BODIPY 493/503 C3-hydrazide, BODIPY FL C3-hydrazide, sulphydryl-reactive boron-dipyrromethene dyes, BODIPY FL 1A, BOPDIY 530/550 1A, Br-BOPDIPY 493/503 and aldehyde and ketone reactive boron-dipyrromethene dyes. In some embodiments, the acceptor domain is Cy (cyanine) dye or a derivative thereof. Suitable derivatives include, but are not limited to, amine reactive cyanine dyes, thiol-reactive cyanine dyes and carbonyl-reactive cyanine dyes.

In some embodiments, the acceptor domain is a quencher. Any suitable quencher can be used. In some embodiments, the acceptor domain is selected from the group consisting of DABCYL [4-((4-(Dimethylamino) phenyl)azo)benzoic acid], DABSYL (Dimethylaminoazosulfonic acid), metal nanoparticles such as gold and silver, black hole quenchers (BHQ), QSY dyes and QXL quenchers. In some embodiments, $R^2$ is selected from the group consisting of DABCYL [4-((4-(Dimethylamino) phenyl)azo)benzoic acid], DABSYL (Dimethylaminoazosulfonic acid), black hole quenchers (BHQ), QSY dyes and QXL quenchers.

In some embodiments, the acceptor domain is a quantum dot. Throughout the specification quantum dot and nanocrystal are used interchangeably. As used herein, a "quantum dot" is a semiconductor composed of atoms from groups II-VI or III-V elements of the periodic table (e.g., CdSe, CdTe and InP). Quantum dots of the same material, but with different sizes, can emit light of different colours. Their brightness is attributed to the quantization of energy levels due to confinement of an electron in all three spatial dimensions. In a bulk semiconductor, an electron-hole pair is bound within the Bohr exciton radius, which is characteristic for each type of semiconductor. A quantum dot is smaller than the Bohr exciton radius, which causes the appearance of discrete energy levels. The band gap, $\Delta E$, between the valance and conduction band of the semiconductor is a function of the nanocrystal's size and shape. Compared to traditional organic fluorophores, quantum dots have slightly lower luminescence quantum yields but much larger absorption cross-sections and very low rates of photobleaching. Molar extinction coefficients of quantum dots are about 105-106 M−1 cm−1, which is 10-100 times larger than dyes. As used herein, "quantum yield" refers to a measure of final emission of original energy donation.

Any quantum dot suitable for the purpose can be used. In some embodiments, the optical properties of quantum dots can be manipulated by synthesizing a shell. Typically, the shell is a stabilizing shell. Such quantum dots are known as core-shell quantum dots and include but are not limited to CdSe/ZnS, InP/ZnS, InP/CdSe. Core/shell quantum dots have higher band gap shells around their lower band gap cores, which emit light without any absorption by the shell. The shell passivates surface nonradiative emission from the core thereby enhancing the photoluminescence quantum yield and preventing natural degradation. The shell of type I quantum dots (such as, CdSe/ZnS) has a higher energy conduction band and a lower energy valance band than that of the core, resulting in confinement of both electron and hole in the core. The conduction and valance bands of the shell of type II quantum dots (such as CdTe/CdSe and CdSe/ZnTe) are either both lower or both higher in energy than those of the core. Thus, the motions of the electron and the hole are restricted to one dimension. Radiative recombination of the exciton at the core-shell interface gives rise to the type-II emission. Type II quantum dots behave as indirect semiconductors near band edges and therefore, have an absorption tail into the red and near infrared. Alloyed semiconductor quantum dots (CdSeTe) can also be used, although types I and II are preferred. The alloy composition and internal structure, which can be varied, permits tuning the optical properties without changing the particles' size.

In some embodiments, quantum dots are selected from the group consisting of CdSe/ZnS core/shell quantum dots, CdTe/CdSe core/shell quantum dots, CdSe/ZnTe core/shell quantum dots, and alloyed semiconductor quantum dots (e.g., CdSeTe).

If different colour emission is needed for creating multiple sensors (multiplex detection), this can be achieved by changing the size of the quantum dot core yielding different emission wavelengths. The quantum dots can be stabilized or unstabilized by techniques known to the person skilled in the art.

C. Donor Domain and Acceptor Domain Pairs (Cret Pairs)

Together the first component of the CRET pair and the second component of the CRET pair form a CRET pair. As used herein, "CRET pair" is used to refer to a group of molecules that participate in energy transfer. In some embodiments, the first component of the CRET pair comprises a BRET donor domain and second component of the CRET pair comprises a BRET acceptor domain. In alternative embodiments, the first component of the CRET pair comprises a BRET acceptor domain and second component of the CRET pair comprises a BRET donor domain. Any number of donor-acceptor combinations can be used. The donor-acceptor combination should be capable of serving as a CRET pair (for example, a BRET pair).

A worker skilled in the art would be able to select a donor and acceptor pair which permits efficient energy transfer. In preferred embodiments, the separation and relative orientation of the donor domain and the acceptor domain, when the labelled antigen is bound to the antibody or antibody-like domain, is within ±50% of the Förster distance. As used herein, the term "the separation and relative orientation of the donor domain and the acceptor domain, when the labelled antigen is bound to the antibody or antibody-like domain" refers to the steady state CRET measurements which can be carried out within a range of ±50% of Ro. This phrase encompasses an efficiency of luminescence energy transfer (also referred to herein as "efficiency of energy transfer") from the donor domain to the acceptor domain in the range of 10-90%. As used herein, the term "efficiency of energy transfer" means the fraction of energy that is non radiatively transferred from an excited state donor to a ground state acceptor per donor excitation event. In some embodiments, the efficiency of energy transfer between the first component of the CRET pair and the second component of the CRET pair is in the range of 10 to 75% when the labelled antigen is bound to the antibody or the antibody-like molecule. In some embodiments, the efficiency of energy transfer between the first component of the CRET pair and the second component of the CRET pair is in the range of 15 to 75%, 20 to 75%, 25 to 75%, 30 to 75%, 35 to 75%, 40 to 75%, 45 to 75%, 45 to 75%, 50 to 75%, 55 to 75%, 60 to 75%, 65% to 75% or 70 to 75% when the labelled antigen is bound to the antibody or the antibody-like molecule. In other embodiments, the efficiency of energy transfer between the first component of the CRET pair and the second component of the CRET pair is in the range of 10 to 70%, 10 to 65%, 10 to 60%, 10 to 55%, 10 to 50%, 10 to 45%, 10 to 40%, 10 to 35%, 10 to 30%, 10 to 25%, 10 to 20% or 10 to 15% when the labelled antigen is bound to the antibody or the antibody-like molecule.

In some embodiments, the Förster distance of the chemiluminescent donor domain and the acceptor domain is at least 4 nm, is at least 5.6 nm, or is at least 6 nm. In some embodiments, the Förster distance is less than 12 nm, less than 11 nm, less than 10 nm or less than 9 nm. In some embodiments, the Förster distance of the donor domain and the acceptor domain is between about 4 nm and about 11 nm, is between about 5.6 nm and about 11 nm or is between about 7 nm and about 11 nm. In some embodiments, the Förster distance of the CRET pair is between about 4 nm and about 18 nm, or is between about 6 nm and about 12 nm, or is between about 7.5 nm and 10.5 nm.

A criterion which should be considered in determining suitable pairings is the relative emission/fluorescence spectrum of the acceptor molecule compared to that of the donor. The emission spectrum of the donor should overlap with the absorbance spectrum of the acceptor molecule such that the light energy from the donor emission is at a wavelength that is able to excite the acceptor molecule and thereby promote acceptor molecule fluorescence when the two molecules are in a proper proximity and orientation with respect to one another. For example, it has been demonstrated that a *Renilla* luciferase/EGFP pairing is not as good as a *Renilla* luciferase/EYEF pairing based on observable emission spectral peaks (Xu et al., 1999; Wang et al., 1997 in Bioluminescence and Chemiluminescence: Molecular Reporting with Photons, eds. Hastings et al., (Wiley, New York), pp. 419-422). To study potential pairing, protein fusions (for example) are prepared containing the selected donor and acceptor domains and are tested, in the presence of an appropriate substrate if required.

It should also be confirmed that the donor and acceptor domains do not spuriously associate with each other. For example, this can be accomplished by separate co-expression of the first component of the CRET pair and the second component of the CRET pair in the same cells and then monitoring the luminescence spectrum in order to determine if energy transfer occurs. This may be achieved, for example, using the method of Xu et al. (1999). The selected first component of the CRET pair and the second component of the CRET pair form a suitable CRET pair if little or no CRET is observed.

In some embodiments, the donor emission can be manipulated by modifications to the substrate. In the case of *Renilla* luciferases the substrate is coelenterazine. The rationale behind altering the donor emission is to improve the resolution between donor emission and acceptor emissions. The original BRET system uses the *Renilla* luciferase as donor, EYFP (or Topaz) as the acceptor and coelenterazine h derivative as the substrate. These components when combined in a BRET assay, generate light in the 475-480 nm range for the bioluminescent protein and the 525-530 nm range for the acceptor molecule, giving a spectral resolution of 45-55 nm.

Unfortunately, *Renilla* luciferase generates a broad emission peak overlapping substantially the GFP emission, which in turn contributes to decrease the signal to noise of the system. One BRET system for use in the present invention has coel400a as the *Renilla* luciferase substrate and provides broad spectral resolution between donor and acceptor emission wavelengths (~105 nm). *Renilla* luciferase with coel400a generates light between 390-400 nm and a GFP derivative (GFP$^2$) was prepared which absorbs light in this range and re-emits light at 505-508 nm. Because of this increase in spectral resolution between *Renilla* luciferase and GFP emissions, this BRET system provides an excellent biological tool to monitor binding of a carbohydrate to the sensors of the present application. However, smaller Stokes shift BRET systems would also allow sensitive measurement of carbohydrates.

Various coelenterazine derivatives are known in the art, including coel400a, that generate light at various wavelengths (distinct from that generated by the wild type coelenterazine) as a result of *Renilla* luciferase activity. A worker skilled in the art would appreciate that because the light emission peak of the donor has changed, it is necessary to select an acceptor molecule which will absorb light at this wavelength and thereby permit efficient energy transfer. This can be done, for example by altering a GFP class 4 such that it becomes a class 3 or 1 GFP. Spectral overlapping between light emission of the donor and the light absorption peak of the acceptor is one condition among others for an efficient energy transfer. Class 3 and 1 GFPs are known to absorb light at 400 nm and re-emit between 505-511 nm. This results in a wavelength difference between donor and acceptor emissions of approximately 111 nm.

Examples of further bioluminescent protein and acceptor molecule pairs are provided in Table 2.

TABLE 2

Exemplary donor domain and acceptor domain pairs.

| Donor domain | Substrate | Substrate wavelength (peak) | Acceptor domain | Wavelength of acceptor (Ex/Em) |
|---|---|---|---|---|
| RLuc RLuc2 RLuc8 | Native coelenterazine | 470 nm | Venus | 515/528 nm |
| RLuc RLuc2 RLuc8 | Native coelenterazine | 470 nm | mOrange | 548/562 nm |
| RLuc RLuc2 RLuc8 | Native Coelenterazine | 470 nm | EYFP/Topaz | 514/527 nm |
| RLuc RLuc2 RLuc8 | Native Coelenterazine | 470 nm | mCitrine | 516/529 nm |
| RLuc RLuc2 RLuc8 | Native Coelenterazine | 470 nm | Ypet | 517/530 nm |
| RLuc RLuc2 RLuc8 | Native Coelenterazine | 470 nm | Superfolder GFP | 485/510 |
| RLuc RLuc2 RLuc8 | Native Coelenterazine | 470 nm | Azami Green | 492/505 |
| RLuc RLuc2 RLuc8 | Native Coelenterazine | 470 nm | mWasabi | 493/509 |
| RLuc RLuc2 RLuc8 | Native Coelenterazine | 470 nm | TagGFP | 482/505 |
| RLuc RLuc2 RLuc8 | Native Coelenterazine | 470 nm | TurboGFP | 482/502 |
| RLuc RLuc2 RLuc8 | Native Coelenterazine | 470 nm | AcGreen | 480/505 |
| RLuc RLuc2 RLuc8 | Native Coelenterazine | 470 nm | ZcGreen | 496/506 |
| RLuc RLuc2 RLuc8 | Native Coelenterazine | 470 nm | Enhanced CFP (eCFP) | 458/485 |
| RLuc RLuc2 RLuc8 | Native Coelenterazine | 470 nm | CyPET | 435/477 |

TABLE 2-continued

Exemplary donor domain and acceptor domain pairs.

| Donor domain | Substrate | Substrate wavelength (peak) | Acceptor domain | Wavelength of acceptor (Ex/Em) |
|---|---|---|---|---|
| RLuc RLuc2 RLuc8 | Native Coelenterazine | 470 nm | AmCyan1 | 453/486 |
| RLuc RLuc2 RLuc8 | Native Coelenterazine | 470 nm | Midori-Ishi | 472/495 |
| RLuc RLuc2 RLuc8 | Native Coelenterazine | 470 nm | TagCFP | 458/480 |
| RLuc RLuc2 RLuc8 | Native Coelenterazine | 470 nm | mTFP1(Teal) | 462/492 |
| RLuc RLuc2 RLuc8 | Native Coelenterazine | 470 nm | GFP565T | 490/510 |
| RLuc RLuc2 RLuc8 | Native Coelenterazine | 470 nm | Emerald | 487/510 |
| RLuc RLuc2 RLuc8 | Native Coelenterazine | 470 nm | Topaz | 514/527 |
| RLuc RLuc2 RLuc8 | Native Coelenterazine | 470 nm | TagYFP | 482/505 |
| RLuc RLuc2 RLuc8 | Native Coelenterazine | 470 nm | PhiYFP | 525/537 |
| RLuc RLuc2 RLuc8 | Native Coelenterazine | 470 nm | ZsYellow | 529/539 |
| RLuc RLuc2 RLuc8 | Native Coelenterazine | 470 nm | mBanana | 540/553 |
| RLuc RLuc2 RLuc8 | Native Coelenterazine | 470 nm | Kusabira Orange | 458/561 |
| RLuc RLuc2 RLuc8 | Native Coelenterazine | 470 nm | Kusabira Orange 2 | 551/565 |
| RLuc RLuc2 RLuc8 | Native Coelenterazine | 470 nm | mOrange 2 | 549/565 |
| RLuc RLuc2 RLuc8 | Native Coelenterazine | 470 nm | Fluorescein | 495/519 nm |
| RLuc RLuc2 RLuc8 | Native Coelenterazine | 470 nm | Acridine yellow | 470/550 nm |
| RLuc RLuc2 RLuc8 | Native Coelenterazine | 470 nm | Nile red | 485/525 nm |
| RLuc RLuc2 RLuc8 | Native Coelenterazine | 470 nm | R-Phycoerythrin | 480/578 nm |
| RLuc RLuc2 RLuc8 | Native Coelenterazine | 470 nm | Red 613 | 480/613 nm |
| RLuc RLuc2 RLuc8 | Native Coelenterazine | 470 nm | TruRed | 490/695 nm |
| RLuc8.6-5.35 | Native Coelenterazine | 535 nm | mOrange | 548/562 nm |
| RLuc8.6-5.35 | Coelenterazine h | 535 nm | TagRFP | 555/584 nm |
| RLuc8.6-5.35 | Coelenterazine h | 535 nm | TurboRFP | 588/635 nm |
| RLuc RLuc2 RLuc8 | Coelenterazine v | 515 nm | mOrange | 548/562 nm |
| RLuc RLuc2 RLuc8 | Coelenterazine v | 515 nm | TagRFP | 555/584 nm |
| RLuc8.6-5.35 | Coelenterazine v | 570 nm | TurboFP | 553/674 nm |
| RLuc8.6-5.35 | Coelenterazine v | 570 nm | Cyanine Cy3 | 575/605 nm |
| RLuc8.6-5.35 | Coelenterazine v | 570 nm | Texas red | 590/615 nm |
| RLuc8.6-5.35 | Coelenterazine v | 570 nm | TurboFP | 553/574 nm |

TABLE 2-continued

Exemplary donor domain and acceptor domain pairs.

| Donor domain | Substrate | Substrate wavelength (peak) | Acceptor domain | Wavelength of acceptor (Ex/Em) |
|---|---|---|---|---|
| RLuc8.6-5.35 | Coelenterazine v | 570 nm | tdTomato | 554/581 nm |
| RLuc8.6-5.35 | Coelenterazine v | 570 nm | TagRFP | 555/584 nm |
| RLuc8.6-5.35 | Coelenterazine v | 570 nm | DsRed | 557/592 nm |
| RLuc8.6-5.35 | Coelenterazine v | 570 nm | DsRed2 | 563/582 nm |
| RLuc8.6-5.35 | Coelenterazine v | 570 nm | DsRed2-Express | 553/584 nm |
| RLuc8.6-5.35 | Coelenterazine v | 570 nm | JRed | 584/610 nm |
| RLuc8.6-5.35 | Coelenterazine v | 570 nm | HcRed1 | 588/618 nm |
| RLuc8.6-5.35 | Coelenterazine v | 570 nm | HcRed-Tandem | 590/637 nm |
| RLuc8.6-5.35 | Coelenterazine v | 570 nm | mRFP1 | 584/607 nm |
| RLuc8.6-5.35 | Coelenterazine v | 570 nm | mTangerine | 568/585 nm |
| RLuc8.6-5.35 | Coelenterazine v | 570 nm | mRuby | 558/665 nm |
| RLuc8.6-5.35 | Coelenterazine v | 570 nm | mApple | 568/585 nm |
| RLuc8.6-5.35 | Coelenterazine v | 570 nm | mStrawberry | 574/596 nm |
| RLuc8.6-5.35 | Coelenterazine v | 570 nm | mRaspberry | 598/625 nm |
| RLuc8.6-5.35 | Coelenterazine v | 570 nm | mPlum | 590/649 nm |
| RLuc8.6-5.35 | Coelenterazine v | 570 nm | mCherry | 587/610 nm |
| RLuc8.6-5.35 | Coelenterazine v | 570 nm | AQ143 | 595/655 nm |
| RLuc8.6-5.35 | Coelenterazine v | 570 nm | tdTomato | 554/581 nm |
| RLuc8.6-5.35 | Coelenterazine v | 570 nm | AF680 | 679/702 nm |
| RLuc RLuc2 RLuc8 | Coelenterazine h | 470 nm | Venus | 515/528 nm |
| RLuc RLuc2 RLuc8 | Coelenterazine h | 470 nm | mOrange | 548/528 nm |
| RLuc RLuc2 RLuc8 | Coelenterazine h | 470 nm | EYFP/Topaz | 514/527 nm |
| RLuc RLuc2 RLuc8 | Coelenterazine h | 470 nm | mCitrine | 516/529 nm |
| RLuc RLuc2 RLuc8 | Coelenterazine h | 470 nm | Ypet | 517/530 nm |
| RLuc RLuc2 RLuc8 | Coelenterazine h | 470 nm | Superfolder GFP | 485/510 nm |
| RLuc RLuc2 RLuc8 | Coelenterazine h | 470 nm | Azami Green | 492/505 nm |
| RLuc RLuc2 RLuc8 | Coelenterazine h | 470 nm | mWasabi | 493/509 nm |
| RLuc RLuc2 RLuc8 | Coelenterazine h | 470 nm | TagGFP | 482/505 nm |
| RLuc RLuc2 RLuc8 | Coelenterazine h | 470 nm | TurboGFP | 482/502 nm |
| RLuc RLuc2 RLuc8 | Coelenterazine h | 470 nm | AcGreen | 480/505 nm |
| RLuc RLuc2 RLuc8 | Coelenterazine h | 470 nm | ZsGreen | 496/506 nm |
| RLuc RLuc2 RLuc8 | Coelenterazine h | 470 nm | Enhancd CFP (eCFP) | 458/485 nm |
| RLuc RLuc2 RLuc8 | Coelenterazine h | 470 nm | CyPET | 435/477 nm |
| RLuc RLuc2 RLuc8 | Coelenterazine h | 470 nm | AmCyan1 | 453/486 nm |
| RLuc RLuc2 RLuc8 | Coelenterazine h | 470 nm | Midori-Ishi | 472/495 nm |
| RLuc RLuc2 RLuc8 | Coelenterazine h | 470 nm | TagCFP | 458/480 nm |

TABLE 2-continued

Exemplary donor domain and acceptor domain pairs.

| Donor domain | Substrate | Substrate wavelength (peak) | Acceptor domain | Wavelength of acceptor (Ex/Em) |
|---|---|---|---|---|
| RLuc RLuc2 RLuc8 | Coelenterazine h | 470 nm | mTFP1(Teal) | 462/492 nm |
| RLuc RLuc2 RLuc8 | Coelenterazine h | 470 nm | GFP565T | 490/510 nm |
| RLuc RLuc2 RLuc8 | Coelenterazine h | 470 nm | Emerald | 487/510 nm |
| RLuc RLuc2 RLuc8 | Coelenterazine h | 470 nm | Topaz | 514/527 nm |
| RLuc RLuc2 RLuc8 | Coelenterazine h | 470 nm | TagYFP | 482/505 nm |
| RLuc RLuc2 RLuc8 | Coelenterazine h | 470 nm | PhiYFP | 525/537 nm |
| RLuc RLuc2 RLuc8 | Coelenterazine h | 470 nm | ZsYellow | 529/539 nm |
| RLuc RLuc2 RLuc8 | Coelenterazine h | 470 nm | mBanana | 540/553 nm |
| RLuc RLuc2 RLuc8 | Coelenterazine h | 470 nm | Kusabira Orange | 458/561 nm |
| RLuc RLuc2 RLuc8 | Coelenterazine h | 470 nm | Kusabira Orange 2 | 551/565 nm |
| RLuc RLuc2 RLuc8 | Coelenterazine h | 470 nm | mOrange 2 | 549/565 |
| RLuc RLuc2 RLuc8 | Coelenterazine h | 470 nm | Fluorescein | 490/525 nm |
| RLuc RLuc2 RLuc8 | Coelenterazine h | 470 nm | Acridine yellow | 470/550 nm |
| RLuc RLuc2 RLuc8 | Coelenterazine h | 470 nm | Nile red | 485/525 nm |
| RLuc RLuc2 RLuc8 | Coelenterazine h | 470 nm | R-Phycoerythrin | 480/578 nm |
| RLuc RLuc2 RLuc8 | Coelenterazine h | 470 nm | Red 613 | 480/613 nm |
| RLuc RLuc2 RLuc8 | Coelenterazine h | 470 nm | TruRed | 490/695 nm |
| RLuc8.6-5.35 | Coelenterazine h | 535 nm | mOrange | 548/562 nm |
| RLuc RLuc2 RLuc8 | Coelenterazine 400a | 400 nm | GFP$^2$ | 396/508 nm |
| RLuc RLuc2 RLuc8 | Coelenterazine 400a | 400 nm | GFP10 | 400/510 nm |
| RLuc RLuc2 RLuc8 | Coelenterazine 400a | 400 nm | Wild type GFP | 396 (475)/508 nm |
| RLuc RLuc2 RLuc8 | Coelenterazine 400a | 400 nm | *Renilla* GFP | 395/498 nm |
| RLuc RLuc2 RLuc8 | Coelenterazine 400a | 400 nm | T-Sapphire | 399/511 nm |
| RLuc RLuc2 RLuc8 | Coelenterazine 400a | 400 nm | GFPuv | 397/506 nm |
| RLuc RLuc2 RLuc8 | Coelenterazine 400a | 400 nm | TagBFP | 402/457 nm |

TABLE 2-continued

Exemplary donor domain and acceptor domain pairs.

| Donor domain | Substrate | Substrate wavelength (peak) | Acceptor domain | Wavelength of acceptor (Ex/Em) |
|---|---|---|---|---|
| RLuc RLuc2 RLuc8 | Coelenterazine 400a | 400 nm | eBFP | 383/445 nm |
| RLuc RLuc2 RLuc8 | Coelenterazine 400a | 400 nm | eBFP 2 | 383/440 nm |
| RLuc RLuc2 RLuc8 | Coelenterazine 400a | 400 nm | Azurite | 384/450 nm |
| RLuc RLuc2 RLuc8 | Coelenterazine 400a | 400 nm | mTagBFP | 399/456 nm |
| RLuc RLuc2 RLuc8 | Coelenterazine 400a | 400 nm | Cerulean/Mcfp | 433/475 nm |
| RLuc RLuc2 RLuc8 | Coelenterazine 400a | 400 nm | ECFP/CyPet | 434/477 nm |
| RLuc RLuc2 RLuc8 | Coelenterazine 400a | 400 nm | Y66W | 436/485 nm |
| RLuc RLuc2 RLuc8 | Coelenterazine 400a | 400 nm | dKeima-Red | 440/616 nm |
| RLuc RLuc2 RLuc8 | Coelenterazine 400a | 400 nm | dKeima-Tandem | 440/620 nm |
| RLuc RLuc2 RLuc8 | Coelenterazine 400a | 400 nm | mKeima-Red | 440/620 nm |
| RLuc RLuc2 RLuc8 | Coelenterazine 400a | 400 nm | Quin-2 | 365/490 nm |
| RLuc RLuc2 RLuc8 | Coelenterazine 400a | 400 nm | Pacific blue | 403/551 nm |
| RLuc RLuc2 RLuc8 | Coelenterazine 400 | 400 nm | Dansychloride | 380/475 nm |
| Firefly luciferase | Luciferin | 560 nm | Cyanine Cy3 | 575/605 nm |
| Firefly luciferase | Luciferin | 560 nm | Texas red | 590/615 nm |
| Firefly luciferase | Luciferin | 560 nm | TurboFP | 553/574 nm |
| Firefly luciferase | Luciferin | 560 nm | tdTomato | 554/581 nm |
| Firefly luciferase | Luciferin | 560 nm | TagRFP | 555/584 nm |
| Firefly luciferase | Luciferin | 560 nm | DsRed | 557/592 nm |
| Firefly luciferase | Luciferin | 560 nm | DsRed2 | 563/582 nm |
| Firefly luciferase | Luciferin | 560 nm | DsRed2-Express | 553/584 nm |
| Firefly luciferase | Luciferin | 560 nm | DsRed2-Express | 553/584 nm |
| Firefly luciferase | Luciferin | 560 nm | JRed | 584/610 nm |
| Firefly luciferase | Luciferin | 560 nm | HcRed1 | 588/618 nm |
| Firefly luciferase | Luciferin | 560 nm | HcRed-Tandem | 590/637 nm |
| Firefly luciferase | Luciferin | 560 nm | mRFP1 | 584/607 nm |
| Firefly luciferase | Luciferin | 560 nm | mTangerine | 568/585 nm |
| Firefly luciferase | Luciferin | 560 nm | mRuby | 558/605 nm |
| Firefly luciferase | Luciferin | 560 nm | mApple | 568/585 nm |
| Firefly luciferase | Luciferin | 560 nm | mStrawberry | 574/596 nm |
| Firefly luciferase | Luciferin | 560 nm | mRaspberry | 598/625 nm |
| Firefly luciferase | Luciferin | 560 nm | mPlum | 590/649 nm |
| Firefly luciferase | Luciferin | 560 nm | mCherry | 587/610 nm |
| Firefly luciferase | Luciferin | 560 nm | AQ143 | 595/655 nm |
| Beetle green luciferase | Luciferin | 560 nm | tdTomato | 554/581 nm |
| FFLuc PpyRE8 PpyRE10 | Luciferin | 560 nm | AF680 | 679/702 nm |
| FFLuc PpyRE8 PpyRE10 | Luciferin | 560 nm | AF750 | 749/775 nm |
| NanoLuc | Furimazine | 460 nm | Venus | 515/528 nm |
| NanoLuc | Furimazine | 460 nm | mOrange | 548/562 nm |
| NanoLuc | Furimazine | 460 nm | EYFP/Topaz | 514/527 nm |

TABLE 2-continued

Exemplary donor domain and acceptor domain pairs.

| Donor domain | Substrate | Substrate wavelength (peak) | Acceptor domain | Wavelength of acceptor (Ex/Em) |
|---|---|---|---|---|
| NanoLuc | Furimazine | 460 nm | mCitrine | 516/529 nm |
| NanoLuc | Furimazine | 460 nm | Ypet | 517/530 nm |
| NanoLuc | Furimazine | 460 nm | Superfolder GFP | 485/510 |
| NanoLuc | Furimazine | 460 nm | Azami Green | 492/505 nm |
| NanoLuc | Furimazine | 460 nm | mWasabi | 493/509 nm |
| NanoLuc | Furimazine | 460 nm | TagGFP | 482/505 nm |
| NanoLuc | Furimazine | 460 nm | TurboGFP | 482/502 nm |
| NanoLuc | Furimazine | 460 nm | AcGreen | 480/505 nm |
| NanoLuc | Furimazine | 460 nm | ZcGreen | 496/506 nm |
| NanoLuc | Furimazine | 460 nm | Enhancd CFP (eCFP) | 458/485 nm |
| NanoLuc | Furimazine | 460 nm | CyPET | 435/477 nm |
| NanoLuc | Furimazine | 460 nm | AmCyan1 | 453/486 nm |
| NanoLuc | Furimazine | 460 nm | Midori-Ishi | 472/495 nm |
| NanoLuc | Furimazine | 460 nm | TagCFP | 458/480 nm |
| NanoLuc | Furimazine | 460 nm | mTFP1(Teal) | 462/492 nm |
| NanoLuc | Furimazine | 460 nm | GFP565T | 490/510 nm |
| NanoLuc | Furimazine | 460 nm | Emerald | 487/510 nm |
| NanoLuc | Furimazine | 460 nm | Topaz | 514/527 nm |
| NanoLuc | Furimazine | 460 nm | TagYFP | 482/505 nm |
| NanoLuc | Furimazine | 460 nm | PhiYFP | 525/537 nm |
| NanoLuc | Furimazine | 460 nm | ZsYellow | 529/539 nm |
| NanoLuc | Furimazine | 460 nm | mBanana | 540/553 nm |
| NanoLuc | Furimazine | 460 nm | Kusabira Orange | 458/561 nm |
| NanoLuc | Furimazine | 460 nm | Kusabira Orange 2 | 551/565 nm |
| NanoLuc | Furimazine | 460 nm | mOrange 2 | 549/565 nm |
| NanoLuc | Furimazine | 460 nm | Fluorescein | 495/519 nm |
| NanoLuc | Furimazine | 460 nm | Acridine yellow | 470/550 nm |
| NanoLuc | Furimazine | 460 nm | Nile red | 485/525 nm |
| NanoLuc | Furimazine | 460 nm | R-Phycoerythrin | 480/487 nm |
| NanoLuc | Furimazine | 460 nm | Red 613 | 480/613 nm |
| NanoLuc | Furimazine | 460 nm | TruRed | 490/695 nm |
| NanoLuc | Furimazine | 460 nm | Oregon Green | 496/516 nm |
| NanoLuc | Furimazine | 460 nm | diAcFAM | 494/526 nm |
| NanoLuc | Furimazine | 460 nm | AlexFluor488 | 494/517 nm |
| NanoLuc | Furimazine | 460 nm | TMR | 555/585 nm |
| NanoLuc | Furimazine | 460 nm | Halotag NCT | 595/635 nm |
| NanoLuc | Furimazine | 460 nm | HalotagBRET 618 | 525/618 nm |
| NanoLuc | Native Coelenterazine | 460 nm | Venus | 515/528 nm |
| NanoLuc | Native Coelenterazine | 460 nm | mOrange | 548/562 nm |
| NanoLuc | Native Coelenterazine | 460 nm | EYFP/Topaz | 514/527 nm |
| NanoLuc | Native Coelenterazine | 460 nm | mCitrine | 516/529 nm |
| NanoLuc | Native Coelenterazine | 460 nm | Ypet | 517/530 nm |
| NanoLuc | Native Coelenterazine | 460 nm | Superfolder GFP | 485/510 nm |
| NanoLuc | Native Coelenterazine | 460 nm | Azami Green | 492/505 nm |
| NanoLuc | Native Coelenterazine | 460 nm | mWasabi | 493/509 nm |
| NanoLuc | Native Coelenterazine | 460 nm | TagGFP | 482/505 nm |
| NanoLuc | Native Coelenterazine | 460 nm | TurboGFP | 482/502 nm |
| NanoLuc | Native Coelenterazine | 460 nm | AcGreen | 480/505 nm |
| NanoLuc | Native Coelenterazine | 460 nm | ZcGreen | 496/506 nm |
| NanoLuc | Native Coelenterazine | 460 nm | Enhancd CFP (eCFP) | 458/485 nm |
| NanoLuc | Native Coelenterazine | 460 nm | CyPET | 435/477 nm |
| NanoLuc | Native Coelenterazine | 460 nm | AmCyan1 | 453/486 nm |

TABLE 2-continued

Exemplary donor domain and acceptor domain pairs.

| Donor domain | Substrate | Substrate wavelength (peak) | Acceptor domain | Wavelength of acceptor (Ex/Em) |
|---|---|---|---|---|
| NanoLuc | Native Coelenterazine | 460 nm | Midori-Ishi | 472/495 nm |
| NanoLuc | Native Coelenterazine | 460 nm | TagCFP | 458/480 nm |
| NanoLuc | Native Coelenterazine | 460 nm | mTFP1(Teal) | 462/492 nm |
| NanoLuc | Native Coelenterazine | 460 nm | GFP565T | 490/510 nm |
| NanoLuc | Native Coelenterazine | 460 nm | Emerald | 487/510 nm |
| NanoLuc | Native Coelenterazine | 460 nm | Topaz | 514/527 nm |
| NanoLuc | Native Coelenterazine | 460 nm | TagYFP | 482/505 nm |
| NanoLuc | Native Coelenterazine | 460 nm | PhiYFP | 525/537 nm |
| NanoLuc | Native Coelenterazine | 460 nm | ZsYellow | 529/539 nm |
| NanoLuc | Native Coelenterazine | 460 nm | mBanana | 540/553 nm |
| NanoLuc | Native Coelenterazine | 460 nm | Kusabira Orange | 458/561 nm |
| NanoLuc | Native Coelenterazine | 460 nm | Kusabira Orange 2 | 551/565 nm |
| NanoLuc | Native Coelenterazine | 460 nm | mOrange 2 | 549/565 nm |
| NanoLuc | Native Coelenterazine | 460 nm | Fluorescein | 495/519 nm |
| NanoLuc | Native Coelenterazine | 460 nm | Acridine yellow | 470/550 nm |
| NanoLuc | Native Coelenterazine | 460 nm | Nile red | 485/525 nm |
| NanoLuc | Native Coelenterazine | 460 nm | R-Phycoerythrin | 480/487 nm |
| NanoLuc | Native Coelenterazine | 460 nm | Red 613 | 480/613 nm |
| NanoLuc | Native Coelenterazine | 460 nm | TruRed | 490/695 nm |
| NanoLuc | Native Coelenterazine | 460 nm | Oregon Green | 496/516 nm |
| NanoLuc | Native Coelenterazine | 460 nm | diAcFAM | 494/526 nm |
| NanoLuc | Native Coelenterazine | 460 nm | AlexFluor488 | 494/517 nm |
| NanoLuc | Native Coelenterazine | 460 nm | TMR | 555/585 nm |
| NanoLuc | Native Coelenterazine | 460 nm | Halotag NCT | 595/635 nm |
| NanoLuc | Native Coelenterazine | 460 nm | HalotagBRET 618 | 525/618 |
| NanoLuc | Native Coelenterazine | 460 nm | Oregon Green | 496/516 nm |
| NanoLuc | Native Coelenterazine | 460 nm | diAcFAM | 494/526 nm |
| NanoLuc | Native Coelenterazine | 460 nm | AlexFluor488 | 494/517 nm |
| NanoLuc | Native Coelenterazine | 460 nm | TMR | 555/585 nm |
| NanoLuc | Native Coelenterazine | 460 nm | Halotag NCT | 595/635 nm |
| NanoLuc | Native Coelenterazine | 460 nm | HalotagBRET 618 | 525/618 |
| NanoLuc | Coelenterazine h | 460 nm | Venus | 515/528 nm |
| NanoLuc | Coelenterazine h | 460 nm | mOrange | 548/562 nm |
| NanoLuc | Coelenterazine h | 460 nm | EYFP/Topaz | 514/527 nm |
| NanoLuc | Coelenterazine h | 460 nm | mCitrine | 516/529 nm |
| NanoLuc | Coelenterazine h | 460 nm | Ypet | 517/530 nm |
| NanoLuc | Coelenterazine h | 460 nm | Superfolder GFP | 485/510 nm |

TABLE 2-continued

Exemplary donor domain and acceptor domain pairs.

| Donor domain | Substrate | Substrate wavelength (peak) | Acceptor domain | Wavelength of acceptor (Ex/Em) |
|---|---|---|---|---|
| NanoLuc | Coelenterazine h | 460 nm | Azami Green | 492/505 nm |
| NanoLuc | Coelenterazine h | 460 nm | mWasabi | 493/509 nm |
| NanoLuc | Coelenterazine h | 460 nm | TagGFP | 482/505 nm |
| NanoLuc | Coelenterazine h | 460 nm | TurboGFP | 482/502 nm |
| NanoLuc | Coelenterazine h | 460 nm | AcGreen | 480/505 nm |
| NanoLuc | Coelenterazine h | 460 nm | ZcGreen | 496/506 nm |
| NanoLuc | Coelenterazine h | 460 nm | Enhancd CFP (eCFP) | 458/485 nm |
| NanoLuc | Coelenterazine h | 460 nm | CyPET | 435/477 nm |
| NanoLuc | Coelenterazine h | 460 nm | AmCyan1 | 453/486 nm |
| NanoLuc | Coelenterazine h | 460 nm | Midori-Ishi | 472/495 nm |
| NanoLuc | Coelenterazine h | 460 nm | TagCFP | 458/480 nm |
| NanoLuc | Coelenterazine h | 460 nm | mTFP1(Teal) | 462/492 nm |
| NanoLuc | Coelenterazine h | 460 nm | GFP565T | 490/510 nm |
| NanoLuc | Coelenterazine h | 460 nm | Emerald | 487/510 nm |
| NanoLuc | Coelenterazine h | 460 nm | Topaz | 514/527 nm |
| NanoLuc | Coelenterazine h | 460 nm | TagYFP | 482/505 nm |
| NanoLuc | Coelenterazine h | 460 nm | PhiYFP | 525/537 nm |
| NanoLuc | Coelenterazine h | 460 nm | ZsYellow | 529/539 nm |
| NanoLuc | Coelenterazine h | 460 nm | mBanana | 540/553 nm |
| NanoLuc | Coelenterazine h | 460 nm | Kusabira Orange | 458/561 nm |
| NanoLuc | Coelenterazine h | 460 nm | Kusabira Orange 2 | 551/565 nm |
| NanoLuc | Coelenterazine h | 460 nm | mOrange 2 | 549/565 nm |
| NanoLuc | Coelenterazine h | 460 nm | Fluorescein | 495/519 nm |
| NanoLuc | Coelenterazine h | 460 nm | Acridine yellow | 470/550 nm |
| NanoLuc | Coelenterazine h | 460 nm | Nile red | 485/525 nm |
| NanoLuc | Coelenterazine h | 460 nm | R-Phycoerythrin | 480/487 nm |
| NanoLuc | Coelenterazine h | 460 nm | Red 613 | 480/613 nm |
| NanoLuc | Coelenterazine h | 460 nm | TruRed | 490/695 nm |
| NanoLuc | Coelenterazine h | 460 nm | Oregon Green | 496/516 nm |
| NanoLuc | Coelenterazine h | 460 nm | diAcFAM | 494/526 nm |
| NanoLuc | Coelenterazine h | 460 nm | AlexFluor488 | 494/517 nm |
| NanoLuc | Coelenterazine h | 460 nm | TMR | 555/585 nm |
| NanoLuc | Coelenterazine h | 460 nm | Halotag NCT | 595/635 nm |
| NanoLuc | Coelenterazine h | 460 nm | HalotagBRET 618 | 525/618 |
| NanoLuc | Coelenterazine 400a | 400 nm | GFP$^2$ | 396/508 nm |
| NanoLuc | Coelenterazine 400a | 400 nm | GFP10 | 400/510 nm |
| NanoLuc | Coelenterazine 400a | 400 nm | Wild type GFP | 396 (475)/508 nm |

TABLE 2-continued

Exemplary donor domain and acceptor domain pairs.

| Donor domain | Substrate | Substrate wavelength (peak) | Acceptor domain | Wavelength of acceptor (Ex/Em) |
|---|---|---|---|---|
| NanoLuc | Coelenterazine 400a | 400 nm | TagBFP | 402/457 nm |
| NanoLuc | Coelenterazine 400a | 400 nm | eBFP | 383/445 nm |
| NanoLuc | Coelenterazine 400a | 400 nm | eBFP 2 | 383/440 nm |
| NanoLuc | Coelenterazine 400a | 400 nm | Azurite | 384/450 nm |
| NanoLuc | Coelenterazine 400a | 400 nm | mTagBFP | 399/456 nm |
| NanoLuc | Coelenterazine 400a | 400 nm | Cerulean/Mcfp | 433/475 nm |
| NanoLuc | Coelenterazine 400a | 400 nm | ECFP/CyPet | 434/477 nm |
| NanoLuc | Coelenterazine 400a | 400 nm | Y66W | 436/485 nm |
| NanoLuc | Coelenterazine 400a | 400 nm | dKeima-Red | 440/616 nm |
| NanoLuc | Coelenterazine 400a | 400 nm | mKeima-Red | 440/620 nm |
| NanoLuc | Coelenterazine 400a | 400 nm | Quin-2 | 365/490 nm |
| NanoLuc | Coelenterazine 400a | 400 nm | Pacific blue | 403/551 nm |
| NanoLuc | Coelenterazine 400a | 400 nm | Dansychloride | 380/475 nm |
| NanoLuc | Coelenterazine 400a | 400 nm | T-Sapphire | 399/511 nm |
| NanoLuc | Coelenterazine 400a | 400 nm | GFPuv | 397/506 nm |
| RLuc RLuc2 RLuc8 NanoLuc | Prolume Purple Substrate | 405 nm | GFP$^2$ | 396/508 nm |
| RLuc RLuc2 RLuc8 NanoLuc | Prolume Purple Substrate | 405 nm | GFP10 | 400/510 nm |
| RLuc RLuc2 RLuc8 NanoLuc | Prolume Purple Substrate | 405 nm | Wild type GFP | 396 (475)/508 nm |
| RLuc RLuc2 RLuc8 NanoLuc | Prolume Purple Substrate | 405 nm | TagBFP | 402/457 nm |
| RLuc RLuc2 RLuc8 NanoLuc | Prolume Purple Substrate | 405 nm | Cerulean/Mcfp | 433/475 nm |
| RLuc RLuc2 RLuc8 NanoLuc | Prolume Purple Substrate | 405 nm | ECFP/CyPet | 434/477 nm |
| RLuc RLuc2 RLuc8 NanoLuc | Prolume Purple Substrate | 405 nm | Y66W | 436/485 nm |
| RLuc RLuc2 RLuc8 NanoLuc | Prolume Purple Substrate | 405 nm | dKeima-Red | 440/616 nm |
| RLuc RLuc2 RLuc8 NanoLuc | Prolume Purple Substrate | 405 nm | mKeima-Red | 440/620 nm |
| RLuc RLuc2 RLuc8 NanoLuc | Prolume Purple Substrate | 405 nm | Quin-2 | 365/490 nm |
| RLuc RLuc2 RLuc8 NanoLuc | Prolume Purple Substrate | 405 nm | Pacific blue | 403/551 nm |

TABLE 2-continued

Exemplary donor domain and acceptor domain pairs.

| Donor domain | Substrate | Substrate wavelength (peak) | Acceptor domain | Wavelength of acceptor (Ex/Em) |
|---|---|---|---|---|
| RLuc RLuc2 RLuc8 NanoLuc | Prolume Purple Substrate | 405 nm | Dansychloride | 380/475 nm |
| RLuc RLuc2 RLuc8 NanoLuc | Prolume Purple Substrate II | 400 nm | GFP$^2$ | 396/508 nm |
| RLuc RLuc2 RLuc8 NanoLuc | Prolume Purple Substrate II | 400 nm | GFP10 | 400/510 nm |
| RLuc RLuc2 RLuc8 NanoLuc | Prolume Purple Substrate II | 400 nm | Wild type GFP | 396 (475)/508 nm |
| RLuc RLuc2 RLuc8 NanoLuc | Prolume Purple Substrate II | 400 nm | TagBFP | 402/457 nm |
| RLuc RLuc2 RLuc8 NanoLuc | Prolume Purple Substrate II | 400 nm | Cerulean/Mcfp | 433/475 nm |
| RLuc RLuc2 RLuc8 NanoLuc | Prolume Purple Substrate II | 400 nm | ECFP/CyPet | 434/477 nm |
| RLuc RLuc2 RLuc8 NanoLuc | Prolume Purple Substrate II | 400 nm | Y66W | 436/485 nm |
| RLuc RLuc2 RLuc8 NanoLuc | Prolume Purple Substrate II | 400 nm | dKeima-Red | 440/616 nm |
| RLuc RLuc2 RLuc8 NanoLuc | Prolume Purple Substrate II | 400 nm | mKeima-Red | 440/620 nm |
| RLuc RLuc2 RLuc8 NanoLuc | Prolume Purple Substrate II | 400 nm | Quin-2 | 365/490 nm |
| RLuc RLuc2 RLuc8 NanoLuc | Prolume Purple Substrate II | 400 nm | Pacific blue | 403/551 nm |
| RLuc RLuc2 RLuc8 NanoLuc | Prolume Purple Substrate II | 400 nm | Dansychloride | 380/475 nm |
| RLuc RLuc2 RLuc8 NanoLuc | Prolume Purple Substrate III | 410 nm | GFP$^2$ | 396/508 nm |
| RLuc RLuc2 RLuc8 NanoLuc | Prolume Purple Substrate III | 410 nm | GFP10 | 400/510 nm |
| RLuc RLuc2 RLuc8 NanoLuc | Prolume Purple Substrate III | 410 nm | Wild type GFP | 396 (475)/508 nm |
| RLuc RLuc2 RLuc8 NanoLuc | Prolume Purple Substrate III | 410 nm | TagBFP | 402/457 nm |
| RLuc RLuc2 RLuc8 NanoLuc | Prolume Purple Substrate III | 410 nm | Cerulean/Mcfp | 433/475 nm |

TABLE 2-continued

Exemplary donor domain and acceptor domain pairs.

| Donor domain | Substrate | Substrate wavelength (peak) | Acceptor domain | Wavelength of acceptor (Ex/Em) |
|---|---|---|---|---|
| RLuc RLuc2 RLuc8 NanoLuc | Prolume Purple Substrate III | 410 nm | ECFP/CyPet | 434/477 nm |
| RLuc RLuc2 RLuc8 NanoLuc | Prolume Purple Substrate III | 410 nm | Y66W | 436/485 nm |
| RLuc RLuc2 RLuc8 NanoLuc | Prolume Purple Substrate III | 410 nm | dKeima-Red | 440/616 nm |
| RLuc RLuc2 RLuc8 NanoLuc | Prolume Purple Substrate III | 410 nm | mKeima-Red | 440/620 nm |
| RLuc RLuc2 RLuc8 NanoLuc | Prolume Purple Substrate III | 410 nm | Quin-2 | 365/490 nm |
| RLuc RLuc2 RLuc8 NanoLuc | Prolume Purple Substrate III | 410 nm | Pacific blue | 403/551 nm |
| RLuc RLuc2 RLuc8 NanoLuc | Prolume Purple Substrate III | 410 nm | Dansychloride | 380/475 nm |

In some embodiments, there is provided a CRET pair (also referred to herein as an immunosensor) comprising:
an antibody or antibody-like molecule capable of binding to an analyte attached to a first component of a CRET pair; and
a labelled antigen comprising an antigen capable of binding to the antibody or antibody-like molecule attached to a second component of a CRET pair;
wherein when the labelled antigen is bound to the antibody or antibody-like molecule the efficiency of energy transfer between the first component of the CRET pair and the second component of the CRET pair is in the range of 10 to 75%. The components of the CRET pair are as defined herein.

In some embodiments, the preferred CRET pair comprises RLuc8 and GFP$^2$. In one example, the antibody or antibody-like molecule is attached to RLuc8 and the labelled antigen is attached to GFP$^2$. In another example, the antibody or antibody-like molecule is attached to GFP$^2$ and the labelled antigen is attached to RLuc8.

Detecting an Analyte

As illustrated in FIG. 1, in the absence of analyte, the labelled antigen is able to bind to the antibody or antibody-like molecule bringing the first and second component of the CRET pair together resulting in CRET between the two components in the presence of a substrate. In the presence of analyte, the analyte competes with the labelled antigen for binding to the antibody or antibody-like molecule resulting in a reduction in CRET between the two components in the presence of a substrate. In other words, binding of an analyte to the antibody or antibody-like molecule of the present disclosure alters the spatial location and/or dipole orientation of the first component of the CRET pair relative to the second component of the CRET pair. As used herein, the term "spatial location" refers to the three dimensional positioning of the donor relative to the acceptor molecule which changes as a result of the analyte binding or releasing from the antibody or antibody-like molecule.

As used herein, the term "dipole orientation" refers to the direction in three-dimensional space of the dipole moment associated either with the donor and/or the acceptor molecule relative their orientation in three-dimensional space. The dipole moment is a consequence of a variation in electrical charge over a molecule.

The efficiency of energy transfer can be determined ratiometrically (for example, CRET ratio, preferably BRET ratio). Using BRET as an example, in some embodiments, binding of an analyte to the antibody or antibody-like molecule of the present disclosure is indicated by a reduction in the BRET ratio. In other words, a reduction in the efficiency of energy transfer between the first and second components of the CRET pair is indicated by a reduction in the BRET ratio.

In an embodiment the energy transfer occurring between the first component of the CRET pair (for example, a bioluminescent protein) and the second component of a CRET pair (for example, an acceptor molecule) is presented as calculated ratios from the emissions measured using optical filters (one for the acceptor molecule emission and the other for the bioluminescent protein emission) that select specific wavelengths (see equation 1).

$$E_a/E_d = \text{BRET ratio} \quad (1)$$

where $E_a$ is defined as the acceptor molecule emission intensity (emission light is selected using a specific filter adapted for the emission of the acceptor) and $E_d$ is defined as the bioluminescent protein emission intensity (emission light is selected using a specific filter adapted for the emission of the bioluminescent protein).

It should be readily appreciated by those skilled in the art that the optical filters may be any type of filter that permits wavelength discrimination suitable for BRET. For example, optical filters used in accordance with the present invention can be interference filters, long pass filters, short pass filters, etc. Intensities (usually in counts per second (CPS) or relative luminescence units (RLU)) of the wavelengths passing through filters can be quantified using either a photo-multiplier tube (PMT), photodiode, including a cascade photodiode, photodiode array or a sensitive camera such as a charge coupled device (CCD) camera. The quantified signals are subsequently used to calculate BRET ratios and represent energy transfer efficiency. The BRET ratio increases with increasing intensity of the acceptor emission.

Generally, a ratio of the acceptor emission intensity over the donor emission intensity is determined (see equation 1), which is a number expressed in arbitrary units that reflects energy transfer efficiency. The ratio increases with an increase of energy transfer efficiency (see Xu et al., 1999).

Energy transfer efficiencies can also be represented using the inverse ratio of donor emission intensity over acceptor emission intensity (see equation 2). In this case, ratios decrease with increasing energy transfer efficiency. Prior to performing this calculation the emission intensities are corrected for the presence of background light and autoluminescence of the substrate. This correction is generally made by subtracting the emission intensity, measured at the appropriate wavelength, from a control sample containing the substrate but no bioluminescent protein, acceptor molecule or polypeptide of the invention.

$$E_d/E_a = \text{BRET ratio} \tag{2}$$

where $E_a$ and $E_d$ are as defined above.

The light intensity of the bioluminescent protein and acceptor molecule emission can also be quantified using a monochromator-based instrument such as a spectrofluorometer, a charged coupled device (CCD) camera or a diode array detector. Using a spectrofluorometer, the emission scan is performed such that both bioluminescent protein and acceptor molecule emission peaks are detected upon addition of the substrate. The areas under the peaks represent the relative light intensities and are used to calculate the ratios, as outlined above. Any instrument capable of measuring lights for the bioluminescent protein and acceptor molecule from the same sample, can be used to monitor the BRET system of the present invention.

In an alternative embodiment, the acceptor molecule emission alone is suitable for effective detection and/or quantification of BRET. In this case, the energy transfer efficiency is represented using only the acceptor emission intensity. It would be readily apparent to one skilled in the art that in order to measure energy transfer, one can use the acceptor emission intensity without making any ratio calculation. This is due to the fact that ideally the acceptor molecule will emit light only if it absorbs the light transferred from the bioluminescent protein. In this case only one light filter is necessary.

In a related embodiment, the bioluminescent protein emission alone is suitable for effective detection and/or quantification of BRET. In this case, the energy transfer efficiency is calculated using only the bioluminescent protein emission intensity. It would be readily apparent to one skilled in the art that in order to measure energy transfer, one can use the donor emission intensity without making any ratio calculation. This is due to the fact that as the acceptor molecule absorbs the light transferred from the bioluminescent protein there is a corresponding decrease in detectable emission from the bioluminescent protein. In this case only one light filter is necessary.

In an alternative embodiment, the energy transfer efficiency is represented using a ratiometric measurement which only requires one optical filter for the measurement. In this case, light intensity for the donor or the acceptor is determined using the appropriate optical filter and another measurement of the samples is made without the use of any filter (intensity of the open spectrum). In this latter measurement, total light output (for all wavelengths) is quantified. Ratio calculations are then made using either equation 3 or 4. For the equation 3, only the optical filter for the acceptor is required. For the equation 4, only the optical filter for the donor is required.

$$E_d/E_o - E_a = \text{BRET ratio or} = E_o - E_d/E_a \tag{3}$$

$$E_o - E_d/E_d = \text{BRET ratio or} = E_d/E_o - E_d \tag{4}$$

where $E_a$ and $E_d$ are as defined above and $E_o$ is defined as the emission intensity for all wavelengths combined (open spectrum).

It should be readily apparent to one skilled in the art that further equations can be derived from equations 1 through 4. For example, one such derivative involves correcting for background light present at the emission wavelength for bioluminescent protein and/or acceptor molecule.

In performing a BRET assay, light emissions can be determined from each well using the BRETCount. The BRETCount instrument is a modified TopCount, wherein the TopCount is a microtiterplate scintillation and luminescence counter sold by Packard Instrument (Meriden, CT). Unlike classical counters which utilise two photomultiplier tubes (PMTs) in coincidence to eliminate background noise, Top-Count employs single-PMT technology and time-resolved pulse counting for noise reduction to allow counting in standard opaque microtiter plates. The use of opaque microtiter plates can reduce optical crosstalk to negligible level. TopCount comes in various formats, including 1, 2, 6 and 12 detectors (PMTs), which allow simultaneous reading of 1, 2, 6 or 12 samples, respectively. Beside the BRETCount, other commercially available instruments are capable of performing BRET: the Victor 2 (Wallac, Finland (Perkin Elmer Life Sciences)) and the Fusion (Packard Instrument, Meriden). BRET can be performed using readers that can detect at least the acceptor molecule emission and preferably two wavelengths (for the acceptor molecule and the bioluminescent protein) or more.

BRET is a ratiometric technique which can eliminate data variability caused by fluctuations in light output due to variations in assay volume, assay conditions and signal decay across different wells in a plate. RET-based reactions are homogeneous, generally occurring in solution without solid-phase attachment. This allows for detection of analytes in different forms such as liquid, gas and even particulates without separation.

Polypeptides

As would be understood by the person skilled in the art, various chemical entities useful in the present application may comprise a polypeptide. For example, the antibody, antibody-like molecule, antigen, labelled antigen, linker, first component of the CRET pair and/or second component of the CRET pair can consist of or comprise a polypeptide. The terms "polypeptide" and "protein" are generally used interchangeably and refer to a single polypeptide chain which may or may not be modified by addition of non-amino acid groups or other component such as a sugar moiety. The terms "proteins" and "polypeptides" as used herein also include variants, mutants, modifications, analogous and/or derivatives of the polypeptides of the disclosure as described herein. For example, the antibody or antibody-like molecules defined herein can comprise functional variants, mutants, modifications, analogous and/or derivatives thereof. The variants, mutants, modifications, analogous and/or derivatives thereof retain the ability to bind specifically to the antigen.

Polypeptide components can be produced in a variety of ways, including production and recovery of natural polypeptides, production and recovery of recombinant polypeptides, and chemical synthesis of the polypeptides. In one example, an isolated polypeptide component (e.g. an antibody) is produced by culturing a cell capable of expressing the polypeptide under conditions effective to produce the polypeptide, and recovering the polypeptide. Advantageously, in certain embodiments of the present application, one or more of the polypeptide components can be purchased from a commercial supplier. For example, the antibody or antibody-like molecule can be purchased from a commercial supplier and used to form the immunosensor of the present disclosure. Accordingly, any commercially available antibody or antibody-like molecule is suitable for use in the present disclosure. In an example, the antibody or antibody-like molecule can be produced or obtained from a commercial supplier and then covalently attached, optionally via a linker, the first component of the CRET pair to form an antibody conjugate.

Various exemplary cells capable of expressing polypeptides, such as antibodies or enzymes, are discussed below. In one example, a capable cell has been transformed with a polynucleotide encoding a polypeptide component. As used herein, "transformed" or "transformation" is the acquisition of new genes in a cell by the incorporation of a polynucleotide.

The term "polynucleotide" is used interchangeably herein with the term "nucleic acid". "Polynucleotide" refers to an oligonucleotide, nucleic acid molecule or any fragment thereof. It may be DNA or RNA of genomic or synthetic origin, double-stranded or single-stranded. Suitable polynucleotides may also encode secretory signals such as a signal peptide (i.e., signal segment nucleic acid sequences) to enable an expressed polypeptide to be secreted from the cell that produces the polypeptide. Examples of suitable signal segments include tissue plasminogen activator (t-PA), interferon, interleukin, growth hormone, viral envelope glycoprotein signal segments, *Nicotiana nectarin* signal peptide (U.S. Pat. No. 5,939,288), tobacco extensin signal, the soy oleosin oil body binding protein signal, *Arabidopsis thaliana* vacuolar basic chitinase signal peptide, as well as native signal sequences. In addition, the polynucleotide may encode intervening and/or untranslated sequences. Suitable polynucleotides may also encode polypeptide sequences which facilitate purification and/or identification of the expressed polypeptides. Examples of suitable purification tags are known in the art and include, but are not limited to, hexahistidine, GST, Trx, Calmodulin Binding Peptide, intein-chitin binding domain, Strep-tag, NusA, SUMO and MBP and epitope tags such as HA, c-myc, FLAG, Halotag and biotin. Suitable polynucleotides may also encode polypeptide sequences which comprise protease cleavage sites to facilitate removal of the purification and/or identification tags. Suitable protease cleavage sites are known in the art and include the TEV, thrombin and SUMO protease cleavage sites.

Mutant (altered) polypeptides can be prepared using any technique known in the art. For example, a polynucleotide encoding an enzyme encompassed by the present disclosure can be subjected to in vitro mutagenesis. Such in vitro mutagenesis techniques include sub-cloning the polynucleotide into a suitable vector, transforming the vector into a "mutator" strain such as the *E. coli* XL-1 red (Stratagene) and propagating the transformed bacteria for a suitable number of generations. In another example, the polynucleotides of the disclosure are subjected to DNA shuffling techniques as broadly described by Harayama (1998). Products derived from mutated/altered DNA can readily be screened using techniques described herein to determine if they can be used in an antibody conjugate/labelled analyte of the present disclosure.

In designing amino acid sequence mutants, the location of the mutation site and the nature of the mutation will depend on characteristic(s) to be modified. The sites for mutation can be modified individually or in series, e.g., by (1) substituting first with conservative amino acid choices and then with more radical selections depending upon the results achieved, (2) deleting the target residue, or (3) inserting other residues adjacent to the located site.

Amino acid sequence deletions generally range from about 1 to 15 residues, more preferably about 1 to 10 residues and typically about 1 to 5 contiguous residues.

Substitution mutants have at least one amino acid residue in the polypeptide molecule removed and a different residue inserted in its place. The sites of greatest interest for substitutional mutagenesis include sites identified as important for function. Other sites of interest are those in which particular residues obtained from various strains or species are identical. These positions may be important for biological activity. These sites, especially those falling within a sequence of at least three other identically conserved sites, are preferably substituted in a relatively conservative manner. Such conservative substitutions are known to the person skilled in the art.

Polynucleotides can be expressed using a suitable recombinant expression vector. For example, a polynucleotide encoding the above referenced polypeptide components can be operatively linked to an expression vector. The phrase "operatively linked" refers to insertion of a polynucleotide molecule into an expression vector in a manner such that the molecule is able to be expressed when transformed into a host cell. Typically, the phrase refers to the functional relationship of a transcriptional regulatory element to a transcribed sequence. For example, a promoter is operably linked to a coding sequence, if it stimulates or modulates the transcription of the coding sequence in an appropriate host cell. Generally, promoter transcriptional regulatory elements that are operably linked to a transcribed sequence are physically contiguous to the transcribed sequence, i.e., they are cis-acting. However, some transcriptional regulatory elements, such as enhancers, need not be physically contiguous or located in close proximity to the coding sequences whose transcription they enhance.

As used herein, an expression vector is a DNA or RNA vector that is capable of transforming a host cell and of effecting expression of a specified polynucleotide molecule. Preferably, the expression vector is also capable of replicating within the host cell. Expression vectors can be either prokaryotic or eukaryotic, and are typically viruses or plasmids. Suitable expression vectors include any vectors that function (i.e., direct gene expression) in a recombinant cell, including in bacterial, fungal, endoparasite, arthropod, animal, and plant cells. Vectors of the disclosure can also be used to produce a polypeptide component(s) in a cell-free expression system, such systems are well known in the art.

Suitable vectors can contain heterologous polynucleotide sequences, that is polynucleotide sequences that are not naturally found adjacent to polynucleotide encoding the above referenced polypeptides. The vector can be either RNA or DNA, either prokaryotic or eukaryotic, and typically is a transposon (such as described in U.S. Pat. No. 5,792,294), a virus or a plasmid.

Suitable, expression vectors can also contain regulatory sequences such as transcription control sequences, translation control sequences, origins of replication, and other regulatory sequences that are compatible with the recombinant cell and that control the expression of specified polynucleotide molecules. Transcription control sequences are sequences which control the initiation, elongation, and termination of transcription. Particularly important transcription control sequences are those which control transcription initiation, such as promoter, enhancer, operator and repressor sequences. A variety of suitable transcription control sequences are known to those skilled in the art. Examples, include transcription control sequences which function in bacterial, yeast, arthropod, plant or mammalian cells, such as, but not limited to, tac, lac, trp, trc, oxy-pro, omp/lpp, rrnB, bacteriophage lambda, bacteriophage T7, T7lac, bacteriophage T3, bacteriophage SP6, bacteriophage SP01, metallothionein, alphamating factor, *Pichia* alcohol oxidase, alphavirus subgenomic promoters (such as Sindbis virus subgenomic promoters), antibiotic resistance gene, baculovirus, *Heliothis zea* insect virus, vaccinia virus, herpesvirus, raccoon poxvirus, other poxvirus, adenovirus, cytomegalovirus (such as intermediate early promoters), simian virus 40, retrovirus, actin, retroviral long terminal•repeat, Rous sarcoma virus, heat shock, phosphate and nitrate transcription control sequences as well as other sequences capable of controlling gene expression in prokaryotic or eukaryotic cells.

A host cell suitable for preparing the antibody, antibody-like molecule, linker, antigen, first component of the CRET pair and/or second component of the CRET pair of the present disclosure includes a recombinant cell transformed with one or more polynucleotides that encode the antibody, antibody-like molecule, linker, antigen, first component of the CRET pair and/or second component of the CRET pair, or progeny cells thereof. Transformation of a polynucleotide molecule into a cell can be accomplished by any method by which a polynucleotide molecule can be inserted into the cell. Transformation techniques include, but are not limited to, transfection, electroporation, microinjection, lipofection, adsorption, and protoplast fusion. Transformed polynucleotide molecules can remain extrachromosomal or can integrate into one or more sites within a chromosome of the transformed (i.e., recombinant) cell in such a manner that their ability to be expressed is retained.

Suitable host cells to transform include any cell that can, be transformed with a polynucleotide encoding the antibody, antibody-like molecule, linker, antigen, first component of the CRET pair and/or second component of the CRET pair. Suitable host cells can be endogenously (i.e., naturally) capable of producing the antibody, antibody-like molecule, linker, antigen, first component of the CRET pair and/or second component of the CRET pair or can be capable of producing such polypeptides after being transformed with at least one polynucleotide molecule encoding the component(s). Suitable host cells include bacterial, fungal (including yeast), parasite, arthropod, animal and plant cells. Examples of host cells include *Salmonella, Escherichia, Bacillus, Listeria, Saccharomyces, Spodoptera, Mycobacteria, Trichoplusia*, BHK (baby hamster kidney) cells, MDCK cells, CRFK cells, CV-1 cells, COS (e.g., COS-7) cells, CHO cells and Vero cells. Further examples of host cells are *E. coli*, including *E. coli* K-12 derivatives; *Salmonella typhi; Salmonella typhimurium*, including attenuated strains; *Spodoptera frugiperda; Trichoplusia ni*; and non-tumorigenic mouse myoblast GS cells (e.g., ATCC CRL 1246). Suitable mammalian host cells include other kidney cell lines, other fibroblast cell lines (e.g., human, murine or chicken embryo fibroblast cell lines), myeloma cell lines, Chinese hamster ovary cells, mouse NIH/3T3 cells, LMTK cells and/or HeLa cells.

Recombinant techniques useful for increasing the expression of polynucleotide molecules of the present disclosure include, but are not limited to, operatively linking polynucleotide molecules to high-copy number plasmids, integration of the polynucleotide molecule into one or more host cell chromosomes, addition of vector stability sequences to plasmids, substitutions or modifications of transcription control signals (e.g., promoters, operators, enhancers), substitutions or modifications of translational control signals (e.g., ribosome binding sites; Shine-Dalgarno sequences), modification of polynucleotide molecules of the present disclosure to correspond to the codon usage of the host cell, and the deletion of sequences that destabilise transcripts.

Effective culture conditions include, but are not limited to, effective media, bioreactor, temperature, pH and oxygen conditions that permit polypeptide production. An effective medium refers to any medium in which a cell is cultured to produce a polypeptide of the present disclosure. Such medium typically comprises an aqueous medium having assimilable carbon, nitrogen and phosphate sources, and appropriate salts, minerals, metals and other nutrients, such as vitamins. Cells can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art.

Analyte

The antibody/antibody-like molecules, labelled antigens, methods, kits and compositions as defined herein can be used for detecting an analyte in a sample. Accordingly, antibody/antibody-like molecules, labelled antigens, such as those described herein, enable the detection of a plethora of antigens including disease biomarkers, pathogens, drugs, environmental contaminants, allergens and food adulterants, for POC diagnostics, therapeutic drug monitoring and companion diagnostics, clinical pharmokinetics, veterinary diagnostics, food analysis, environmental monitoring, defence and security.

As would be understood by the person skilled in the art, in some embodiments the analyte may be any molecule which can be bound by an antibody or antibody-like molecule or for which an antibody or antibody-like molecule can be developed. In some embodiments, the analyte is selected from the group consisting of small organic molecule, drug, drug metabolite, antibiotic, hormone, allergen, peptide, protein, naturally occurring antibody, sugar, lipid or nucleic acid. In some embodiments, the term "analyte" refers to serum proteins, cholesterol, polysaccharides, nucleic acids, drugs and drug metabolites, etc., found in bodily fluids and tissues of the body. In another embodiment, the analyte is any biological analyte, marker, gene, protein, metabolite, or hormone or combination therein indicative of a biological state desirable for analysis to determine a physical state or condition. In some embodiments, the analyte is a naturally occurring antibody.

As used herein, the term "small organic molecule" refers to an organic molecule, either naturally occurring or synthetic, that has a molecular weight of more than about 25 daltons and less than about 3000 daltons, preferably less than about 2500 daltons, more preferably less than about 2000 daltons, preferably between about 100 to about 1000 daltons, more preferably between about 200 to about 500 daltons. In some examples, the small organic molecule is a small organic molecule with antimicrobial, antibiotic, analgesic, or other biological activity. In one example, the small organic molecule is triclocarban (TCC). In another example, the small organic molecule is ampicillin.

The antibody/antibody-like molecules, labelled antigens, methods, kits and compositions as defined herein may be used in food analysis. In some embodiments, the analyte is an allergen contained in a food product. Allergens include, but are not limited to egg, dairy products, meat, fish, crustaceans for example prawns, crabs, lobster, crayfish, cereals containing gluten (for example wheat (such as spelt and khorasan wheat), rye, barley and oats), soybeans, beans, peanuts, nuts for example almonds, hazelnuts, walnuts, cashews, pecan nuts, Brazil nuts, pistachio nuts, macadamia (or Queensland) nuts, celery (including celeriac), mustard, sesame, sulphur dioxide/sulphites, lupin, molluscs like, mussels, whelks, oysters, snails and squid, seeds, fruits. In some embodiments, the analyte is casein, alpha-lactoglobulin, alpha-lactoglobulin, ovalbumin, ovomucoid, gliadin, Arah1, Arah2. In some embodiments, the antigen may be any of the epitopes and/or proteins identified in "Scientific Opinion on the evaluation of allergenic foods and food ingredients for labelling purposes". EFSA Panel on Dietetic Products, Nutrition and Allergies. EFSA Journal 2014; 12(11): 3894. For example, the antigen may be any of the epitopes and/or proteins listed in Table 3.

The food product may be any product intended for consumption that is suspected of containing an allergen. Other examples in food analysis include the detection of contaminants and adulterants in food products, for example, aflatoxins, other mycotoxins, natural or artificial hormones (including growth promoting hormones), antibiotics, pesticides, marine toxins and bacteria.

In another embodiment, the analyte is melamine, cyanuric acid or any other nitrogenous compound used to fraudulently increase the nitrogen content of dairy product and the antibody or antibody-like molecule is an antibody specific for melamine, cyanuric acid or the other nitrogenous compound used to fraudulently increase the nitrogen content of dairy product. In yet a further embodiment, the analyte is a coagulase enzyme from *Staphylococcus aureus* and the antibody or antibody-like molecule is an antibody specific for coagulase enzyme from *S. aureus*.

In alternative embodiments the analyte may be a naturally occurring antibody which competes with the antibody or antibody-like molecule defined herein for binding to the labelled antigen. As used herein, a "naturally occurring antibody" refers to an antibody generated in a subject, for example, during an immune response to an infection with a microorganism, such as a bacterium, virus, fungus, mycoplasma or parasite or an immunisation. In these embodiments, binding of the labelled antigen to the naturally occurring antibody results in a reduction the efficiency of energy transfer between the first component of the CRET pair and the second component of the CRET pair. In some embodiments, the analyte is a naturally occurring antibody raised in a subject in response to an immunisation. In some embodiments, the analyte is a naturally occurring antibody

TABLE 3

Exemplary epitopes and/or proteins.

| Food | Epitope and/or protein |
| --- | --- |
| wheat | Profilin, non-specific lipid transfer protein, agglutinin, isolectin 1, ω-5-gliadin, thioredoxin, high molecular weight glutenin, low molecular weight glutenin GluB3-23, α-purothionin |
| barley | profilin, α-amylase inhibitor BMAI-1 precursor, α-amylase, β-amylase, γ-hordein 3 |
| rye | γ-secalin |
| oats | avenin |
| whey | α-lactalbumin, β-lactoglobulin, bovine serum albumin, immunoglobulin, Lactoferrin 1 |
| casein | αs1-casein, αs2-casein, β-casein, γ1-casein, γ2-casein, γ3-casein, κ-casein |
| egg | ovomucoid, ovalbumin, ovotransferrin, lysozyme C, serum albumin, (α-livetin), YGP42 |
| tree nuts | hazelnut, walnut, almond, cashew nut, brazil nut, pecan nut, pistachio, chestnut |
| peanuts | 7S globulin (vicilin-type), conglutin (2S albumin), 11S globulin (legumin) profilin, conglutin (2S albumin), conglutin (2S albumin), PR-10, non-specific lipid transfer protein, oleosins, defensins. |
| soy | hydrophobic protein, defensin, profilin, PR-10 protein, β-conglycinins (7S globulin, vicilin), glycinins (11S globulin, legumin), seed biotinylated protein, 2S albumin |
| fish | β-Parvalbumin, tropomyosin, β-enolase, aldolase A, vitellogenin (β'-component) from some of the following species: *Clupea harengus, Cyprinus carpio, Gadus callarias Gadus morhua, Lates calcarifer, Lepidorhombus whiffiagonis, Oncorhynchus mykiss, Salmo salar Sardinops sagax, Sebastes marinus Thunnus albacares Xiphias gladius, Oreochromis mossambicus, Oncorhynchus keta* and other fish species |
| crustacea | tropomyosin, arginine kinase, myosin light chain 2, sarcoplasmic calcium-binding protein, myosin light chain 1, troponin C, troponin I, triosephosphate isomerase from any species of crustacean. |
| celery | PR-10, non-specific lipid transfer protein 1, chlorophyll a-b binding protein, profilin, FAD-containing oxidase, non-specific lipid transfer protein 2 | raised in a subject in response to an infection with a microorganism. In some embodiments, the subject is a human or other animal. For example, the subject can be selected from the group consisting of humans, beef cattle, dairy cattle, sheep, goats, horses, swine, buffalos and camelids (for example, camels and llamas). In some embodiment, the subject is a human. In some embodiments, the subject is livestock. As used herein, the term "livestock" refers to animals, such as beef cattle, dairy cattle, sheep, goats, horses, swine, buffalos and camels raised for food or for the production of food for home use or for large scale production and or for profit, particularly on a farm.

The antibody/antibody-like molecules, labelled antigens, methods, kits and compositions as defined herein can be used to qualitatively and/or quantitatively "detect" analytes. In one embodiment, the analytes are present in micromolar to nanomolar concentrations.

The methods, kits, antibody or antibody-like molecules and labelled antigens described herein can be used to detect and quantify analytes in a sample. The "sample" can be any substance or composition that has the potential to contain the analyte of interest. In some embodiments, the sample is air, liquid, biological material or soil. In some embodiments, the sample is selected from the group consisting of a food product or an extract thereof, soil or an extract thereof, biological materials or an extract thereof and the like. The sample may be obtained directly from the environment or source, or may be extracted and/or at least partially purified by a suitable procedure before a method of the invention is performed.

In some examples, the sample comprises a biological material. As used herein, "biological materials" is defined broadly and includes any material derived in whole or in part from an organism. Biological materials include, but are not limited to, bodily fluids, cells, soft tissues (such as connective and non-connective tissue) and hard tissues (such as bone and cartilage). In some embodiments, the bodily fluids are blood, serum, sputum, mucus, pus, peritoneal fluid, urine or other bodily fluids. In some embodiments, such materials may have been harvested from a living organism and then subjected to further processing and/or chemical treatment. In an embodiment, the sensor is not used to detect an analyte within a living cell. In some embodiments, the sensor is used ex vivo.

In some examples, the sample comprises a food product. As used herein, food product is defined broadly and includes a composition that is intended to be ingested by an animal, including mammals, for nutritional purposes, whether eaten or drunk. In some embodiments, the sample is a food product that is or has the potential to be contaminated with a toxin, allergen, adulterant and the like.

In some embodiments, the sample is an aqueous liquid. For example, the sample includes but is not limited to, milk, fruit juices, other beverages and bodily fluids including blood serum.

As the skilled person would be aware, the immunosensors of the present invention can also be multiplexed. As used herein, the term "immunosensor" refers to the combination of antibody or antibody-like molecule attached to a first component of the CRET pair and corresponding labelled antigen attached to a second component of a CRET pair. As the person skilled in the art would understand, an "immunosensor" can also be referred to as a "CRET pair". For example, two or more different antibodies or antibody-like molecules with corresponding labelled antigens may be provided which detect a different analyte. For example, an antibody or antibody-like molecule of the present invention that detects one allergen can be multiplexed with an antibody or antibody-like molecule that detect another allergen. In some embodiments, each different immunosensor may include a different donor and/or acceptor domains such that they emit at different wavelengths to enable the detection and quantification of different analytes. In some embodiments, each different immunosensor may comprise the same donor and/or acceptor molecule. In some embodiments, a single fluidic detection chamber is used. In some embodiments, a multi-channel detection device may be used.

Compositions, Kits, Methods and Uses

The antibody or antibody-like molecules and/or labelled analytes described herein may be included in compositions for use in detecting analytes. For example, the antibody or antibody-like molecules and/or labelled analytes described herein may be included in compositions for use in detecting analytes. In some embodiments, there is provided a composition comprising an antibody or antibody-like molecule in accordance with the present invention and an acceptable carrier. In some embodiments, there is provided a composition comprising an antibody or antibody-like molecule and a labelled analyte in accordance with the present invention and an acceptable carrier. In some embodiments, there is provided a composition comprising labelled analyte in accordance with the present invention and an acceptable carrier. As used herein, the term "acceptable carrier" includes any and all solids or solvents (such as phosphate buffered saline buffers, water, saline) dispersion media, coatings, and the like, compatible with the methods and uses of the present invention. The acceptable carriers must be "acceptable" in the sense of being compatible with the other ingredients of the composition, not damaging the analytes being tested for and not inhibiting specific binding of the analyte to the antibody or fragment thereof. Generally, suitable acceptable carriers are known in the art and are selected based on the end use application.

As the skilled person would appreciate, the antibody or antibody-like molecules and/or labelled antigens of the present application can be used to detect the presence or absence of analyte in a sample, and if present may also be used to determine the amount of the analyte present in the sample. Therefore, in some embodiments there is provided a method for detecting an analyte in a sample, the method comprising i) contacting the sample with:
   an antibody or antibody-like molecule capable of binding to the analyte attached to a first component of a chemiluminescence resonance energy transfer (CRET) pair; and
   a labelled antigen comprising an antigen capable of binding to the antibody or the antibody-like molecule attached to a second component of the CRET pair;
   wherein, when the labelled antigen is bound to the antibody or the antibody-like molecule, the efficiency of energy transfer between the first component of the CRET pair and the second component of the CRET pair is in the range of 10 to 75%; and ii) determining if the efficiency of energy transfer between the first component of the CRET pair and the second component of the CRET pair has been altered in the presence of the sample, wherein a reduction in the efficiency of energy transfer between the first and second components of the CRET pair indicates that the analyte is present in the sample.

In some embodiments, the reduction in the efficiency of energy transfer between the first and second components of the CRET pair is observed in real time. In alternative embodiments, the reduction in the efficiency of energy transfer between the first and second components of the CRET pair is relative to the efficiency of energy transfer between the first and second components of the CRET pair in the absence of sample (for example, in the presence of a buffer control).

In some embodiments, the efficiency of energy transfer from the first component to the second component is in the range of 15 to 75%, 20 to 75%, 25 to 75%, 30 to 75%, 35 to 75%, 40 to 75%, 45 to 75%, 50 to 75%, 55 to 75%, 60 to 75%, or greater than 10%, greater than 15%, greater than 20%, greater than 25%, greater than 30%, greater than 35%, greater than 40%, greater than 45% or greater than 50%, when the labelled antigen is bound to the antibody or antibody-like molecule. In some embodiments, the efficiency of energy transfer from the first component to the second component is in the range of 15 to 65% when the labelled antigen is bound to the antibody or antibody-like molecule.

In some embodiments, step (i) comprises
(a) first contacting the sample with the antibody or antibody-like molecule and then contacting the resulting mixture with the labelled antigen;
(b) first contacting the sample with the labelled antigen and then contacting the resulting mixture with the antibody or antibody-like molecule; or
(c) contacting the sample with the antibody or antibody-like molecule and the labelled antigen at the same time.

As would be understood by the person skilled in the art, in each of (i)(a), (i)(b) and (i)(c), the presence of an analyte of interest in the sample will result in a reduction in the efficiency of energy transfer between the first and second components of the CRET pair relative to a control in which the sample is not added, for example where a buffer blank is used instead of the sample. For instance, if the method is performed by first contacting the sample with the antibody or antibody-like molecule and then contacting the resulting mixture with the labelled antigen (i.e. step (i)(a)) there will be an increase in the efficiency of energy transfer between the first and second components of the CRET pair after contacting the resulting mixture with the labelled antigen (i.e. observed in real time). However, if an analyte of interest is present in the sample, there will be a reduction in the efficiency of energy transfer between the first and second components of the CRET pair relative to the efficiency of energy transfer between the first and second components of the CRET pair in the absence of the sample. Similarly, if the method is performed by contacting the sample with the antibody or antibody-like molecule and the labelled antigen at the same time (i.e. step (i)(c)) the efficiency of energy transfer between the first and second components of the CRET pair may not change in real time. However, if an analyte of interest is present in the sample, there will be a reduction in the efficiency of energy transfer between the first and second components of the CRET pair relative to the efficiency of energy transfer between the first and second components of the CRET pair in the absence of the sample. If step (i) is performed by first contacting the sample with the labelled antigen and then contacting the resulting mixture with the antibody or antibody-like molecule (i.e. step (i)(b)), a reduction in the efficiency of energy transfer between the first and second components of the CRET pair will be observed in real time if the analyte of interest is present in sample.

In some embodiments, step ii) comprises comparing the efficiency of energy transfer between the first component of the CRET pair and the second component of the CRET pair in the presence of sample to the efficiency of energy transfer between the first component of the CRET pair and the second component of the CRET pair in the absence of sample, wherein a reduction in the efficiency of energy transfer between the first and second components of the CRET pair in the presence of sample indicates that the analyte is present in the sample. In some embodiments, step ii) comprises comparing the efficiency of energy transfer between the first component of the CRET pair and the second component of the CRET pair before the sample is added to the efficiency of energy transfer between the first component of the CRET pair and the second component of the CRET pair after the sample is added, wherein a reduction in the efficiency of energy transfer between the first and second components of the CRET pair in the presence of sample indicates that the analyte is present in the sample.

In some embodiments, step (i) further comprises contacting the sample with a substrate.

In preferred embodiments, the method does not require a secondary antibody. These embodiments provide an advantage over a number of techniques known in the art (such as ELISA, Western blot, immunohistochemistry, immunocytochemistry, flow cytometry) as a secondary antibody is not required. This reduces the number of steps required in the assay and can reduce the time required to perform the method. In some embodiments, the method is performed in real time.

In some embodiments, determining if the spatial location and/or dipole orientation of the BRET donor domain relative to the acceptor domain has been altered in the presence of the sample comprises measuring the BRET ratio before and after addition of the sample.

In some embodiments, the method further comprises determining the concentration of the analyte in the sample. In some embodiments, the concentration of an analyte in a sample can be determined by comparing the efficiency of energy transfer (for example, as represented by the BRET ratio) in the presence of sample with the efficiency of energy transfer at known concentrations of analyte, for example by constructing a standard curve. In some embodiments, the methods of the present invention can be used to measure the concentration of an analyte in a sample at nanomolar or picomolar levels. For example, in some embodiments, at least 1 pM, at least 5 pM, at least 10 pM, at least 25 pM, at least 50 pM, at least 75 pM, at least 100 pM, at least 200 pM, at least 300 pM, at least 400 pM, at least 500 pM, at least 600 pM, at least 700 pM, at least 800 pM, at least 900 pM, at least 1 nM, at least 5 nM, at least 10 nM, at least 25 nM, at least 50 nM, at least 75 nM, at least 100 nM, at least 200 nM, at least 300 nM, at least 400 nM, at least 500 nM, at least 600 nM, at least 700 nM, at least 800 nM, at least 900 nM, of analyte can be detected.

In an example, there is provided a method of detecting an analyte in a sample, the method comprising
i) contacting the sample, in the presence of coelenterazine, with:
a) an antibody or antibody-like molecule capable of binding to the analyte attached to *Renilla* luciferase or a variant thereof; and
a labelled antigen comprising an antigen capable of binding to the antibody or antibody-like molecule attached to green fluorescent protein 2; and
ii) determining whether bioluminescent resonance energy transfer (BRET) between the *Renilla* luciferase and the green fluorescent protein 2 is modified, wherein a reduction in the efficiency of energy transfer between the *Renilla* luciferase and the green fluorescent protein 2 indicates the analyte is present in the sample. In some embodiments, step (i) further comprises contacting the sample with a substrate.

In some embodiments, there is provided a method of classifying a sample, the method comprising
- i) flowing through a microfluidic device comprising one or more microchannels,
  - a) the sample,
  - b) an antibody or antibody-like molecule capable of binding to the analyte attached to a first component of a CRET pair,
  - c) a labelled antigen comprising an antigen capable of binding to the antibody or antibody-like molecule attached to a second component of a CRET pair,
  - d) a substrate of one of the first or second component of the CRET pair,
  wherein, when the labelled antigen is bound to the antibody or antibody-like molecule, the efficiency of energy transfer between the first component and the second component is in the range of 10 to 75%,
- ii) mixing the antibody or antibody-like molecule, labelled antigen, sample and substrate in the device,
- iii) detecting modification of the substrate by the first or second component of the CRET pair using an electro-optical sensing device,
- iv) processing at least one signal from the electro-optical sensing device and correlating the pattern of electro-optical responses with one or more pre-determined characteristics of one or more samples of interest, and
- v) classifying the sample based on the correlation of the pattern of responses, wherein the efficiency of energy transfer between the first and second components of the CRET pair is altered when one or more analytes binds the antibody or antibody-like molecule.

The method above method can be used to classify a sample based on the analytes they contain. In some embodiments, the above method can be used to classify a sample based on the presence, absence or concentration of one or more analytes. In some embodiments, the above method comprises two or more different antibody or antibody-like molecules each of which binds a different analyte or range of analytes and two or more different labelled antigens, and step v) comprises classifying the sample based on the presence, absence or concentration of each of the analytes or range of analytes. In some embodiments, the sample is classified into two or more classes, for example safe or hazardous, contaminated or uncontaminated, authentic or fraudulent or low value/medium value/high value. In some embodiments, the method can be used to classify the sample in real time. In some embodiments, the sensor molecule is not fixed to the device. In some embodiments, the sensor molecule and substrate enter the device through different microchannels.

In some embodiments, the antibody or antibody-like molecules and labelled antigens described herein can also be used in methods for detecting naturally occurring antibodies. Therefore, in some embodiments there is provided a method of detecting a naturally occurring antibody in a sample, the method comprising
- i) contacting the sample with:
  - an antibody or antibody-like molecule attached to a first component of a chemiluminescence resonance energy transfer (CRET) pair; and
  - a labelled antigen comprising an antigen capable of binding to the naturally occurring antibody attached to a second component of the CRET pair;
  - wherein the antibody or antibody-like molecule attached to a first component of the CRET pair and the naturally occurring antibody are capable of binding to the labelled antigen; and
  - wherein, when the labelled antigen is bound to the antibody or the antibody-like molecule attached to the first component of the CRET pair, the efficiency of energy transfer between the first component of the CRET pair and the second component of the CRET pair is in the range of 10 to 75%; and
- ii) determining if the efficiency of energy transfer between the first component of the CRET pair and the second component of the CRET pair has been altered in the presence of the sample, wherein a reduction in the efficiency of energy transfer between the first and second components of the CRET pair indicates that the naturally occurring antibody is present in the sample.

In some embodiments, step (i) further comprises contacting the sample with a substrate.

In some embodiments, step (ii) comprises determining if the efficiency of energy transfer between the first component of the CRET pair and the second component of the CRET pair has been reduced in the presence of the sample. For example, the CRET ratio may be reduced by 5%, 10%, 15%, 20%, 25%, 30%, 35%, 40%. 45%, 50%, 55%. 60%, 65%, 70%, 75%, 80%, 85%, 90%, or 95% in the presence of the sample. In some embodiments, the CRET ratio is be reduced by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% in the presence of sample.

In some embodiments, step (ii) comprises determining if the efficiency of energy transfer between the first component of the CRET pair and the second component of the CRET pair has been increased in the presence of the sample.

In some embodiments, step (i) comprises
- (a) first contacting the sample with the antibody or antibody-like molecule and then contacting the resulting mixture with the labelled antigen;
- (b) first contacting the sample with the labelled antigen and then contacting the resulting mixture with the antibody or antibody-like molecule; or
- (c) contacting the sample with the antibody or antibody-like molecule and the labelled antigen at the same time.

As explained above, in each of (i)(a), (i)(b) and (i)(c), the presence of an analyte of interest in the sample will result in a reduction in the efficiency of energy transfer between the first and second components of the CRET pair relative to a control in which the sample is not added, for example where a buffer blank is used instead of the sample.

In some embodiments, step (i) further comprises contacting the sample with a substrate.

In some embodiments, the efficiency of energy transfer from the first component to the second component is in the range of 15 to 75%, 20 to 75%, 25 to 75%, 30 to 75%, 35 to 75%, 40 to 75%, 45 to 75%, 50 to 75%, 55 to 75%, 60 to 75%, or greater than 10%, greater than 15%, greater than 20%, greater than 25%, greater than 30%, greater than 35%, greater than 40%, greater than 45% or greater than 50%, when the labelled antigen is bound to the antibody or antibody-like molecule. In some embodiments, the efficiency of energy transfer from the first component to the second component is in the range of 15 to 65% when the labelled antigen is bound to the antibody or antibody-like molecule.

In some embodiments, the method further comprises determining the concentration of the naturally occurring antibody in the sample. In some embodiments, the concentration of the naturally occurring antibody in a sample can be determined by comparing the efficiency of energy transfer (for example, as represented by the BRET ratio) in the presence of sample with the efficiency of energy transfer at known concentrations of naturally occurring antibody, for example by constructing a standard curve. In some embodiments, the methods of the present invention can be used to measure the concentration of an analyte in a sample at nanomolar or picomolar levels. For example, in some embodiments, at least 1 pM, at least 5 pM, at least 10 pM, at least 25 pM, at least 50 pM, at least 75 pM, at least 100 pM, at least 200 pM, at least 300 µM, at least 400 pM, at least 500 pM, at least 600 pM, at least 700 pM, at least 800 pM, at least 900 pM, at least 1 nM, at least 5 nM, at least 10 nM, at least 25 nM, at least 50 nM, at least 75 nM, at least 100 nM, at least 200 nM, at least 300 nM, at least 400 nM, at least 500 nM, at least 600 nM, at least 700 nM, at least 800 nM, at least 900 nM, of analyte can be detected.

In these embodiments, the method can be used to detect and quantify seroconversion in a subject. As used herein, "seroconversion" is intended to refer to the situation where an infection with a microorganism, such as a bacterium, virus, fungus, mycoplasma or parasite or an immunisation generates an immune response in a subject. Measurement of the immune response, "serology", is frequently used to determine the infection status, immune status or susceptibility to complications of the subject. In example embodiments, the sample is serum or other biological fluids suspected of containing naturally antibodies This disclosure encompasses kits, which may include, but are not limited to, one or more of the following: an antibody or antibody-like molecule attached to a first component of a CRET system, a labelled antigen attached to a second component of a CRET system, a substrate, a test standard, and directions (written instructions for their use). The components listed above can be tailored to the particular analyte to be monitored. The kit can further include appropriate buffers and reagents known in the art performing the methods described herein.

System

The methods of the present invention can be performed on any system suitable for measuring energy transfer between a CRET pair.

As the person skilled in the art will appreciate the methods of the present invention can be performed in a batch (for example batch format using a plate reader) or flow format. For example, the methods of the present invention can be performed in a microplate format using a microplate reader equipped with the appropriate filters. The methods of the present invention can also be performed on a microfluidic device, such as described in WO2013/155553. The methods of the present invention can also be performed on a microfluidic device, such as described in WO 2013/155553. An example of a BRET based assay performed on a microfluidics device (the CYBERTONGUE device) is provided in PCT/AU2018/050824.

In some embodiments, there is provided a microfluidic system for detecting an analyte in a sample, the system comprising
  i) at least one reservoir suitable for containing an antibody or antibody-like molecule capable of binding to the analyte attached to a first component of a CRET pair,
  ii) at least one reservoir suitable for containing a labelled antigen comprising an antigen capable of binding to the antibody or antibody-like molecule attached to a second component of the CRET pair;
  iii) a microfluidic device comprising one or more microchannels,
  iv) means for mixing the antibody or antibody-like molecule, the labelled antigen, the sample and a substrate of the first or second component of the CRET pair in the device,
  v) a reaction chamber for detecting binding of the analyte to the antibody or antibody-like molecule, and
  vi) an electro-optical sensing device,
  wherein, when the labelled antigen is bound to the antibody or antibody-like molecule, the efficiency of energy transfer between the first component of the CRET pair and the second component of the CRET pair is in the range of 10 to 75%; and
  wherein a reduction in the efficiency of energy transfer between the first and second components of the CRET pair indicates the analyte is present in the sample. In an example, the system can be used to detect the analyte in real time.

In some embodiments, the antibody or antibody-like molecule is not fixed to the device. In an example, the antibody or antibody-like molecule, labelled antigen and substrate enter the device through different microchannels. In an example, the microfluidic device comprises at least two input microchannels, wherein one of the input microchannels is for flowing the antibody or antibody-like molecule into the device.

In some embodiments, the electro-optical sensing device comprises at least two different wavelength channels. In some examples, the electro-optical sensing device is capable of simultaneously, or in rapid succession, detecting two different wavelength channels. In some examples, the electro-optical sensing device is capable of detecting two different wavelength channels in less than 1 second.

In some embodiments, the microfluidic device is designed to enable the detection of two or more analytes.

In other embodiments, there is provided a method of classifying a sample, the method comprising
  (i) contacting a sample with
    a) an antibody or antibody-like molecule capable of binding to an analyte attached to a first component of a CRET pair,
    b) a labelled antigen comprising an antigen capable of binding to the antibody or antibody-like molecule attached to a second component of a CRET pair,
    c) a substrate of one of the first or second component of the CRET pair,
  wherein, when the labelled antigen is bound to the antibody or antibody-like molecule, the efficiency of energy transfer between the first component and the second component is in the range of 10 to 75%,
  ii) detecting modification of the substrate by the first or second component of the CRET pair using an electro-optical sensing device,
  iv) processing at least one signal from the electro-optical sensing device and correlating the pattern of electro-optical responses with one or more pre-determined characteristics of one or more samples of interest, and
  v) classifying the sample based on the correlation of the pattern of responses, wherein the efficiency of energy transfer between the first and second components of the CRET pair is altered when one or more analytes binds the antibody or antibody-like molecule. In some embodiments, step (i) comprises:

A) flowing through a microfluidic device comprising one or more microchannels,
   a) the sample,
   b) the antibody or antibody-like molecule,
   c) the labelled antigen, and
   d) the substrate; and
B) mixing the antibody or antibody-like molecule, labelled antigen, sample and substrate in the device.

In some embodiments, the method comprises two or more different antibody or antibody-like molecules each of which binds a different analyte or range of analytes and two or more different labelled antigens. In some embodiments, the methods can be used to classify samples in real time. In some embodiments, the antibody or antibody-like molecule is not fixed to the device. In some embodiments, the antibody or antibody-like molecule, labelled antigen and substrate enter the device through different microchannels. In some embodiments, the microfluidic device comprises at least two input microchannels, wherein one of the input microchannels is for flowing the antibody or antibody-like molecule into the device. In some embodiments, the methods of classifying a sample can be used to classify as sample based on the presence or absence of one or more analytes or the concentration of an analyte. For example, the methods may be used to classify a sample as free of an allergen when the allergen is present below a pre-determined level and/or is undetectable.

EXAMPLES

The following examples set forth preferred antibodies, labelled antigens and methods in accordance with the invention. It is to be understood, however, that these examples are provided by way of illustration and nothing therein should be taken as a limitation upon the overall scope of the invention.

Example 1. Preparation of FLAG-GFP$^2$

Molecular Biology: A DNA sequence encoding amino acid residues 2 to 239 of GFP$^2$ was amplified by PCR. This was ligated into a modified pET43a *E. coli* expression vector designed to encode an N-terminal hexahistidine (His) tag followed by a tobacco etch virus protease (TEV) cleavage site, a SUMO solubility tag, SUMO protease cleavage site and a FLAG epitope, followed by the GFP$^2$ sequence. The resulting protein sequence is listed under SEQ ID NO: 4.

Protein Expression: To produce recombinant His-TEV-SUMO-FLAG-GFP$^2$ protein, the expression plasmid was transformed into *E. coli* BL21 DE3 strain and grown with shaking at 37° C. in Terrific broth (TB) supplemented with 100 μg/ml Ampicillin until an OD600 of 0.7 was reached. Cultures were transferred to 16° C., protein expression was induced by the addition of isopropyl β-D-1-thiogalactopyranoside (IPTG) to a final concentration of 0.5 mM and the cultures were shaken overnight for a further 16 h. Following expression, cell cultures were centrifuged at 5000×g for 20 min and the resulting cell pellets were stored frozen at −20° C.

Protein Purification: Protein purification was initiated by thawing the cell pellet in Lysis buffer (25 mM Tris-HCl pH 8.0, 300 mM NaCl, 2 mM MgCl$_2$, 10 mM imidazole, 0.5 mg/ml lysozyme, 5 U/ml benzonase endonuclease [EMD Millipore], 1 mM PMSF, complete protease inhibitor tablets EDTA-free [Roche]) using a ratio of 5 ml of buffer per 1 g of cells. Cells were further lysed by 3 passes through an ice cooled Avestin C5 cell crusher and centrifuged at 48,000×g at 4° C. Supernatant (cell lysate) was filtered through a 5 μm filter and applied onto a 5 ml HiTrap IMAC Sepharose FF column (GE Healthcare) pre-equilibrated with IMAC wash buffer 1 (25 mM Tris-HCl pH 8.0, 300 mM NaCl, 10 mM imidazole) using the Profinia Affinity chromatography purification system (Bio-Rad). The IMAC column was sequentially washed with IMAC Wash buffer 1 and IMAC Wash buffer 2 (25 mM Tris-HCl pH 8.0, 300 mM NaCl, 20 mM imidazole) and the bound His-TEV-SUMO-FLAG-GFP$^2$ protein eluted with IMAC Elution buffer (25 mM Tris-HCl pH 8.0, 300 mM NaCl, 350 mM imidazole). IMAC-eluted protein was further purified by passing through a HiLoad 16/60 Superdex 75 column (GE Healthcare) pre-equilibrated with gel filtration buffer (25 mM Tris-HCl pH 8.0, 150 mM NaCl).

The purified His-TEV-SUMO-FLAG-GFP$^2$ protein was incubated with SUMO protease overnight at 16° C. and at a protein to protease ratio of 50:1 to remove the N-terminal His and SUMO tags. The next morning, imidazole was added to the reaction to a final concentration of 20 mM, and the reaction mixture was passed once more over a 5 ml HiTrap IMAC column to remove the protease and the cleaved tags. Two washes with IMAC Wash buffer 2 followed, and the untagged FLAG-GFP$^2$ protein was collected from the unbound fraction and the first IMAC wash. The fractions containing the cleaved FLAG-GFP$^2$ protein were then concentrated using Amicon Ultra centrifugal filter unit (Ultra-15 MWCO 10 kDa) and loaded onto a HiLoad 16/60 Superdex 75 column (GE Healthcare) pre-equilibrated with gel filtration buffer. The appropriate peak was collected and the protein was concentrated to 1.7 mg/ml before being flash-frozen in liquid nitrogen in 500 μl aliquots and stored at −70° C. The presence of the FLAG epitope in all the fusion proteins was confirmed by Western blot analysis (data not shown).

Example 2. Preparation of RLuc8

Molecular Biology: A codon optimised DNA sequence (for expression in *E. coli*) encoding residues 2 to 311 of the *Renilla reniformis* Luciferase (RLuc8) followed by a Sorta-seA bioconjugation sequence (LPETGG) was synthesised by GenScript USA Inc (Piscataway, New Jersey, USA). This was ligated into a modified pET43a *E. coli* expression vector designed to encode an N-terminal hexahistidine tag followed by a tobacco etch virus protease (TEV) cleavage site and by the RLuc8-LPETGG sequence. The resulting protein sequence is listed under SEQ ID NO: 5.

Protein Expression: To produce recombinant N-His-RLuc8 protein, the expression plasmid was transformed into *E. coli* BL21 DE3 strain and grown with shaking at 37° C. in Terrific broth (TB) supplemented with 100 μg/mL Ampicillin until an OD600 of 0.7 was reached. Cultures were transferred to 16° C. and protein expression was induced by the addition of IPTG to a final concentration of 0.5 mM. After the addition of IPTG, the cultures were shaken overnight for a further 16 hours. Following expression, cell cultures were centrifuged at 5000×g for 20 min and cell pellets were stored frozen at −20° C.

Protein Purification: Protein purification was initiated by thawing the cell pellet in Lysis buffer (25 mM Tris-HCl pH 8.0, 300 mM NaCl, 2 mM MgCl$_2$, 10 mM Imidazole, 0.5 mg/mL lysozyme, 5 U/mL benzonase endonuclease [EMD Millipore], 1 mM PMSF, complete protease inhibitor tablets EDTA-free [Roche]) using a ratio of 5 mL of buffer per 1 g of cells. Cells were further lysed by 3 passes through an ice cooled Avestin C5 cell crusher and centrifuged at 48,000×g at 4° C. Supernatant (cell lysate) was filtered through a 5 µm filter and applied onto a 5 mL HiTrap IMAC Sepharose FF column (GE Healthcare) pre-equilibrated with IMAC wash buffer 1 (25 mM Tris-HCl pH 8.0, 300 mM NaCl, 10 mM Imidazole) using the Profinia Affinity chromatography purification system (Bio-Rad). The IMAC column was then sequentially washed with IMAC Wash buffer 1 and IMAC Wash buffer 2 (25 mM Tris-HCl pH 8.0, 300 mM NaCl, 20 mM Imidazole) then the bound N-terminal HIS tagged RLuc8 protein was eluted with IMAC Elution buffer (25 mM Tris-HCl pH 8.0, 300 mM NaCl, 350 mM Imidazole). The IMAC eluted protein was further purified by passing it through a HiLoad 16/60 Superdex 75 column pre-equilibrated in 1×PBS (137 mM NaCl, 2.7 mM KCl, 4.3 mM $Na_2HPO_4$, 1.47 mM $KH_2PO_4$ pH 7.4). Fractions containing the monomer and dimer were pooled separately before being flash-frozen in 500 µL aliquots and stored at −70° C.

Throughout purification, fractions contain RLuc8 were identified by SDS-PAGE analysis and Western blot analysis using an anti-His antibody-HRP conjugate and detection by α-chloronaphthol. Mass spectrometry analysis of the final pooled fractions found the mass of the protein to be 38981.2 Da, in excellent agreement with the predicted mass of 38981.37 Da (with loss of N-terminal methionine).

Luciferase activity: Coelenterazine 400a (Cayman Chemicals) (6-phenyl-2,8-bis(phenylmethyl)-imidazo[1,2-a]pyrazin-3(7H)-one) (1 mg) was dissolved in 10.2 mL ethanol and partitioned into 200 µL aliquots which were dried (Speedivac) and stored at −20° C. until use.

Coelenterazine 400a (50 nmol) was dissolved in 50 µL ethanol and 450 µL water was added. RLuc8 monomer (2.4 mg/mL) and RLuc8 dimer (4.8 mg/mL) were diluted in 1 mg/mL BSA in buffer. In a well of a white 96-well Optiplate (Perkin Elmer) was added TBS, PBS or 100 mM sodium phosphate pH 7.0, 2 µL luciferase enzyme (1/10 or 1/100 dilution) and 5 µL of 0.1 mM Coelenterazine 400a solution. The final volume in each well was 100 µL. The light produced was measured in a FLUOstar Optima (BMG Labtech) using luminescence optics and no filter. The results of the luciferase activity assays indicated that luciferase activity of N-His-RLuc8 decreased very rapidly (over a few seconds), so initial readings were recorded (data not shown). The N-His-RLuc8 monomer was found to be more active than the dimeric form, so all conjugation experiments were performed with the monomeric form of the protein.

Example 3. Preparation of FLAG-RLuc8

Molecular Biology: A codon optimized DNA sequence (for expression in *E. coli*) encoding residues 2 to 311 of the *Renilla reniformis* Luciferase (RLuc8) followed by a SortaseA bioconjugation sequence (LPETGG) was synthesised by GenScript USA Inc (Piscataway, New Jersey, USA). This was ligated into a modified pET43a *E. coli* expression vector designed to encode an N-terminal hexahistidine tag followed by a tobacco etch virus protease (TEV) cleavage site, a SUMO solubility tag, SUMO protease cleavage site and a FLAG epitope, followed by the RLuc8-LPETGG sequence. The resulting protein sequence is listed in SEQ ID NO: 6.

Protein Expression: To produce recombinant FLAG-RLuc8 protein, the expression plasmid was transformed into *E. coli* BL21 DE3 strain and grown with shaking at 37° C. in Terrific broth (TB) supplemented with 100 µg/mL Ampicillin until an OD600 of 0.7 was reached. Cultures were transferred to 16° C. and protein expression induced by the addition of IPTG to a final concentration of 0.5 mM. After the addition of IPTG the cultures were shaken overnight for a further 16 hours. Following expression, cell cultures were centrifuged at 5000×g for 20 min and cell pellets stored frozen at −20° C.

Protein Purification: Protein purification was initiated by thawing the cell pellet in Lysis buffer (25 mM Tris-HCl pH 8.0, 300 mM NaCl, 2 mM $MgCl_2$, 10 mM Imidazole, 0.5 mg/mL lysozyme, 5 U/mL benzonase endonuclease [EMD Millipore], 1 mM PMSF, complete protease inhibitor tablets EDTA-free [Roche]) using a ratio of 5 mL of buffer per 1 g of cells. Cells were further lysed by 3 passes through an ice cooled Avestin C5 cell crusher and centrifuged at 48,000×g at 4° C. Supernatant (cell lysate) was filtered through a 5 µm filter and applied onto a 1 mL HiTrap IMAC Sepharose FF column (GE Healthcare) pre-equilibrated with IMAC Wash buffer 1 (25 mM Tris-HCl pH 8.0, 300 mM NaCl, 10 mM Imidazole) using the Profinia Affinity chromatography purification system (Bio-Rad). The IMAC column was sequentially washed with IMAC Wash buffer 1 and IMAC Wash buffer 2 (25 mM Tris-HCl pH 8.0, 300 mM NaCl, 20 mM Imidazole) and bound HIS-TEV-SUMO-FLAG-RLuc8 protein eluted with IMAC Elution buffer (25 mM Tris-HCl pH 8.0, 300 mM NaCl, 350 mM Imidazole). The IMAC-eluted protein was further purified by passing it through a HiLoad 16/60 Superdex 75 column pre-equilibrated in 1×PBS (137 mM NaCl, 2.7 mM KCl, 4.3 mM Na2HPO4, 1.47 mM KH2PO4 pH 7.4).

The purified protein was incubated with SUMO protease overnight, at 16° C., at a protein to protease ratio of 20:1 to remove the N-terminal HIS and SUMO tags. The next morning, imidazole was added to the reaction to a final concentration of 20 mM and the reaction mixture was passed once more over a 1 mL HiTrap IMAC column to remove the protease and the cleaved tags. Two washes with IMAC Wash buffer 2 followed and the untagged protein—was collected from the unbound fraction and the first IMAC wash. Cleaved FLAG-RLuc8 proteins were concentrated using an Amicon Ultra centrifugal filter unit (Ultra-15 MWCO 10 kDa) and loaded onto a HiLoad 16/60 Superdex 200 column pre-equilibrated in 1×PBS (137 mM NaCl, 2.7 mM KCl, 4.3 mM Na2HPO4, 1.47 mM KH2PO4 pH 7.4). The monomer and dimer were collected separately and protein concentrated to >1.2 mg/mL. The protein was flash-frozen in liquid nitrogen in 100 µL aliquots and stored at −70° C.

Throughout purification, fractions contain RLuc8 were identified by SDS-PAGE analysis and/or Western blot analysis using an anti-His antibody-HRP conjugate and detection by α-chloronaphthol.

Example 4. Preparation of Anti-FLAG Antibody and Anti-FLAG Fab'2 Fragment

Production of anti-FLAG antibody: Anti-FLAG antibody was produced from the anti-FLAG M2 hybridoma (Brizzard et al., 1994) and purified on Ab-Capcher resin (Cosmo Bio). Anti-FLAG (8 mL, 3.5 mg/mL) was desalted to PBS adjusted to pH 6.4 on a HiPrep desalting column (GE Healthcare). Uncut anti-FLAG antibody was isolated by gel filtration (data not shown).

Production of anti-FLAG Fab'2 fragment: Papain (BDH) 10.3 mg was resuspended in 1.03 mL PBS, and cysteine was added to the final concentration of 10 mM. The resulting mixture was incubated at room temperature for ~20 min before being centrifuged (21,000×g, 5 min 4° C.). The concentration of papain was determined from the absorbance at 280 nm to be 1.02 mg/mL. The reduced papain was desalted using a HiTrap desalting column (GE Healthcare) equilibrated with PBS adjusted to pH 6.4.

To determine the optimum ratio of papain to antibody, a series of cleavage reactions were set up with 20 µg anti-FLAG antibody and papain added at enzyme/antibody ratios of 1:5 to 1:2560. The reaction mixture was incubated at 37° C. overnight, in the presence of 0 or 10 mM cysteine, before 5 µL 0.5 M iodoacetamide was added to the reaction mixture to quench the reaction. The extent of the cleavage was then assessed by SDS-PAGE.

For use in the conjugation reactions, 7.6 mg anti-FLAG antibody was added to 0.38 mg papain (enzyme/antibody ratio of 1:20) under non-reducing conditions (0 mM cysteine) and the reaction was allowed to proceed at 37° C. for 15 h before Fab'2 was isolated by gel filtration on a HiLoad 26/60 Superdex 200 column (GE Healthcare) equilibrated with PBS. The purity of the isolated Fab'2 was then assessed by SDS-PAGE.

Example 5. Partial Reduction of Anti-FLAG Antibody and Fab'2 to Expose Free Sulfhydryls Partial reduction of Anti-FLAG antibody: Anti-FLAG antibody was treated with tris(2-carboxyethyl)phosphine (TCEP) (final concentration 50 µM) for 4 h at 25° C. before being desalted into PBS using NAP G-25 desalting columns (GE Healthcare). The reduced antibody was used without further purification in the subsequent conjugation reactions.

Partial reduction of Anti-FLAG Fab'2 fragment: Anti-FLAG Fab'2 was reduced with TCEP (final concentration 100 µM) for 2 h at 25° C. before being diluted with MES buffer (20 mM, pH 6) and applied to a HiTrap SP HP cation exchange column (1 mL, GE Healthcare) equilibrated with the same buffer. The column was washed with Buffer A (PBS) and the bound protein was eluted with a linear gradient from 0-100% Buffer B (PBS to which 0.85 M NaCl has been added). The eluted material was then subjected to mild re-oxidation with dehydroascorbic acid (DHAA) (250 equivalents) for 1 h at 25° C. before DHAA was removed by desalting into PBS on a HiTrap 5 mL desalting column (GE Healthcare) which had been equilibrated with PBS. The resulting Fab' was used without further purification in the subsequent conjugation reactions.

Example 6. Conjugation of RLuc8 to Anti-FLAG Antibody and Anti-FLAG Fab' Via Solulink Linker Preparation of formylbenzamide-RLuc8 derivative: N-His-RLuc8 (25 nmol) in PBS (700 µL) was reacted with 125 nmol Sulfo-S-4FB (N-succinimidyl-4-formylbenzamide, TriLink Biotechnologies; 2.49 µl of 50 mM Sulfo-S-4FB in anhydrous DMSO) and the mixture was allowed to react for 90 minutes at room temperature. Excess Sulfo-S-4FB was removed by desalting on a HiTrap desalting column into PBS. A small aliquot of the formylbenzamide-derivatised protein was subjected to mass spectrometric analysis, with only a trace of formylbenzamide-RLuc8 derivative detected possibly due to this derivative not being able to fly efficiently in the mass spectrometer.

Preparation of hydrazinonicotinamide-antiFLAG antibody derivative: Reduced anti-FLAG antibody (16.4 nmol) in PBS (700 µL) was treated with 164 nmol MHPH (Maleimide HyNic, maleimidyl-6-hydrazine-nicotinamide, Tri-Link Biotechnologies; 3.29 µl of 50 mM MHPH in anhydrous DMSO)) and the mixture was allowed to react for 90 minutes at room temperature. Excess MHPH was removed by desalting on a HiTrap desalting column into PBS. A small aliquot of the hydrazinonicotinamide-derivatised anti-FLAG antibody was subjected to mass spectrometric analysis.

Derivatisation of reduced anti-FLAG antibody with hydrazinonicotinamide could be inferred from mass spectrometry analysis. Mass spectrum of non-derivatised reduced antibody showed peaks at 24110.8 Da (light chain) and multiple peaks at 50282.8 Da and higher (heavy chain, variation in glycosylation). Mass spectrum of hydrazinonicotinamide-derivatised antibody showed a small peak at 50475.6 Da (heavy chain+192.8 Da), corresponding to the addition of hydrazinonicotinamide (expected MW+191.0 Da), suggesting that conjugation had occurred. The amount of heavy chain relative to the light chain decreased as judged by the relative size of the corresponding peaks in this spectrum, suggesting that perhaps the heavy chain had become hydrazinonicotinamide-derivatised but the resulting conjugate was not able to fly efficiently in the mass spectrometer.

Preparation of hydrazinonicotinamide-Fab' derivative: Anti-FLAG Fab' (7.2 nmol) in PBS (600 µL) was treated with 72 nmol MHPH (1.44 µl of 50 mM MHPH in anhydrous DMSO) and the mixture was allowed to react for 90 minutes at room temperature. Excess linker was removed by desalting on a HiTrap desalting column into PBS. A small aliquot of the hydrazinonicotinamide-derivatised anti-FLAG Fab' was subjected to mass spectrometric analysis.

Derivatisation of anti-FLAG Fab' as hydrazinonicotinamide could be inferred from mass spectrometry analysis. Mass spectrum of non-derivatised anti-FLAG Fab' showed peaks at 24112.3 Da (light chain) and 24574.5 Da (papain-cleaved heavy chain). Similar to the spectrum of the antibody derivative, the mass spectrum of hydrazinonicotinamide-derivatised Fab' showed reduced amount of heavy chain relative to the light chain, suggesting that the heavy chain had reacted with the MHPH reagent but the resulting derivative was not able to fly in the mass spectrometer. Moreover, a broad peak at 24781 (+207.9 Da) was observed, which corresponds to a slightly higher MW than predicted (expected +191.0 Da), but the peak was so broad that the mass was hard to determine.

Preparation of RLuc8-antiFLAG antibody conjugate: Two-thirds of the formylbenzamide-derivatised RLuc8 was added to hydrazinonicotinamide-derivatised anti-FLAG antibody. Aniline (final concentration 10 mM) was added and the conjugation reaction was allowed to proceed at 4° C. for about 54 h before a portion (400 µL) was purified by gel filtration on a Superdex 200 10/300 Increase gel filtration column (GE Healthcare) equilibrated with PBS. The elution chromatogram of the formylbenzamide-derivatised RLuc8 and hydrazinonicotinamide-derivatised antibody reaction mixture (data not shown) was dominated by the broad peak at ca. 13.5 mL, whereby the non-derivatised antibody elutes under the same conditions as a sharp peak at 13.5 mL, and RLuc8 elutes as a broad peak at ca. 16.5 mL (data not shown). A small shoulder eluting at about 12.5-13 mL corresponded to the expected elution volume of the conjugate. A small amount of the conjugate was collected as a shoulder at about 11.5-12.5 mL, which is not present in the chromatogram of the non-derivatised anti-FLAG antibody (data not shown).

The remaining reaction mixture was buffer exchanged to 20 mM MES, 150 mM NaCl pH 6.0 using an Amicon 10 kDa MWCO spin concentrator (Merck Millipore). Aniline was added to a final concentration of 10 mM and one portion left at 4° C. and the second portion at room temperature for 16 h before being subjected to gel filtration purification as above. The gel filtration profile for both reactions were very similar to the profile observed for reaction in PBS.

The hydrazinonicotinamide: formylbenzamide bonds absorbs at 354 nm with a molar extinction coefficient of 29000 (TriLink product literature), however the absorbance of the conjugate was too low to allow an estimation of the concentration using the absorbance at 354 nm.

Preparation of RLuc8-antiFab' conjugate: One-third of the formylbenzamide-derivatised RLuc8RLuc8 was added to hydrazinonicotinamide-derivatised anti-FLAG Fab'2. Aniline was added to a final concentration of 10 mM and the conjugation reaction was allowed to proceed at 4° C. for about 54 h before a portion (400 µL) was purified by gel filtration on a Superdex 200 10/300 Increase gel filtration column (GE Healthcare) equilibrated with PBS. The elution profile of the conjugation reaction mixture showed a new peak of protein eluting at 14.5 mL, earlier than either RLuc8 (elution peak at ~16.5 mL) and Fab' (elution peak also at ~16.5 mL).

The remaining reaction mixture was concentrated and buffer exchanged to 20 mM MES, 150 mM NaCl pH 6.0 using an Amicon 10 kDa MWCO spin concentrator (Merck Millipore). Aniline was added to a final concentration of 10 mM and one portion left at 4° C. and the second portion at room temperature for 16 h before being subjected to gel filtration purification as above. The gel filtration profile for both reactions were very similar to the profile observed for reaction in PBS.

The peak corresponding to conjugated protein was collected The hydrazinonicotinamide: formylbenzamide bond absorbs at 354 nm with a molar extinction coefficient of 29000 (TriLink product literature). The concentration of the hydrazinonicotinamide: formylbenzamide bond in the final pool was estimated to be 50 nM (as determined by integration of the chromatogram at 354 nm).

Example 7. Conjugation of RLuc8 to Anti-FLAG Antibody and Anti-FLAG Fab' Via a PEG Linker Using Click Chemistry Preparation of azido-PEG$_n$-RLuc8 derivative: N-His-RLuc8 (25 nmol in 240 µL PBS)) was reacted with azido-dPEG®8-NHS ester (125 nmol) (Quanta Biodesign) for 90 minutes at room temperature. Excess azido-dPEG® 8-NHS ester was removed by desalting on a HiTrap desalting column into PBS. The resulting azido-PEG8-derivatised protein was used without further purification in the subsequent conjugation reactions. A small aliquot of the material was analysed by mass spectrometry.

The mass spectrum of unconjugated N-His-RLuc8 showed the expected peak at 38982 Da, which was consistent with the loss of the N-terminal methionine, and a smaller peak at 39160 which likely corresponded to the addition of an α-N-gluconoyl group (+178 kDa) to the His tag (data not shown). The spectrum of the derivatised protein indicated that 0-7 azido-PEG8 groups (+449.5 Da each) were appended (data not shown).

Preparation of DBCO-PEG$_m$-antiFLAG antibody derivative: Partially reduced anti-FLAG antibody (16.4 nmol) in PBS (700 µL) was treated with DBCO-dPEG® 4-Mal (Quanta Biodesign) (164 nmol; 3.29 µl of 50 mM DBCO-dPEG® 4-Mal in anhydrous DMSO) and the mixture allowed to react for 90 min at 25° C. Excess DBCO-dPEG® 4-Mal was removed by desalting into PBS using a HiTrap column. A small aliquot of the resulting protein was subjected to analysis by mass spectrometry.

Conjugation of reduced anti-FLAG antibody to DBCO-PEG could be inferred from mass spectrometry analysis. Mass spectrum of the reduced antibody (data not shown) showed peaks at 24110.8 Da (light chain) and multiple peaks at 50282.8 Da and higher (heavy chain, variation in glycosylation). While the mass spectrum of the DBCO-PEG4: antibody conjugate did not show conjugation to either light or heavy chain (predicted MW+674.7 Da), the amount of heavy chain relative to the light chain was reduced as judged by the relative size of the corresponding peaks in this spectrum, suggesting that perhaps the heavy chain had reacted with the DBCO-PEG4-Mal but the resulting conjugate was not able to fly in the mass spectrometer.

Preparation of DBCO-PEG$_m$-Fab' derivative: Partially reduced anti-FLAG Fab'2 (7.2 nmol) in PBS (600 µL) was treated with DBCO-dPEG®4-Mal (72 nmol; 1.44 µL of 50 mM DBCO-dPEG® 4-Mal in anhydrous DMSO) and the mixture was allowed to react for 90 min at 25° C. Excess DBCO-dPEG® 4-Mal was removed by desalting into PBS using a HiTrap column. A small aliquot of the resulting protein was subjected to analysis by mass spectrometry.

Conjugation of the anti-FLAG Fab' fragment to DBCO-PEG4 could be inferred from mass spectrometry analysis. Mass spectrum of anti-FLAG Fab' (data not shown) showed peaks at 24112.3 Da (light chain) and 24574.5 Da (papain-cleaved heavy chain). Similar to the spectrum of the antibody conjugate, the mass spectrum of the DBCO-PEG4:Fab' conjugate (data not shown) showed reduced amount of heavy chain relative to the light chain, whereby the peak corresponding to this chain was not visible in the spectrum, suggesting that the heavy chain had reacted with the DBCO-PEG4-Mal but the resulting conjugate was not able to fly in the mass spectrometer. In contrast to the antibody conjugate, the spectrum of DBCO-PEG4:Fab' showed that some conjugation to the light chain had occurred by the presence of the small peak at 24785.4 (+674.1 Da, predicted MW+674.7 Da).

Preparation of RLuc8-antiFLAG antibody conjugate: Approximately two thirds of the azido-PEG8-derivatized was added to the DBCO-PEG4-derivatised anti-FLAG antibody. The resulting respective mixtures were allowed to react at 4° C. for 54 h before being purified by gel filtration on a Superdex 200 10/300 Increase gel filtration column (GE Healthcare) equilibrated with PBS.

Analysis of the elution chromatogram of the azido-PEG8-derivatised RLuc8 and DBCO-PEG4-derivatised antibody reaction mixture (data not shown) indicated that the desired conjugate eluted as a small shoulder at about 12 mL. This peak is not present in the chromatograms of the antibody (elution peak at ~13.5 mL), or RLuc8 (elution peak at ~16.5 mL) obtained under the same conditions.

Preparation of RLuc8-antiFab' conjugate: The remaining azido-PEG8-derivatised RLuc8 was added to the DBCO-PEG4-Fab'. The resulting respective mixtures were allowed to react at 4° C. for 54 h before being purified by gel filtration.

Analysis of the elution chromatogram of the azido-PEG8-derivatised RLuc8 and DBCO-PEG4-derivatised Fab' reaction mixture (data not shown) showed a peak of protein eluting at 14.5 mL, earlier than either RLuc8 (elution peak at ~16.5 mL) or Fab' (elution peak also at ~16.5 mL).

Example 8. BRET Analysis of Antibody:RLuc8 and Fab':RLuc8 Conjugates

The antibody:RLuc8 and Fab':RLuc8 conjugates comprising the Solulink and Click-PEG linkers, were tested to determine the efficiency of energy transfer between the BRET components RLuc8, free or conjugated to antibody or Fab', and GFP$^2$, conjugated to FLAG peptide.

Materials and Methods

FLAG peptide (DYKDDDDK; SEQ ID NO: 7)) was obtained from Peptide 2.0 Inc, US. In a white Optiplate, RLuc8 or RLuc8 conjugate with or without FLAG-GFP$^2$ and FLAG peptide (various concentrations) were made up to a final volume of 95 µL with PBS and incubated for 5 minutes. After incubation, 5 µL of 0.1 mM Coelenterazine 400a (Cayman Chemicals) in ethanol (0.5 nmol) was added and the luminescence/fluorescence was determined. BRET transfer was analysed using a FLUOstar Optima fluorimeter (BMG Labtech) with simultaneous dual emission optics equipped with a 410 nm emission filter in the first position and a 515 nm filter in the second position.

In order to investigate if the order of addition of the reaction components impacted the BRET ratio, the following order of addition were tested: (i) RLuc8 conjugate alone; (ii) RLuc8 conjugate+FLAG-GFP$^2$; (iii) RLuc8 conjugate+ FLAG-GFP$^2$ (incubate for 5 minutes) and add FLAG peptide; (iv) RLuc8 conjugate+FLAG peptide (incubate for 5 minutes) then add FLAG-GFP$^2$; (v) All reagents (with the exception of Coelenterazine 400a) added at the same time. The resulting mixtures were incubated for a further 5 minutes and 5 µL of 0.1 mM Coelenterazine 400a (Cayman Chemicals) in ethanol (0.5 nmol) was added. Luminescence/ fluorescence was determined. BRET transfer was analysed using a FLUOstar Optima fluorimeter (BMG Labtech) with simultaneous dual emission optics equipped with a 410 nm emission filter in the first position and a 515 nm filter in the second position. An integration time of 0.5 s was used for measurements.

The BRET ratio is defined as the ratio of light intensity at 520 nm to that at 420 nm. BRET ratio was calculated by dividing the GFP$^2$ intensity (average 0-5 s) by the RLuc8 intensity (average 0-5 s).

Results

Initial experiments characterised the luciferase activity of the antibody:RLuc8 and Fab':RLuc8 conjugates. The anti-FLAG Fab'-hydrazinonicotinamide:RLuc8-formylbenzamide conjugate, the anti-FLAG mAb-dPEG4-DBCO: RLuc8:dPEG8azide conjugate and the anti-FLAG Fab'-dPEG4-DBCO:RLuc8:dPEG8azide conjugate were found to have luciferase activity when Coelenterazine 400a was added (data not shown). The anti-FLAG Fab'-hydrazinonicotinamide:RLuc8-formylbenzamide conjugate was not tested without the addition of FLAG-GFP$^2$.

Incubation of anti-FLAG conjugates with FLAG-GFP$^2$ before the addition of free FLAG peptide resulted in a BRET ratio of 0.42 for the Solulink linker and of 0.32 for the Click/PEG-linked conjugate. Incubation of anti-Fab' conjugates with FLAG-GFP$^2$ before the addition of free FLAG peptide resulted in a BRET ratio of 0.17 for the Solulink linker and of 0.11 for the Click/PEG-linked conjugate. The antibody-based conjugates produced a much higher BRET ratio than the corresponding Fab'-based counterparts (FIG. 2). The inclusion of free FLAG peptide (850 µM) in the reaction mixture prior to the addition of Coelenterazine 400a reduced the BRET ratio for the Click/PEG-linked conjugates and the mAb-Solulink-RLuc conjugate (FIG. 2). The Click/PEG-linked conjugates were investigated further.

As shown in FIG. 3, changing the order of reagent addition had little effect on the BRET ratio after the addition of the unlabelled FLAG peptide. In all cases there was an approximate 22% decrease in the BRET ratio. Increasing the incubation time to 10 minutes has no effect on the response (%) to 100 nM FLAG peptide (data not shown). When the BRET ratio was determined immediately following the addition of free FLAG peptide to antibody-Click/PEG-RLuc8 that had been pre-incubated with FLAG-GFP$^2$ for 5 minutes to pre-form the complex, the BRET ratio was found to be the same as for the complex without addition of FLAG peptide. However, if the same pre-formed complex was incubated with free FLAG peptide for 5 minutes before determination of BRET ratio, the ratio was found to be the same as for pre-formation of the antibody-Click/PEG-RLuc8:free FLAG peptide complex with subsequent addition of the FLAG-GFP$^2$, suggesting that 5 minutes is sufficient time for the antibody:FLAG peptide:FLAG-GFP$^2$ complex to form. All further assays were carried out by adding the reagents at the same time and incubating for 5 minutes.

Example 9. The Effect of Linker Length on BRET Ratio

Materials and Methods

A series of antibody:RLuc8 and Fab':RLuc8 conjugates with linkers consisting of 12-60 PEG units were produced. Briefly, RLuc8 (165 nmol in 3 mL PBS) was reacted with 2 equivalents of azido-dPEG8-NHS ester, azido-dPEG24-TFP ester or azido-dPEG36-TFP ester (Quanta Biodesign) at 4° C. for 64 h without mixing, before the protein and conjugate were separated from the low MW unreacted Click reagent by gel filtration on a Superdex S200 16/60 column (GE Healthcare) equilibrated with PBS.

The partially reduced anti-FLAG antibody (84 nmol in 3 mL PBS) or Fab' (16 nmol in 3 mL PBS) were reacted with 2 equivalents of DBCO-dPEG4-Mal, DBCO-dPEG12-Mal or DBCO-dPEG24-Mal (Quanta Biodesign) at 4° C. for 64 h without mixing, before the protein and conjugate were separated from the excess low MW Click reagent by gel filtration on a Superdex S200 16/60 column (GE Healthcare) equilibrated with PBS. The extent of DBCO incorporation into the antibody or antibody fragment was estimated from the absorbance of the conjugates at 309 nm ($\varepsilon_{309\ nm}$=12000 $M^{-1}\ cm^{-1}$) to be 0.9-1.0 for the mAb and 1.5-1.6 for the Fab'.

Conjugation reactions were set up between the azido-PEG$_m$-derivatised RLuc8 and approximately equimolar amounts of the DBCO-PEG$_m$-derivatised antibody, or 0.25-0.4 molar equivalents of the DBCO-PEG$_m$-derivatised Fab' due its limited availability. The reactions were incubated at 4° C. for 40 h before being analysed by SDS-PAGE. As the a large amount of starting material remained unreacted, the reaction mixtures were concentrated and left to proceed for a further week before the conjugates were isolated by gel filtration then analysed by SDS-PAGE. SDS-PAGE analysis indicated that conjugation occurred only at the heavy chains (data not shown). The concentration of the purified conjugate was estimated spectroscopically.

The purified conjugates were used in the BRET assays described in Example 8. BRET transfer was determined as previously except a solution of 1 mM Coelenterazine 400a in 50 µL ethanol was prepared, with 0.5 µL being added to the final assay. The BRET ratio was determined using 50 nM antibody- or Fab'-RLuc8 conjugate, 100 or 200 nM FLAG-GFP$^2$ and FLAG peptide, as appropriate. The reaction mixture was made up to volume with PBS. The final reaction volume after the addition of Coelenterazine 400a was 100 µL.

The BRET assays were performed as described in Example 8 except a solution of 1 mM coelenterazine 400a was prepared in 50 µL of ethanol, with 0.5 µL being added to the final assay.

Results

Figure 4A:
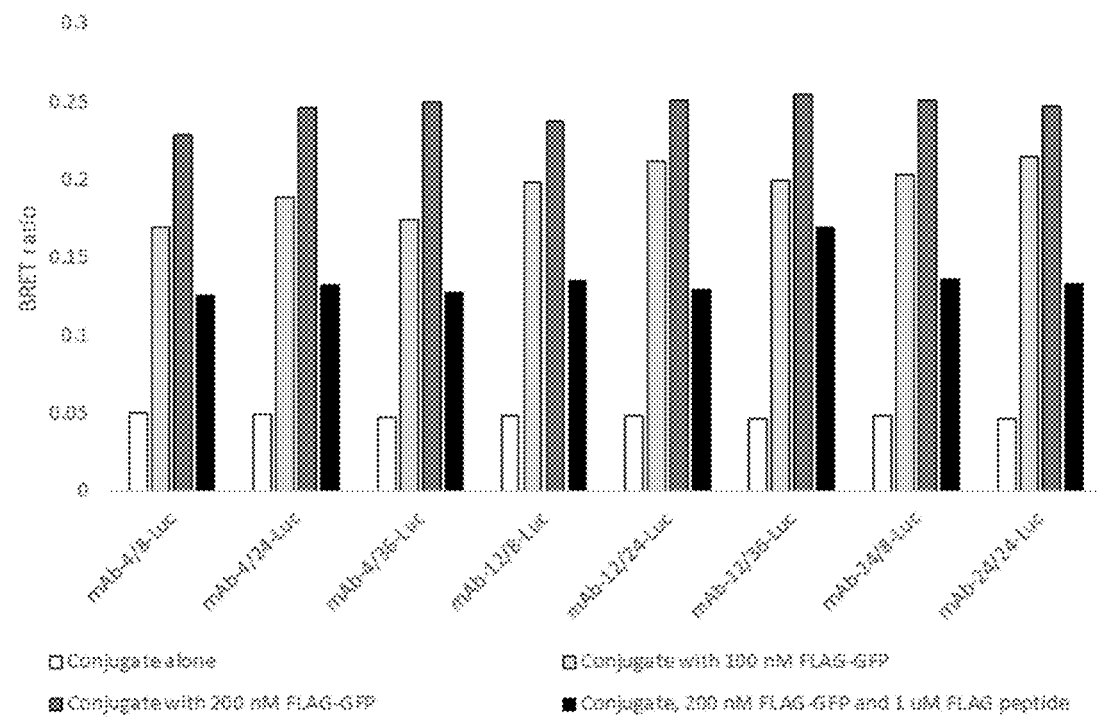
Figure 4B:
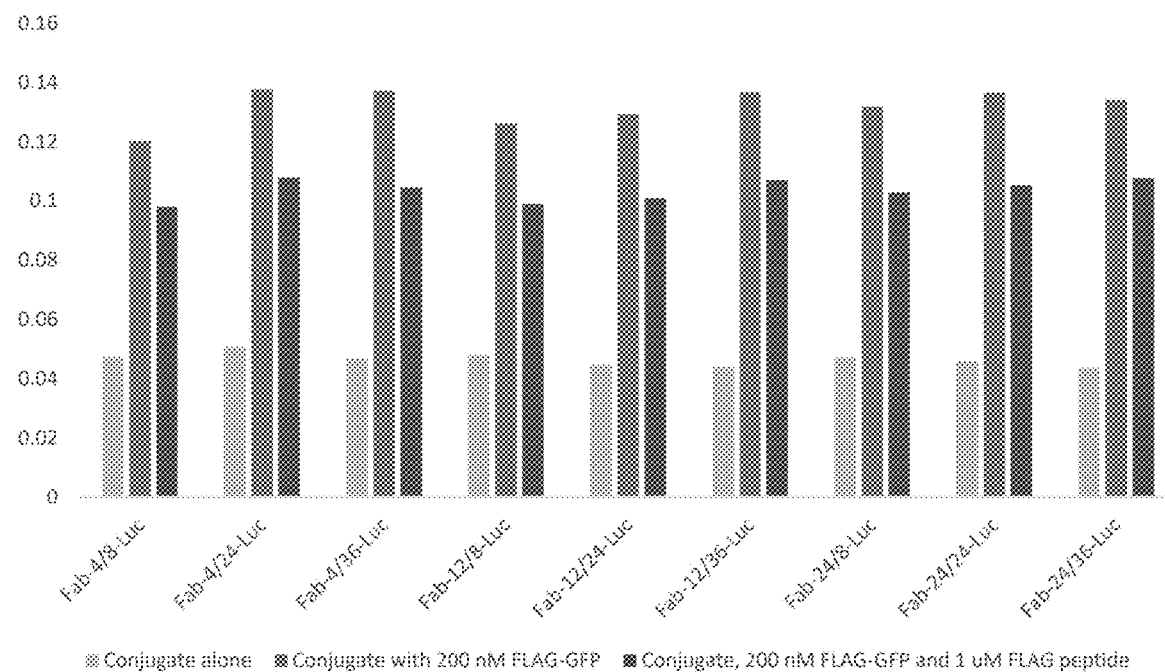

To investigate the effect of the variable length-PEG linker, BRET ratio was determined for each of the antibody-Click/PEG-RLuc8 conjugates alone (50 nM) or with 100 or 200 nM FLAG-GFP$^2$, or with 200 nM FLAG-GFP$^2$ and 1 µM FLAG peptide. The BRET ratio for the antibody-Click/PEG-RLuc8 conjugates increased from 0.05 in the absence of FLAG-GFP$^2$ to approximately 0.2 in the presence of 100 nM FLAG-GFP$^2$, further increasing to 0.25 in the presence of 200 nM FLAG-GFP$^2$ (FIG. 4A). In the presence of 1 µM FLAG peptide, the ratio dropped to approximately half, indicating the FLAG peptide was able to compete for the antibody:RLuc8 conjugate with FLAG-GFP$^2$.

As shown in FIG. 4, there was some variation of BRET ratio for the different lengths of PEG linkers. Thus, there was a slight increase in the BRET ratio in the presence of 200 nM FLAG-GFP$^2$ with the BRET ratio increasing from 0.23 to 0.27 for PEG linker lengths of 12 to 60, respectively. This was accompanied by an increase in response to 1 µM FLAG peptide with the response increasing from 45% with 12-PEG linker to 51% with 60-PEG linker.

A similar effect was found for the Fab'-PEG-RLuc8 conjugates, whereby the BRET ratio of Fab'-RLuc8 and FLAG-GFP$^2$ was smaller than that for the antibody-based counterparts, but a decrease of the BRET ratio in the presence of FLAG peptide was also observed (FIG. 4B), indicating that Fab'-RLuc8 conjugates and FLAG-GFP$^2$ can also be used as sensors for FLAG peptide.

Example 10. Competitive Binding Assay to Determine Analyte Concentration Using Immunosensors Materials and Methods In order to determine whether the immunosensors of the present invention can be used to detect and measure the concentration of an analyte, the antibody-12/36-RLuc8 conjugate was incubated with 200 nM FLAG-GFP$^2$ and varying concentrations of FLAG peptide (from 256 µM to less than 0.5 nM) for 5 minutes before coelenterazine 400a was added and the BRET ratio determined using the Fluorostar plate-reader as described in Example 9. The BRET ratios were plotted against Log [FLAG] values.

A calibration was also performed using the Clariostar plate-reader (BMG) and the antibody-24/36-RLuc8 conjugate. Measurements were made in the bioluminescence mode and the dual linear variable filters were set to 410-80 (Gain: 3300) for RLuc8 emission and 515-30 (Gain: 4095) for GFP$^2$ emission. An integration time of 1.54 s was used. Coelenterazine 400a was prepared by adding 100 µL ethanol to a dried aliquot (0.5 mM), with 1 µL added to the final assay to give a final concentration of 5 µM. A final concentration of 5 nM of RLuc8-conjugate and 10 nM GFP$^2$-FLAG was used for assays. The final assay volume was 100 µL with PBS (with BSA 1 mg/ml) used to make up the volume.

To construct a standard curve using the Clariostar, 5 nM mAb-24/36-RLuc8 conjugate was added to 10 nM FLAG-GFP$^2$ in PBS with BSA (1 mg/mL) and the mixture incubated with unlabelled FLAG peptide (various concentrations) for 5 minutes at 28° C. Coelenterazine 400a was added and the BRET response determined. BRET ratio was calculated by dividing the GFP$^2$ intensity (average 0-13.86 s) by the RLuc8 intensity (average 0-13.86 s). The BRET ratios were normalised using the normalisation function in Graphpad Prism 7 for Windows, plotted against Log [FLAG] values and fitted with a Log [Agonist] vs normalized response—variable slope model.

Results

As shown in FIG. 5 for measurements with the Fluorostar plate-reader, the BRET ratio was dependent on the concentration of the FLAG peptide. This suggests that the antibody-12/36-RLuc8, in the presence of FLAG-GFP$^2$ can be used to determine the amount of FLAG peptide in a sample. The point of inflection in the curve approximately corresponds to the Kd for the antibody:FLAG interaction (180 nM, Hong et al., 2011).

The calibration curve determined using the Clariostar plate-reader with the antibody 24/36-RLuc8 conjugate is shown in FIG. 6. The $EC_{50}$ was calculated to be 1.41 nM of FLAG peptide. The response was linear between 5.41 µM (90%) and 0.37 µM (10%) with a detection limit of 4.16 µM (Blank±SD*3) with a 5 minute incubation. In comparison, the detection limit for a BRET assay based on the Firefly/Cy3.5 BRET system was 0.2 µM (Yamakawa et al., 2002) and the detection limit for a BRET assay based on the GreenLuc/AF610 BRET system was 1.7 nM (Smirnova et al., 2016). This is summarised in Table 4.

From earlier work (Hong et al., 2011)] the Kd for the FLAG-anti-FLAG interaction had been found to be 180 nM for the whole antibody, and ~390 nM for a PEGylated Fab'. Assays performed using the Fluorostar plate reader, a different conjugate (mAb-12/36-RLuc8) and higher concentration (20×) of mAb-PEG-RLuc8 conjugate resulted in an EC50 of 274 nM and in this case the response was linear between 32.4 nM-2.3 µM (90%-10% of maximum response) (FIG. 5).

In conclusion, the immunosensors and methods described herein resulted in an increase in the sensitivity of a low molecular weight antigen assay by a factor of 300 and reduced assay times down to five minutes in comparison to previously published data (20-60 minutes).

TABLE 4

Comparison of assay parameters for BRET-based competitive immunoassay using mab

| Parameters | BRET system | | |
|---|---|---|---|
| Donor | RLuc8/Clz400a | FFLuc/D-luciferin | GreenLuc*/D-luciferin |
| Acceptor | GFP$^2$ | Cy3.5 | AF610 |
| Antibody | Anti-FLAG mAb | Anti-Myc mAb | Anti-Progesterone mAb |
| Antigen | FLAG peptide | Myc peptide | Progesterone |
| Linear range | 5.4 pM-0.4 µM | 0.2-2 µM | 1.7-95 nM |

TABLE 4-continued

Comparison of assay parameters for BRET-
based competitive immunoassay using mab

| Parameters | BRET system | | |
|---|---|---|---|
| Detection limit | 5.4 pM | 0.2 µM | 1.7 nM |
| Assay time (min.) | 5 | 60 | 20 |
| Reference | ** | Yamakawa et al., 2002 | Smirnova et al., 2016 |

RLuc = *Renilla* luciferase, FFLuc = Firefly luciferase, GFP = Green fluorescent protein, Cy = Cyanine, AF = Alexafluor. Linear range = 90-10% of maximum response and detection limit is the blank signal (100%) ± 3 × SD.
*Green variant of *L. mingrelica* luciferase
**Method disclosed here.

Example 11. Synthesis of FLAG-GFP$^2$-PEG4-DBCO-azido-PEG8-ampicillin

Materials and Methods

Synthesis of ampicillin-PEG8-N$_3$: To a stirred solution of the sodium salt of ampicillin (4.8 mg, 0.0128 mmol) in PBS (pH 8.0, 1 mL) a solution of NHS-PEG8-N3 (Quanta Biodesign #10503; N-hydroxysuccinimide ester (polyethylene glycol8)azide) in PBS (pH 8.0, 1 mL) was added and this was stirred for 16 h, at 25° C., and protected from light. The reaction mixture was filtered through a 0.22 µM acrodisc filter and then purified by preparative HPLC (reverse phase C18 column (Gilson HPLC), elution 0-80% B over 16 minutes (elution solvents: A=0.1% TFA in H$_2$O; B=0.1% TFA in acetonitrile), detect at 214 nm). Fractions at 17 mins were combined and reduced to dryness in vacuo. Combined fractions (8 mg, 68.8% yield) were analysed by analytical LC-MS ((Waters Alliance aHPLC, C18 reverse phase, to QDa mass detector) gradient elution 0-80% B, detect at 214 nm). The major peak at 4.09 mins in the aHPLC gave a MS of 797.40 ESI –ve ion mode (M=798.91).

Synthesis of FLAG-GFP$^2$-ampicillin: FLAG-GFP$^2$ (Example 1) was desalted to PBS. 20, 30 or 40 nmol DBCO-dPEG4-TFP ester (Quanta Biodesign) was added to 20 nmol protein and the mixture allowed to react at 4° C. overnight. The reaction mixtures were analysed by mass spectrometry and then pooled. A large excess (1.9 µmol) of ampicillin-PEG8-N$_3$ was added to 56 nmol GFP$^2$-PEG4-DBCO reaction mixture. The reaction was allowed to proceed at 4° C. overnight before being purified by gel filtration and the protein pools analysed by mass spectrometry.

Results

The reaction of FLAG-GFP$^2$ with DBCO-dPEG4-TFP ester was found to produce a mixture of unconjugated protein, and conjugate with one or two adducts of DBCO-PEG4 on reaction with 1, 1.5 or 2 equivalents of DBCO-PEG4-TFP ester (data not shown). Since the products of the three reactions were similar, they were combined and reacted with ampicillin-PEG8-N$_3$. Mass spectrometric analysis showed a mixture of unreacted FLAG-GFP$^2$, and a mixture of one or two adducts (+1365.8, predicted+1348.6).

Example 12. Preparation of Nanobody-Rluc8

Molecular Biology: A codon optimized DNA sequence (for expression in *E. coli*) encoding the single domain camelid nanobody VHH T9 (T9-NB1; Tabares-da Rosa et al., 2011) was synthesised by GenScript USA Inc (Piscataway, New Jersey, USA). This was ligated into a modified pET43a *E. coli* expression vector designed to encode an N-terminal hexahistidine tag followed by a tobacco etch virus protease (TEV) cleavage site, the T9-NB1 sequence, the RLuc8 sequence and a SortaseA bioconjugation sequence (LPETGG). The resulting protein sequence is provided as SEQ ID NO: 8.

Protein Expression: To produce recombinant N-His-T9-NB1-RLuc8 protein, the expression plasmid was transformed into *E. coli* BL21 DE3 strain and grown with shaking at 37° C. in 1 L volumes of TB supplemented with 100 µg/ml Ampicillin until an OD600 of 0.7 was reached. Cultures were transferred to 16° C. and protein expression induced by the addition of IPTG to a final concentration of 0.5 mM and the cultures incubated with shaking for further 16 hours. Following expression, cell cultures were centrifuged at 5000×g for 20 min and the cell pellet stored frozen at –20° C.

Protein Purification: Protein purification was initiated by thawing the cell pellet in Lysis buffer (25 mM Tris-HCl pH 8.0, 300 mM NaCl, 2 mM MgCl$_2$, 10 mM Imidazole, 0.5 mg/ml lysozyme, benzonase endonuclease [EMD Millipore], 1 mM PMSF, complete protease inhibitor tablets EDTA-free [Roche]) using a ratio of 5 ml of buffer per 1 g of cells. Cells were further lysed by 3 passes through an ice cooled Avestin C5 cell crusher and then centrifuged at 48,000×g at 4° C. Supernatant (cell lysate) was filtered through a 5 µm filter and applied to 1 ml HiTrap IMAC Sepharose FF column (GE Healthcare) pre-equilibrated with IMAC wash buffer 1 (25 mM Tris-HCl pH 8.0, 300 mM NaCl, 10 mM Imidazole) using Profinia Affinity chromatography purification system (Bio-Rad). The IMAC column was then sequentially washed with IMAC Wash buffer 1 and IMAC Wash buffer 2 (25 mM Tris-HCl pH 8.0, 300 mM NaCl, 20 mM Imidazole). After washing, bound protein eluted with IMAC Elution buffer (25 mM Tris-HCl pH 8.0, 300 mM NaCl, 350 mM Imidazole).

To remove the N-terminal hexahistidine tag and to also reduce the imidazole concentration to 20 mM, the eluted protein was incubated overnight at 4° C. with TEV protease at a protein to protease molar ratio of 20:1 in a Spectra/Por dialysis membrane (MWCO 3500 Da) while dialysing against IMAC Wash buffer 2 supplemented with 1 mM DTT. The dialysed digestion reaction was then passed over a 1 ml HiTrap IMAC Sepharose FF column to capture the his tagged TEV protease and the cleaved hexahistidine tag. The column was subsequently washed twice with IMAC Wash buffer 2 and the unbound fraction and first IMAC wash (which contained untagged T9-NB1-rLuc8) were pooled. The pooled fractions were concentrated using an Amicon Ultra centrifugal filter unit (Ultra-15 MWCO 10) and loaded onto a HiLoad 16/60 Superdex 200 column pre-equilibrated in 1×PBS. The appropriate peak was collected and the protein was then concentrated to 0.28 mg/ml before flash-freezing in liquid nitrogen and stored at –70° C.

Example 13. Synthesis of TCC-4'-S—(CH$_2$)$_2$—CO-GFP$^2$

General: Unless indicated, all reagents and solvents were purchased from commercial suppliers and used as received. Methyl 3-[(4-aminophenyl)sulfanyl] propanoate was custom synthesised by ChemSpace and was used as received. Analytical LC-MS performed on a Waters Alliance HPLC Synthesis of TCC-4'-S—(CH$_2$)$_2$—CO$_2$H

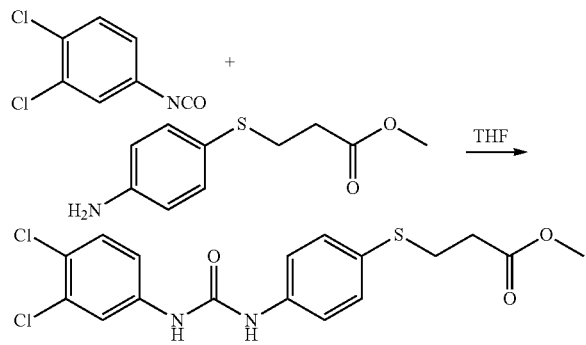

A mixture of 3,4-dichlorophenyl isocyanate (124.1 mg, 0.66 mmol) and methyl 3-[(4-aminophenyl)sulfanyl]propanoate (139.5 mg, 0.66 mmol) in anhydrous tetrahydrofuran (8 mL) was stirred at room temperature for 16 h, under an atmosphere of nitrogen. The volatiles were removed under reduced pressure, and the residue washed with hexanes/ethyl acetate (1:1, 10 mL), the remaining white solid was dried under reduced pressure. Analytical LC-MS showed a single clean peak at 7.132 mins (ESI-MS +ve mode, A=214 nm); MS expected MW 399.29, found 399.08.

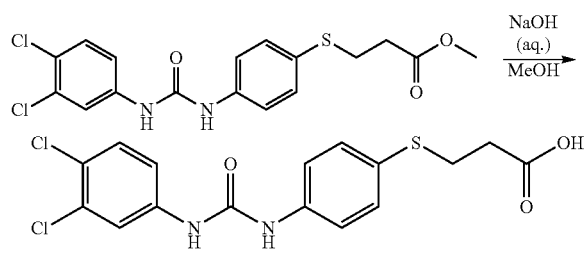

To methyl 4-[3-(3,4-dichlorophenyl)ureido]phenylthiopropionate (264 mg, 0.66 mmol) was added methanol (15 mL) followed by 1M NaOH (aq.) (15 mL). The suspension was heated to 60° C. for 16 hours. After cooling to room temperature, the mixture was acidified, at 0° C., to pH 4.0 with 6 M HCl. The suspension was extracted twice with ethyl acetate/hexanes (1:1, 50 mL), and the combined organic extracts dried over anhydrous sodium sulfate, followed by removal of volatiles under reduced pressure to yield 4{3-(3,4-dichlorophenyl)ureido]phenylthiopropionic acid [TCC-4'-S—(CH$_2$)$_2$—CO$_2$H] as a white solid. Analytical LC-MS showed a single clean peak at 6.434 mins (ESI-MS +ve mode, A=214 nm); MS expected MW 385.26, found 385.01.

Synthesis of TCC-4'-S—(CH$_2$)$_2$—CO-GFP$^2$: TCC-4'-S—(CH$_2$)$_2$—CO$_2$H (2 mg) was dissolved in a mixture of PBS (pH 7.4, 700 µL) and 135 µL DMSO. This solution was then added, at room temperature, to a solution of FLAG-GFP$^2$ in PBS (pH 7.4, 1.25 mL, 1.75 mg). Separately, EDC (10 mg) was dissolved in 1 mL PBS (pH 7.4) and sulfo-NHS (10 mg) was dissolved in 1 mL PBS (pH 7.4). 100 µL of the EDC solution and 100 µL of the sNHS solution were added to the GFP$^2$/TCC-4'-S—(CH$_2$)$_2$—CO$_2$H mixture. The resulting mixture was stirred at room temperature, by gentle rotation, for 16 hours. The TCC-4'-S—(CH$_2$)$_2$—CO-GFP$^2$ conjugate was purified by use of a PD-10 column following the GE Healthcare protocol to yield 3.5 mL of TCC-4'-S—(CH$_2$)$_2$—CO-GFP$^2$ conjugate at 2.84 mg/mL.

Example 14: Detection of a Small Molecule Using a BRET Sensor

In some embodiments, the methods and immunosensors described herein can be used to detect a small molecule, such as TCC. FIG. 7 shows the schematic competitive assay where addition of a small molecule to an exemplified immunosensor described herein results in a decrease in BRET ratio due to competitive binding of the unlabelled, antigen to the nanobody in the place of the labelled antigen.

Instrumentation: Simultaneous dual emission BRET measurements were carried out with a CLARIOstar microplate reader (BMG LabTech). BRET$^2$ measurements used the BRET$^2$ emission filter set comprising RLuc/CLZ400a emission filter (410 nm bandpass, 80 nm) and the GFP$^2$ emission filter (515 nm bandpass, 30 nm). BRET$^2$ ratios were calculated as ratios of integrated acceptor emission channel intensity to integrated donor emission channel intensity.

BRET$^2$ assay: All reactions were carried out in white 96-well plates (Perkin-Elmer, Australia). A final concentration of 10 nM of T9NB1-RLuc8 and 10 nM of TCC-4'-S—(CH$_2$)$_2$—CO-GFP$^2$ were used for all assays, in a final volume of 100 µL 2% DMSO in PBS.

To construct a calibration curve, 10 nM of T9NB1-RLuc8 and 10 nM of TCC-4'-S—(CH$_2$)$_2$—CO-GFP$^2$ were incubated for 5 minutes at 22° C. with a range of different final concentrations of TCC, namely 1, 3, 6.3, 12.5, 25, 50, 100 and 200 nM, added from a stock of TCC in DMSO or DMSO only (2% final concentration in PBS). At the end of the incubation time, 1 µL of coelenterazine 400a (1 mM stock) in EtOH was added to the reaction mixture (final [CLZ400a]=10 µM) and the luminescence intensities recorded immediately. The BRET$^2$ ratios were calculated and are presented as a function of the concentration of TCC in FIG. 8. A dose dependent change in BRET$^2$ ratio of the sensor construct in the presence of the target TCC antigen was observed with an EC$_{50}$ value of 17.3 nM.

A final concentration of 10 nM T9NB1-RLuc8 only, 10 nM T9NB1-RLuc8 with 10 nM of TCC-4'-S—(CH$_2$)$_2$—CO-GFP$^2$ or 10 nM T9NB1-RLuc8 with 10 nM GFP$^2$ were used for control assays, in a final volume of 100 µL 2% DMSO in PBS. For the control assay, the purified proteins were incubated for 5 minutes at 22° C. At the end of the incubation time, 1 µL of coelenterazine 400a (1 mM stock) in EtOH was added to the reaction mixture (final [CLZ400a]=10 µM) and the luminescence intensities were recorded immediately. The BRET$^2$ ratios were calculated and are shown in FIG. 9.

This application claims priority from Australian application no. 2019901483 filed 1 May 2019 and from Australian application no. 2019901566 filed 8 May 2019, the entire contents of which are incorporated by reference herein.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

All publications discussed and/or referenced herein are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Banks and Paquette (1995) Bioconjug. Chem. 6:447-58.
Bhalla et al. (2016) Essays in biochemistry. 60:1-8.
Boutureira and Bernardes (2015) Chem Rev 115:2174-95.
Brizzard et al. (1994) Biotechniques 16:730-5.
Dirksen et al. (2006) J Am Chem Soc 128:15602-3.
Egholm et al. (2005) Nature 365:566-568.
Herve et al. (2008) AAPS J. 10:455-472.
Hong et al. (2011) Australian Journal of Chemistry 64:779-89.
Huse et al. (1989) Science 246:1275-81.
Kirley et al. (2016) Biochem Biophys Res Commun. 480: 752-757.
Kolb et al. (2001) Angew. Chem. Int. Ed. 40:2004-21.
Lang and Chin (2014) Chem. Rev. 114:4764-4806.
Liu and Schultz (2010) Annu. Rev. Biochem. 79:413-444.
Malkoch et al. (2005) J. Am. Chem. Soc. 127:14942-9.
Oteng-Pabi et al. (2014) Chem Commun (Camb). 50(50): 6604-6606.
Singh et al. (1998) Chem. Commun. 455-456.
Smirnova et al. (2016) Photochemistry and Photobiology 92:158-65.
Spicer and Davis (2014) Nature Communications 5, article number: 4740.
Tabares-da Rosa et al. (2011) Anal Chem. 83:7213-20.
Theile et al. (2013) Nat. Protoc. 8(9):1800-1807.
Walker et al. (1989) Molec. Immunol. 26:403-11.
Yamakawa et al. (2002) Journal of Bioscience and Bioengineering 93:537-42.

The invention claimed is:

1. A method for detecting an analyte in a sample, the method comprising:
   i) contacting the sample with a solution comprising:
      a first molecule comprising an antibody or antibody-like molecule capable of binding to the analyte attached to a first component of a chemiluminescence resonance energy transfer (CRET) pair; and
      a second molecule comprising a labelled antigen comprising an antigen capable of binding to the antibody or the antibody-like molecule attached to a second component of the CRET pair,
      wherein:
         (a) the first component of the CRET pair comprises a luciferase and second component of the CRET pair comprises a fluorescent protein, or
         (b) the first component of the CRET pair comprises a fluorescent protein and second component of the CRET pair comprises a luciferase; and
      wherein, when the labelled antigen is bound to the antibody or the antibody-like molecule, the efficiency of energy transfer between the first component of the CRET pair and the second component of the CRET pair is in the range of 10 to 75%; and
   ii) detecting the analyte if the efficiency of energy transfer between the first component of the CRET pair and the second component of the CRET pair has been altered in the presence of the sample,
      wherein a reduction in the efficiency of energy transfer between the first and second components of the CRET pair indicates that the analyte is present in the sample.

2. The method of claim 1, wherein the antibody or antibody-like molecule is attached to the first component of the CRET pair via a linker, wherein the linker comprises a polyethylene glycol (PEG) chain, hydrocarbon chain, a polypeptide or a polynucleotide.

3. The method of claim 2, wherein the linker comprises $PEG_{10}$ to $PEG_{60}$ or (ii) the linker comprises $PEG_n$-L-$PEG_m$, wherein m and n are independently an integer between 0 and 40 and L is a conjugation element.

4. The method of claim 1, wherein the first component of the CRET pair is attached to a side-chain of a residue of the antibody or antibody-like molecule.

5. The method of claim 4, wherein the residue is a cysteine.

6. The method of claim 5, wherein the residue is:
   (i) a cysteine involved in inter-chain disulphide bonds; and/or
   (ii) a cysteine in a hinge region of the antibody or antibody-like molecule or the residue is a cysteine involved in a heavy chain-light chain disulphide bond or a combination of both.

7. The method of claim 1, wherein the first component of the CRET pair is attached to the antibody or antibody-like molecule via a carbohydrate moiety.

8. The method of claim 1, wherein the antibody or antibody-like molecule is an IgG, Fab', rIgG (half antibody), f(ab')$_2$ or nanobody.

9. The method of claim 1, wherein the analyte is a small organic molecule, drug, drug metabolite, antibiotic, hormone, allergen, peptide, protein, naturally occurring antibody, sugar, lipid or nucleic acid.

10. The method of claim 1, wherein the first component of the CRET pair is RLuc8 and the second component of the CRET pair is GFP².

11. The method of claim 1, wherein, when the labelled antigen is specifically bound to the antibody or antibody-like molecule, the separation and relative orientation of the first component of the CRET pair and the second component of the CRET pair is within ±50% of the Forster distance of the CRET pair.

12. The method of claim 1, wherein step (ii) comprises detecting the analyte if the efficiency of energy transfer between the first component of the CRET pair and the second component of the CRET pair has been reduced in the presence of the sample.

13. The method of claim 1, wherein step (i) comprises
    (a) first contacting the sample with the antibody or antibody-like molecule and then contacting the resulting mixture with the labelled antigen;
    (b) first contacting the sample with the labelled antigen and then contacting the resulting mixture with the antibody or antibody-like molecule; or
    (c) contacting the sample with the antibody or antibody-like molecule and the labelled antigen at the same time.

14. The method of claim 1, wherein the method does not require a secondary antibody.

15. The method of claim 1, which further comprises detecting the concentration of the analyte in the sample.

16. A solution comprising a CRET pair comprising:
    an antibody or antibody-like molecule capable of binding to an analyte attached to a first component of a CRET pair; and
    a labelled antigen comprising an antigen capable of binding to the antibody or antibody-like molecule attached to a second component of a CRET pair, wherein:
        (a) the first component of the CRET pair comprises a luciferase and second component of the CRET pair comprises a fluorescent protein, or
        (b) the first component of the CRET pair comprises a fluorescent protein and second component of the CRET pair comprises a luciferase;
    wherein when the labelled antigen is bound to the antibody or antibody-like molecule the efficiency of energy transfer between the first component of the CRET pair and the second component of the CRET pair is in the range of 10 to 75%.

17. A solution comprising a n antibody or antibody-like molecule attached to a first component of a CRET pair and capable of binding to
    i) an analyte; and
    ii) a labelled antigen comprising an antigen capable of binding to the antibody or antibody-like molecule attached to a second component of a CRET pair,
    wherein:
        (a) the first component of the CRET pair comprises a luciferase and second component of the CRET pair comprises a fluorescent protein, or
        (b) the first component of the CRET pair comprises a fluorescent protein and second component of the CRET pair comprises a luciferase, and
    wherein when the labelled antigen is bound to the antibody or antibody-like molecule the efficiency of energy transfer between the first component and the second component is in the range of 10 to 75%.

18. The CRET pair of claim 16, wherein the first component of the CRET pair is a *Renilla* luciferase and the second component of the CRET pair is green fluorescent protein 2.

19. The antibody or antibody-like molecule of claim 17, wherein the first component of a CRET pair is a *Renilla* luciferase and the second component of the CRET pair is green fluorescent protein 2.

* * * * *

```
SEQUENCE LISTING

<160> NUMBER OF SEQ ID NOS: 8

<210> SEQ ID NO 1
<211> LENGTH: 7
<212> TYPE: PRT
<213> ORGANISM: Artificial Sequence
<220> FEATURE:
<223> OTHER INFORMATION: linker

<400> SEQUENCE: 1

Trp Ala Leu Gln Arg Pro His
1               5

<210> SEQ ID NO 2
<211> LENGTH: 7
<212> TYPE: PRT
<213> ORGANISM: Artificial Sequence
<220> FEATURE:
<223> OTHER INFORMATION: Linker

<400> SEQUENCE: 2

Trp Glu Leu Gln Arg Pro Tyr
1               5

<210> SEQ ID NO 3
<211> LENGTH: 4
<212> TYPE: PRT
<213> ORGANISM: Artificial Sequence
<220> FEATURE:
<223> OTHER INFORMATION: Linker
<220> FEATURE:
<221> NAME/KEY: X
<222> LOCATION: (3)..(3)
<223> OTHER INFORMATION: X is any amino acid

<400> SEQUENCE: 3

Leu Pro Xaa Thr
1

<210> SEQ ID NO 4
<211> LENGTH: 365
<212> TYPE: PRT
<213> ORGANISM: Artificial Sequence
<220> FEATURE:
<223> OTHER INFORMATION: FLAG-GFP2
```

<400> SEQUENCE: 4

```
Met Gly His His His His His Gly Thr Glu Asn Leu Tyr Phe Gln
1               5                   10                  15

Ser Met Ser Asp Ser Glu Val Asn Gln Glu Ala Lys Pro Glu Val Lys
            20                  25                  30

Pro Glu Val Lys Pro Glu Thr His Ile Asn Leu Lys Val Ser Asp Gly
            35                  40                  45

Ser Ser Glu Ile Phe Phe Lys Ile Lys Lys Thr Thr Pro Leu Arg Arg
    50                  55                  60

Leu Met Glu Ala Phe Ala Lys Arg Gln Gly Lys Glu Met Asp Ser Leu
65                  70                  75                  80

Arg Phe Leu Tyr Asp Gly Ile Arg Ile Gln Ala Asp Gln Thr Pro Glu
                85                  90                  95

Asp Leu Asp Met Glu Asp Asn Asp Ile Ile Glu Ala His Arg Glu Gln
            100                 105                 110

Ile Gly Gly Gly Ser Asp Tyr Lys Asp Asp Asp Lys Gly Ser Val
        115                 120                 125

Ser Lys Gly Glu Glu Leu Phe Thr Gly Val Val Pro Ile Leu Val Glu
    130                 135                 140

Leu Asp Gly Asp Val Asn Gly His Lys Phe Ser Val Ser Gly Glu Gly
145                 150                 155                 160

Glu Gly Asp Ala Thr Tyr Gly Lys Leu Thr Leu Lys Phe Ile Cys Thr
                165                 170                 175

Thr Gly Lys Leu Pro Val Pro Trp Pro Thr Leu Val Thr Thr Leu Ser
            180                 185                 190

Tyr Gly Val Gln Cys Phe Ser Arg Tyr Pro Asp His Met Lys Gln His
    195                 200                 205

Asp Phe Phe Lys Ser Ala Met Pro Glu Gly Tyr Val Gln Glu Arg Thr
210                 215                 220

Ile Phe Phe Lys Asp Asp Gly Asn Tyr Lys Thr Arg Ala Glu Val Lys
225                 230                 235                 240

Phe Glu Gly Asp Thr Leu Val Asn Arg Ile Glu Leu Lys Gly Ile Asp
                245                 250                 255

Phe Lys Glu Asp Gly Asn Ile Leu Gly His Lys Leu Glu Tyr Asn Tyr
            260                 265                 270

Asn Ser His Asn Val Tyr Ile Met Ala Asp Lys Gln Lys Asn Gly Ile
    275                 280                 285

Lys Val Asn Phe Lys Ile Arg His Asn Ile Glu Asp Gly Ser Val Gln
290                 295                 300

Leu Ala Asp His Tyr Gln Gln Asn Thr Pro Ile Gly Asp Gly Pro Val
305                 310                 315                 320

Leu Leu Pro Asp Asn His Tyr Leu Ser Thr Gln Ser Ala Leu Ser Lys
                325                 330                 335

Asp Pro Asn Glu Lys Arg Asp His Met Val Leu Leu Glu Phe Val Thr
            340                 345                 350

Ala Ala Gly Ile Thr Leu Gly Met Asp Glu Leu Tyr Lys
                355                 360                 365
```

<210> SEQ ID NO 5
<211> LENGTH: 340
<212> TYPE: PRT
<213> ORGANISM: Artificial Sequence
<220> FEATURE:
<223> OTHER INFORMATION: N-His-RLuc8

<400> SEQUENCE: 5

Met Gly His His His His His Gly Thr Glu Asn Leu Tyr Phe Gln
1               5                   10                  15

Gly Ser Ala Ser Lys Val Tyr Asp Pro Glu Gln Arg Lys Arg Met Ile
            20                  25                  30

Thr Gly Pro Gln Trp Trp Ala Arg Cys Lys Gln Met Asn Val Leu Asp
        35                  40                  45

Ser Phe Ile Asn Tyr Tyr Asp Ser Glu Lys His Ala Glu Asn Ala Val
    50                  55                  60

Ile Phe Leu His Gly Asn Ala Thr Ser Ser Tyr Leu Trp Arg His Val
65                  70                  75                  80

Val Pro His Ile Glu Pro Val Ala Arg Cys Ile Ile Pro Asp Leu Ile
                85                  90                  95

Gly Met Gly Lys Ser Gly Lys Ser Gly Asn Gly Ser Tyr Arg Leu Leu
            100                 105                 110

Asp His Tyr Lys Tyr Leu Thr Ala Trp Phe Glu Leu Leu Asn Leu Pro
        115                 120                 125

Lys Lys Ile Ile Phe Val Gly His Asp Trp Gly Ala Ala Leu Ala Phe
    130                 135                 140

His Tyr Ala Tyr Glu His Gln Asp Arg Ile Lys Ala Ile Val His Met
145                 150                 155                 160

Glu Ser Val Val Asp Val Ile Glu Ser Trp Asp Glu Trp Pro Asp Ile
                165                 170                 175

Glu Glu Asp Ile Ala Leu Ile Lys Ser Glu Glu Gly Glu Lys Met Val
        180                 185                 190

Leu Glu Asn Asn Phe Phe Val Glu Thr Val Leu Pro Ser Lys Ile Met
    195                 200                 205

Arg Lys Leu Glu Pro Glu Glu Phe Ala Ala Tyr Leu Glu Pro Phe Lys
210                 215                 220

Glu Lys Gly Glu Val Arg Arg Pro Thr Leu Ser Trp Pro Arg Glu Ile
225                 230                 235                 240

Pro Leu Val Lys Gly Gly Lys Pro Asp Val Val Gln Ile Val Arg Asn
            245                 250                 255

Tyr Asn Ala Tyr Leu Arg Ala Ser Asp Asp Leu Pro Lys Leu Phe Ile
        260                 265                 270

Glu Ser Asp Pro Gly Phe Phe Ser Asn Ala Ile Val Glu Gly Ala Lys
    275                 280                 285

Lys Phe Pro Asn Thr Glu Phe Val Lys Val Lys Gly Leu His Phe Leu
290                 295                 300

Gln Glu Asp Ala Pro Asp Glu Met Gly Lys Tyr Ile Lys Ser Phe Val
305                 310                 315                 320

Glu Arg Val Leu Lys Asn Glu Gln Leu Pro Thr Gly Gly Ala Ala
                325                 330                 335

Leu Glu Ala Ser
            340

<210> SEQ ID NO 6
<211> LENGTH: 449
<212> TYPE: PRT
<213> ORGANISM: Artificial Sequence
<220> FEATURE:
<223> OTHER INFORMATION: FLAG-RLuc8

<400> SEQUENCE: 6

Met Gly His His His His His Gly Thr Glu Asn Leu Tyr Phe Gln

-continued

```
1               5                   10                  15
Ser Met Ser Asp Ser Glu Val Asn Gln Glu Ala Lys Pro Glu Val Lys
                20                  25                  30
Pro Glu Val Lys Pro Glu Thr His Ile Asn Leu Lys Val Ser Asp Gly
                35                  40                  45
Ser Ser Glu Ile Phe Phe Lys Ile Lys Lys Thr Thr Pro Leu Arg Arg
 50                  55                  60
Leu Met Glu Ala Phe Ala Lys Arg Gln Gly Lys Glu Met Asp Ser Leu
 65                  70                  75                  80
Arg Phe Leu Tyr Asp Gly Ile Arg Ile Gln Ala Asp Gln Thr Pro Glu
                85                  90                  95
Asp Leu Asp Met Glu Asp Asn Asp Ile Ile Glu Ala His Arg Glu Gln
                100                 105                 110
Ile Gly Gly Gly Ser Asp Tyr Lys Asp Asp Asp Lys Gly Ser Ala
                115                 120                 125
Ser Lys Val Tyr Asp Pro Glu Gln Arg Lys Arg Met Ile Thr Gly Pro
 130                 135                 140
Gln Trp Trp Ala Arg Cys Lys Gln Met Asn Val Leu Asp Ser Phe Ile
 145                 150                 155                 160
Asn Tyr Tyr Asp Ser Glu Lys His Ala Glu Asn Ala Val Ile Phe Leu
                165                 170                 175
His Gly Asn Ala Thr Ser Ser Tyr Leu Trp Arg His Val Val Pro His
                180                 185                 190
Ile Glu Pro Val Ala Arg Cys Ile Ile Pro Asp Leu Ile Gly Met Gly
                195                 200                 205
Lys Ser Gly Lys Ser Gly Asn Gly Ser Tyr Arg Leu Leu Asp His Tyr
 210                 215                 220
Lys Tyr Leu Thr Ala Trp Phe Glu Leu Leu Asn Leu Pro Lys Lys Ile
 225                 230                 235                 240
Ile Phe Val Gly His Asp Trp Gly Ala Ala Leu Ala Phe His Tyr Ala
                245                 250                 255
Tyr Glu His Gln Asp Arg Ile Lys Ala Ile Val His Met Glu Ser Val
                260                 265                 270
Val Asp Val Ile Glu Ser Trp Asp Glu Trp Pro Asp Ile Glu Glu Asp
                275                 280                 285
Ile Ala Leu Ile Lys Ser Glu Glu Gly Glu Lys Met Val Leu Glu Asn
                290                 295                 300
Asn Phe Phe Val Glu Thr Val Leu Pro Ser Lys Ile Met Arg Lys Leu
 305                 310                 315                 320
Glu Pro Glu Glu Phe Ala Ala Tyr Leu Glu Pro Phe Lys Glu Lys Gly
                325                 330                 335
Glu Val Arg Arg Pro Thr Leu Ser Trp Pro Arg Glu Ile Pro Leu Val
                340                 345                 350
Lys Gly Gly Lys Pro Asp Val Val Gln Ile Val Arg Asn Tyr Asn Ala
                355                 360                 365
Tyr Leu Arg Ala Ser Asp Asp Leu Pro Lys Leu Phe Ile Glu Ser Asp
 370                 375                 380
Pro Gly Phe Phe Ser Asn Ala Ile Val Glu Gly Ala Lys Lys Phe Pro
 385                 390                 395                 400
Asn Thr Glu Phe Val Lys Val Lys Gly Leu His Phe Leu Gln Glu Asp
                405                 410                 415
Ala Pro Asp Glu Met Gly Lys Tyr Ile Lys Ser Phe Val Glu Arg Val
                420                 425                 430
```

```
Leu Lys Asn Glu Gln Leu Pro Glu Thr Gly Gly Ala Ala Leu Glu Ala
        435                 440                 445
Ser

<210> SEQ ID NO 7
<211> LENGTH: 8
<212> TYPE: PRT
<213> ORGANISM: Artificial Sequence
<220> FEATURE:
<223> OTHER INFORMATION: FLAG peptide

<400> SEQUENCE: 7

Asp Tyr Lys Asp Asp Asp Asp Lys
1               5

<210> SEQ ID NO 8
<211> LENGTH: 466
<212> TYPE: PRT
<213> ORGANISM: Artificial Sequence
<220> FEATURE:
<223> OTHER INFORMATION: Nanobody Sensor

<400> SEQUENCE: 8

Met Gly His His His His His His Gly Thr Glu Asn Leu Tyr Phe Gln
1               5                   10                  15

Ser Ala Glu Val Gln Leu Val Glu Ser Gly Gly Gly Leu Val Gln Thr
                20                  25                  30

Gly Asp Ser Leu Arg Leu Ser Cys Ala Ala Ser Gly Arg Thr Tyr Thr
            35                  40                  45

Pro Tyr Ala Met Ala Trp Phe Arg Gln Ala Pro Gly Lys Glu Arg Glu
        50                  55                  60

Phe Val Ala Gly Ile Gly Gly Ile Asp Gly Thr Ala Ala Tyr Ala Asp
65                  70                  75                  80

Ser Val Arg Gly Arg Ala Thr Ile Ser Arg Asp Ser Ala Lys Lys Thr
                85                  90                  95

Val Tyr Leu Gln Met Asn Ser Leu Lys Pro Glu Asp Thr Ala Val Tyr
                100                 105                 110

Ser Cys Ala Thr Arg Ala Ser Met Gln Val Leu Thr Ser Pro Arg Val
            115                 120                 125

Tyr Pro Ile Trp Gly Arg Gly Thr Gln Val Thr Val Ser Ser Gly Ser
        130                 135                 140

Ala Ser Lys Val Tyr Asp Pro Glu Gln Arg Lys Arg Met Ile Thr Gly
145                 150                 155                 160

Pro Gln Trp Trp Ala Arg Cys Lys Gln Met Asn Val Leu Asp Ser Phe
                165                 170                 175

Ile Asn Tyr Tyr Asp Ser Glu Lys His Ala Glu Asn Ala Val Ile Phe
                180                 185                 190

Leu His Gly Asn Ala Thr Ser Ser Tyr Leu Trp Arg His Val Val Pro
            195                 200                 205

His Ile Glu Pro Val Ala Arg Cys Ile Ile Pro Asp Leu Ile Gly Met
        210                 215                 220

Gly Lys Ser Gly Lys Ser Gly Asn Gly Ser Tyr Arg Leu Leu Asp His
225                 230                 235                 240

Tyr Lys Tyr Leu Thr Ala Trp Phe Glu Leu Leu Asn Leu Pro Lys Lys
                245                 250                 255

Ile Ile Phe Val Gly His Asp Trp Gly Ala Ala Leu Ala Phe His Tyr
                260                 265                 270
```

```
Ala Tyr Glu His Gln Asp Arg Ile Lys Ala Ile Val His Met Glu Ser
        275                 280                 285

Val Val Asp Val Ile Glu Ser Trp Asp Glu Trp Pro Asp Ile Glu Glu
    290                 295                 300

Asp Ile Ala Leu Ile Lys Ser Glu Glu Gly Glu Lys Met Val Leu Glu
305                 310                 315                 320

Asn Asn Phe Phe Val Glu Thr Val Leu Pro Ser Lys Ile Met Arg Lys
                325                 330                 335

Leu Glu Pro Glu Glu Phe Ala Ala Tyr Leu Glu Pro Phe Lys Glu Lys
            340                 345                 350

Gly Glu Val Arg Arg Pro Thr Leu Ser Trp Pro Arg Glu Ile Pro Leu
            355                 360                 365

Val Lys Gly Gly Lys Pro Asp Val Val Gln Ile Val Arg Asn Tyr Asn
    370                 375                 380

Ala Tyr Leu Arg Ala Ser Asp Asp Leu Pro Lys Leu Phe Ile Glu Ser
385                 390                 395                 400

Asp Pro Gly Phe Phe Ser Asn Ala Ile Val Glu Gly Ala Lys Lys Phe
                405                 410                 415

Pro Asn Thr Glu Phe Val Lys Val Lys Gly Leu His Phe Leu Gln Glu
            420                 425                 430

Asp Ala Pro Asp Glu Met Gly Lys Tyr Ile Lys Ser Phe Val Glu Arg
            435                 440                 445

Val Leu Lys Asn Glu Gln Leu Pro Glu Thr Gly Gly Ala Ala Leu Glu
    450                 455                 460

Ala Ser
465
```